United States Patent [19]
Goldin et al.

[11] Patent Number: 6,143,791
[45] Date of Patent: *Nov. 7, 2000

[54] THERAPEUTIC GUANIDINES

[75] Inventors: Stanley M. Goldin, Lexington; James B. Fischer, Cambridge; Andrew Gannett Knapp, Salem; N. Laxma Reddy, Malden; David Berlove, Cambridge; Graham J. Durant, Marshfield; Subbarao Katragadda, Belmont; Lain-Hu Hu, Bedford; Sharad Magar, Somerville, all of Mass.; Wenhong Fan, Rockey Hill, Conn.; Elizabeth Yost; Jun Qing Guo, both of Waltham, Mass.

[73] Assignee: Cambridge NeuroScience, Inc., Cambridge, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/482,984

[22] Filed: Jun. 7, 1995

Related U.S. Application Data

[63] Continuation-in-part of application No. PCT/US95/01536, Feb. 3, 1995, which is a continuation-in-part of application No. 08/191,793, Feb. 3, 1994, abandoned.

[51] Int. Cl.$^7$ ............... A61K 31/155; A61K 31/405; A61K 31/445; A61K 31/50

[52] U.S. Cl. ............ 514/634; 514/239.5; 514/247; 514/319; 514/325; 514/329; 514/415; 544/154; 544/155; 544/164; 544/230; 544/232; 544/294; 546/171; 546/203; 546/204; 546/205; 546/206; 546/223; 548/469

[58] Field of Search ................... 564/230, 237, 564/238, 239; 514/634, 239.5, 247, 319, 325, 329, 415; 544/154, 155, 164, 230, 232, 294; 546/171, 203, 204, 205, 206, 223; 548/469

[56] References Cited

U.S. PATENT DOCUMENTS

| | | | |
|---|---|---|---|
| 1,422,506 | 7/1922 | Weiss | 564/238 |
| 1,597,233 | 8/1926 | Heuser et al. | 564/238 |
| 1,642,180 | 9/1927 | Scott | 564/238 |

(List continued on next page.)

FOREIGN PATENT DOCUMENTS

| | | |
|---|---|---|
| 0001500 | 4/1979 | European Pat. Off. . |
| 0035374 | 9/1981 | European Pat. Off. . |
| 0179642 | 4/1986 | European Pat. Off. . |
| 514248 | 11/1930 | Germany . |
| 2029707 | 12/1970 | Germany . |
| 2133 056 | 1/1973 | Germany . |
| 2452691 | 5/1975 | Germany . |
| 3108564 | 11/1982 | Germany . |
| 223410 | 10/1924 | United Kingdom . |
| 224376 | 11/1924 | United Kingdom . |
| 258203 | 9/1926 | United Kingdom . |
| 478525 | 1/1938 | United Kingdom . |
| 1208252 | 10/1970 | United Kingdom . |
| WO 87/04433 | 7/1987 | WIPO . |
| WO 88/00583 | 1/1988 | WIPO . |
| WO 90/12575 | 11/1990 | WIPO . |
| WO 90/14067 | 11/1990 | WIPO . |
| WO 91/12797 | 9/1991 | WIPO . |
| WO 91/18868 | 12/1991 | WIPO . |
| WO 92/14697 | 9/1992 | WIPO . |
| WO 94/27591 | 12/1994 | WIPO . |
| WO 95/14461 | 6/1995 | WIPO . |
| WO 95/20950 | 8/1995 | WIPO . |

OTHER PUBLICATIONS

D. Lloyd et al., *Tetrahedron*, 33:1379–1389 (1977).
H. Shimazu et al., *Chemical Abstracts*, 111(2):16337m (1989).
T. Tada et al., *Chemical Abstracts*, 104(24):208252g (1986).
L. Kiselev et al., *Chemical Abstracts*, 91(21):175291b (1979).
A. Heesing et al., *Chemical Abstracts*, 64(1):15776h (1966).
K. Akiba et al., *Bull. Chem. Soc. Jap.*, 47(4):935–937 (1974).
Database Rtecs, "National Institute of Occupational Safety and Health", RTECS No. MF735000.
J. Keana et al., *Proc. Natl. Acad. Sci.*, 86:5631–5635 (1989).
S. Siddiqui et al., *Pakistan Journal of Scientific and Industrial Res.*, 30(3):163–181 (1987).
E. Maida et al., *Wiener Klinische Wochenschrift*, 90(2):43–48 (1978).
C. Chavkin et al., *Advances in the Biosciences*, 75:407–410 (1989).
P.N. Bhargava et al., *Chemical Abstracts*, 86:598, 189787b (1977).
H.W. Geluk et al., *J. Med. Chem.*, 12:712–715 (1969).
M.W. Scherz et al., *J. Med. Chem.*, 33:2421–2429 (1990).
A.A. Stolyarchuk et al., *Chemical Abstracts*, 86:522–523, 121071h (1977).
T.J.R. Weakley et al., *Acta. Cryst.*, 46:2234–2236 (1990).
J.T. Adams et al., *Eur. J. Pharm.*, 142:61–71 (1987).
B.G. Campbell et al., *J. Neurosci.*, 9:3380–3391 (1989).
G.J. Durant et al., *J. Med. Chem.*, 28:1414–1422 (1985).
M.P. Kavanaugh et al., *Proc. Natl. Acad. Sci. USA*, 85:2844–2848 (1988).
B. Tester et al., *Society for Neuroscience, 19th Annual Meeting*, 983, 396.17 (1989).
E. Weber et al., *Proc. Natl. Acad. Sci. USA*, 83:8784–8788 (1986).
C.A. Maryanoff et al., *J. Org. Chem.*, 51:1882–1884 (1986).
S.R. Safir et al., *J. Org. Chem.*, 13:924–932 (1948).
F.R. Sharp et al., *Society for Neuroscience Abstr.*, 18, Abstr. No. 482.3 (1992).

(List continued on next page.)

*Primary Examiner*—Peter O'Sullivan
*Attorney, Agent, or Firm*—Dike, Bronstein, Roberts & Cushman, LLP; David G. Conlin; Peter F. Corless

[57] ABSTRACT

The present invention provides therapeutically useful substituted guanidines, and methods of treatment and pharmaceutical compositions that utilize or comprise one or more of such guanidines.

12 Claims, No Drawings

U.S. PATENT DOCUMENTS

| | | | |
|---|---|---|---|
| 1,672,431 | 6/1928 | Schotte | 564/238 |
| 1,677,235 | 7/1928 | Heuser | 564/238 |
| 1,730,388 | 10/1929 | Brooks | 564/238 |
| 1,756,315 | 4/1930 | terHorst | 564/238 |
| 1,795,398 | 3/1931 | Schotte | 564/238 |
| 1,850,682 | 3/1932 | Meiss | 564/238 |
| 1,915,922 | 6/1933 | Christmann et al. | 564/238 |
| 2,145,214 | 1/1939 | Jayne, Jr. | 167/37 |
| 2,254,009 | 8/1941 | Hechenbleikner | 260/564 |
| 2,274,476 | 2/1942 | Hechenbleikner | 167/30 |
| 2,289,541 | 7/1942 | Ericks et al. | 167/22 |
| 2,362,915 | 11/1944 | MacGregor | 3/74 |
| 2,633,474 | 3/1953 | Beaver | 260/565 |
| 2,704,710 | 3/1955 | Sprung | 95/2 |
| 3,117,994 | 1/1964 | McKay et al. | 260/564 |
| 3,140,231 | 7/1964 | Luskin et al. | 167/65 |
| 3,159,676 | 12/1964 | Spickett et al. | 360/564 |
| 3,168,562 | 2/1965 | Walton et al. | 564/237 |
| 3,228,975 | 1/1966 | Abraham et al. | 260/501 |
| 3,248,426 | 4/1966 | Dvornik | 260/564 |
| 3,252,861 | 5/1966 | Mull | 167/65 |
| 3,270,054 | 8/1966 | Gagneux et al. | 260/564 |
| 3,283,003 | 11/1966 | Jack et al. | 260/564 |
| 3,301,755 | 1/1967 | Mull | 167/65 |
| 3,320,229 | 5/1967 | Szabo et al. | 260/96.5 |
| 3,391,189 | 7/1968 | Mull | 260/564 |
| 3,409,669 | 11/1968 | Dyke | 260/564 |
| 3,479,437 | 11/1969 | Szabo et al. | 424/304 |
| 3,547,951 | 12/1970 | Hardie et al. | 260/340.9 |
| 3,639,477 | 2/1972 | L'Italien | 260/564 A |
| 3,681,459 | 8/1972 | Hughes et al. | 424/326 |
| 3,769,427 | 10/1973 | Hughes et al. | 424/326 |
| 3,784,643 | 1/1974 | Suh et al. | 260/564 A |
| 3,795,533 | 3/1974 | Gauri | 117/54 |
| 3,803,324 | 4/1974 | Winter et al. | 424/326 |
| 3,804,898 | 4/1974 | Panneman | 260/564 A |
| 3,908,013 | 9/1975 | Hughes et al. | 424/258 |
| 3,949,089 | 4/1976 | Maxwell et al. | 424/326 |
| 3,968,243 | 7/1976 | Maxwell et al. | 424/326 |
| 3,976,643 | 8/1976 | Diamond et al. | 260/247.5 R |
| 3,976,787 | 8/1976 | Hughes et al. | 424/326 |
| 4,007,181 | 2/1977 | DuCharme et al. | 260/247.5 R |
| 4,014,934 | 3/1977 | Hughes et al. | 260/565 |
| 4,051,256 | 9/1977 | Swallow | 424/304 |
| 4,052,455 | 10/1977 | Matier et al. | 260/563 R |
| 4,060,640 | 11/1977 | Kodama et al. | 424/326 |
| 4,109,014 | 8/1978 | Liu et al. | 424/326 |
| 4,130,663 | 12/1978 | Matier et al. | 424/326 |
| 4,161,541 | 7/1979 | Rasmussen | 424/326 |
| 4,169,154 | 9/1979 | Cohen et al. | 424/322 |
| 4,393,077 | 7/1983 | Douglas et al. | 564/238 |
| 4,471,137 | 9/1984 | Barton et al. | 564/240 |
| 4,709,094 | 11/1987 | Weber et al. | 564/238 |
| 4,742,054 | 5/1988 | Naftchi | 514/215 |
| 4,837,218 | 6/1989 | Olney | 514/646 |
| 4,891,185 | 1/1990 | Goldin | 422/69 |
| 4,898,978 | 2/1990 | Bergfield et al. | 564/231 |
| 4,906,779 | 3/1990 | Weber et al. | 564/238 |
| 5,093,525 | 3/1992 | Weber et al. | 564/238 |
| 5,190,976 | 3/1993 | Weber et al. | 514/634 |
| 5,262,568 | 11/1993 | Weber et al. | 564/238 |
| 5,298,657 | 3/1994 | Durant | 564/238 |
| 5,308,869 | 5/1994 | Keana et al. | 514/637 |
| 5,312,840 | 5/1994 | Keana et al. | 514/634 |
| 5,336,689 | 8/1994 | Weber et al. | 514/634 |
| 5,385,946 | 1/1995 | Keana et al. | 514/634 |

OTHER PUBLICATIONS

B. Clement et al., *Xenobiotica*, 23(2):155–167 (1993).
Kiselev et al., *Chemical Abstracts*, vol. 66 (1967).
B. Bean, *Ann. N.Y. Acad. Sci.*, 560:334–345 (1989).
B. Bean, *Annu. Rev. Physiol.*, 51:367–384 (1989).
Bent et al., *Pesticides*, 74:63479m (1971).
Chernevskaya et al., *Nature*, 349:418–420 (1991).
D. Choi, *Journal of Neuroscience*, 10(8):2493–2501 (1990).
D. Choi, *Cerebrovascular and Brain Metabolism Reviews*, 2:105–147 (1990).
D. Choi, *Neuron*, 1:623–634 (1988).
Dreyer et al., *Science*, 248:364–367 (1990).
Durant et al., *J. Med. Chem.* 9:22–27 (1966).
Fox et al., *J. Physiol.*, 394:149–172 (1987).
Fox et al., *J. Physiol.*, 394:173–200 (1987).
Ginsburg et al., *Chemical Abstracts*, 4518 (1962).
Ginsburg et al., *Zhurnal Organicheskoi Khimii*, 7(11):2267–2270, Unverified Translation (1971).
Godfraind et al., *Trends in Phamacological Sciences*, 10(8):297–301 (1989).
S. Goldin et al., *Synthetic Neuroprotective Glutamate Release Blockers*, Small Business Innovation Research Program Phase I Grant Application, funded Dec. 1991.
L. Heinisch, *Journal f. prakt. Chemie*, 329:290–300 (1987).
Huisgen et al., *Chem. Ber.*, 98:1476–1486 (1965).
Huisgen et al., *Chem. Abstracts*, 63:2975 (1965).
Kaneko et al., *Arzneim. Forsch./Drug. Res.*, 39(1):445–450 (1989).
Katragadda et al., *Soc. for Neurosci. Abstr.*, 16:64 (1990).
Kreutzberger et al., *Arch. Pharmz. Ber. Deut. Pharm. Ges.*, 305:400–405 (1972).
Kroeger et al., *Chem. Abstr.*, 60:9264 (1964).
Kroger et al., *Ber.*, 97:396–404 (1964).
Langlais et al., *J. Neuroscience*, 10(5):1664–1674 (1990).
Lemos et al., *Neuron*, 2:1419–1426 (1996).
Leung et al., *Neuron*, 3:767–772 (1989).
Malgouris et al., *J. Neuroscience*, 9(11):3720–3727 (1989).
B. Meldrum, *Cerebrovascular and Brain Metabolism Reviews*, 2:27–57 (1990).
Miura et al., *Chem. Abstr.*, 109:75455d (1988).
Plaitakis et al., *Science*, 216:193–196 (1982).
Plummer et al., *Neuron*, 2:1453–1463 (1989).
Podrebarac et al., *J. Med. Chem.*, 6:283–288 (1963).
Prasad et al., *Can. J. Chem.*, 45:2247–2252 (1967).
Price et al., *Soc. Neuroscience Abstracts*, 16:377 (1990).
Sah et al., *Soc. Neuroscience Abstr.*, 15:823 (1989).
Sasaki et al., *Synthesis Nov.*, (11):718–719 (1975).
Subbarao et al., *Soc. for Neurosci. Abstr.*, 15:601 (1989).
Sunderdiek et al., *Chemical Abstracts*, 81:91438k (1974).
J.B. Suszkiw, *NATO ASI Series*, H21:285–291 (1988).
Turner et al., *Soc. Neurosci. Abstr.*, 16:1014 (1990).
Turner et al., *Biochemistry*, 28:586–593 (1989).
Turner et al., *Analytical Biochemistry*, 178:8–16 (1989).
Turner et al., *Journal of Neuroscience*, 5(3):841–849 (1985).
Vasilev et al., *Chemical Abstract*, 93:1500095u (1980).
Ahmad et al., *Chemical Abstract*, 108:221382 (1988).
Doull et al., A Survey of Compounds for Radiation Protection (USAF Radiation Laboratory).
K. Ozeki et al., *Chem. Pharm. Bull.*, 37(7):1780–1787 (1989).

THERAPEUTIC GUANIDINES

This application is a continuation of International application PCT/US95/01536, filed Feb. 3, 1995, which in turn is a continuation-in-part of U.S. application Ser. No. 08/191,793, filed Feb. 3, 1994 now abandoned.

This application is a continuation-in-part of copending Interrnational Application PCT/US95/01536 which designated the U.S., which in turn is a continuation-in-part of U.S. application Ser. No. 08/191,793, filed Feb. 3, 1994, both said applications incorporated herein by reference.

BACKGROUND OF THE INVENTION

1. Field of the Invention

The present invention pertains to certain substituted guanidines, and methods of treatment and pharmaceutical compositions that utilize or comprise one or more such guanidines.

2. Background

Neurons of the mature central nervous system ("CNS") are highly specialized and in general do not replace themselves. Consequently, death or degeneration of cells in the nervous system can have far more serious consequences than cell death or degeneration in other organs. Abnormal neuronal death can be rapid and widespread as in traumatic brain injury, or can occur over many years among very specific populations of neurons as in chronic neurodegenerative diseases.

Substantial evidence now points to pernicious overactivity of normal neurotransmitter systems as a contributory mechanism in many instances of pathological neuronal degeneration. In particular, overstimulation of neuronal receptors for L-glutamate, the brain's most prevalent excitatory amino acid ("EAA") neurotransmitter, has been recognized as a causal or exacerbating factor in several acute neurological disorders, and has been proposed to underlie a number of chronic neurodegenerative diseases as well [Choi, D. W., *Neuron.*, 1:623 (1988); Choi, D. W., *Cerebrov. and Brain Metab. Rev.*, 2:105 (1990); Albers, G. W., et al., *Ann. Neurol.*, 25:398 (1989)]. Indeed, it is believed that glutamate neurotoxicity is involved in acute injury to the nervous system as observed with seizure, hypoxia, hypoglycemia, and trauma, as well as in chronic degenerative diseases such as Huntington's disease, olivopontocerebellar atrophy associated with glutamate dehydrogenase deficiency and decreased glutamate catabolism, amyotrophic lateral sclerosis/Parkinsonium-dementia, Parkinson's disease, and Alzheimer's disease [Choi, D. W., *Neuron*, 1:623–634 (1988); Choi, D. W., *Cereb. Brain Met.*, *Rev.* 2:105–147 (1990); Courtier et al., *Lancet*, 341:265–268 (1993); Appel, S. H., *Trends Neurosci.*, 16:3–5 (1993)].

In the mammalian brain, glutamate interacts with three major classes of receptors, i.e., N-methyl-D-aspartate ("NMDA") receptors, non-NMDA receptors and metabotropic receptors [Watkins, J. D., et al., *Trends Neurosci.*, 10:265 (1987); and Seeburg, *TIPS*, 141:297 (1993)]. While triggering distinctive postsynaptic responses, all three classes of glutamate receptors can act to increase the intracellular concentration of free $Ca^{2+}$ in nerve cells [A. B. MacDermott, *Nature* 321:519 (1986)]. Thus, binding of glutamate to the NMDA receptor opens a cation-selective channel that is markedly permeable to $Ca^{2+}$, leading to a large and rapid increase in intracellular $Ca^{2+}$. A subclass of non-NMDA receptors has been found to be linked to a Ca-permeable cation channel [Sommer, B., and Seeburg, P. H., *Trends Pharmacol. Sci.* 13:291–296 (1992)]. Although non-NMDA receptors are in most other instances linked to cation channels that largely exclude calcium, they can indirectly promote $Ca^{2+}$ entry into neurons by depolarizing the cell membrane, which in turn opens voltage-activated $Ca^{2+}$-channels. The so-called "metabotropic receptor", on the other hand, is not associated with an ion channel but can promote the release of $Ca^{2+}$ from intracellular stores via the second-messenger inositol triphosphate.

Irrespective of the triggering mechanism, prolonged elevation of cytosolic $Ca^{2+}$ is believed to be a key event in the initiation of neuronal destruction. Adverse consequences of elevated intracellular $Ca^{2+}$ include derangement of mitochondrial respiration, activation of $Ca^{2+}$-dependent proteases, lipases and endonucleases, free radical formation and lipid peroxidation of the cell membrane [Choi, D. W., *Neuron*, 1:623–624 (1988)].

The NMDA subtype of excitatory amino acid receptors is strongly involved in nerve cell death which occurs following brain or spinal chord ischemia. Upon the occurrence of ischemic brain insults such as stroke, heart attack or traumatic brain injury, an excessive release of endogenous glutamate occurs, resulting in the over-stimulation of NMDA receptors. Associated with the NMDA receptor is an ion channel. The recognition site, i.e., the NMDA receptor, is external to the ion channel. When glutamate interacts with the NMDA receptor, it causes the ion channel to open, thereby permitting a flow of cations across the cell membrane, e.g., $Ca^{2+}$ and $Na^+$ into the cell and $K^+$ out of the cell. It is believed that this flux of ions, especially the influx of $Ca^{2+}$ ions, caused by the interaction of glutamate with the NMDA receptor, plays an important role in nerve cell death [see, e.g., Rothman, S. M. and Olney, J. W., *Trends in Neurosci.*, 10(7):299–302 (1987)]. Additionally, excessive excitation of neurons occurs in epileptic seizures and it has been shown that over-activation of NMDA receptors contributes to the pathophysiology of epilepsy [(Porter, R. J., *Epilepsia*, 30(Suppl. 1):S29–S34 (1989); and Rogawski, M. A., et al., *Pharmacol. Rev.*, 42:224–286 (1990)].

Non-NMDA receptors constitute a broad category of postsynaptic receptor sites which, as is the case for NMDA receptors, are directly linked to ion channels. Specifically, the receptor sites are physically part of specific ion channel proteins. Non-NMDA receptors have been broadly characterized into two major subclasses based on compounds selective therefor: kainate receptors and AMPA/quisqualate receptors [see J. C. Watkins et al., *Trends Neurosci.*, 10:265 (1987)]. AMPA is an abbreviation for α-amino-3-hydroxyl-5-methyl-4-isoazole propionic acid. These subclasses may be categorized as "non-NMDA" receptors.

Compared to NMDA receptors, non-NMDA receptors have received less pharmacological scrutiny—the existing antagonists are all competitive— and in vivo research in this area has been hampered by the lack of drugs that cross the blood-brain barrier. Nonetheless, in vivo studies have clearly demonstrate that non-NMDA receptor agonists can also be as excitotoxic, although longer exposures can be required. In addition, evidence from animal studies and from human epidemiological studies suggests that excitotoxicity mediated by non-NMDA receptors may be clinically important in certain pathologies. [see M. D. Ginsberg et al., *Stroke*, 20:1627 (1989)].

One such disorder is global cerebral ischemia or hypoxia, as occurs following cardiac arrest, drowning, and carbon monoxide poisoning. Transient, severe interruption of the cerebral blood supply and/or interruption of the delivery of oxygen to the brain of animals causes a syndrome of selective neuronal necrosis, in which degeneration occurs among special populations of vulnerable neurons (including neocortical layers 3, 5 and 6, pyramidal cells in hippocampal zones CA1 and CA3, and small and medium sized striatal neurons). The time course of this degeneration is also regionally variable, and can range from a few hours (striatum) to several days (hippocampus).

NMDA antagonists generally have not proven highly effective in animal models of global ischemia; indeed, it has been suggested that positive results obtained using NMDA antagonists may largely be the artifactual result of induction of hypothermia rather that due to direct inhibition of NMDA receptor-linked Ca entry into brain neurons [Buchan, A. et al., *J. Neurosci.*, 11 (1991) 1049–1056]. In contrast, the competitive non-NMDA receptor antagonist 2,3-dihydroxy-6-nitro-7-sulfamoyl-benzo(F)quinoxaline ("NBQX") is dramatically effective in preventing delayed neuronal degeneration following transient forebrain ischemia in both gerbils and rats [M. J. Sheardown et al., *Science*, 247:571–574 (1990)].

At present, there is a critical need for effective treatments which limit the extent of nerve cell death following a stroke or traumatic brain injury. Recent advances in the understanding of the mechanisms underlying this nerve cell death have led to the hope that a drug treatment can be developed. Research and development efforts in this area have focussed on blocking the actions of glutamate that are mediated by the NMDA receptor-channel complex. Two approaches have been developed: competitive NMDA receptor antagonists [Choi D. W., *Cerebrov. Brain Metab. Rev.* 1:165–211 (1990); Watkins, J. C. and Olverman, H. J., *Trends Neurosci.*, 10:265–272 (1987)] and blockers of the ion channel of the NMDA receptor-channel complex [Meldrum, B., *Cerebrovascular Brain Metab. Rev.* 2:27–57 (1987); Choi, D. W., *Cerebrovascular Brain Metab. Rev.* 2:105–147 (1987); and Kemp, J. A. et al., *Trends Neurosci.*, 10:265–272 (1987)]. However, some toxicity with certain of the aforementioned agents has been reported has been reported [Olney, J. W. et al., *Science*, 244:1360–1362 (1989); Koek, W. and Colpaert, J., et al., *J. Pharmacol. Exp. Ther.*, 252:349–357 (1990)].

Blockers of neurotransmitter release, in particular blockers of the release of glutamate, have also received some attention as potential neuroprotective agents [see Meldrum, B., *Cerebrovascular and Brain Metab., Rev.* 2: 27–57 (1990); Dolphin, A. C. *Nature*, 316:148–150 (1985)); Evans, M. C. et al., *Neurosci. Lett.*, 83:287–292 (1987); Ault, B. and Wang, C. M., *Br. J. Pharmacol.*, 87:695–703 (1986); Kaneko, T., et al., *Arzneim-Forsch./Drug Res.*, 39:445–450 (1989); Malgouris, C., et al., *J. Neurosci.*, 9:3720–3727 (1989); Jimonet, P. et al. *BioOrgan. and Med. Chem. Lett.*, 983–988 (1993); Wahl, F. et al., *Eur. J. Pharmacol.*, 230:209–214 (1993); Koek, J. W. and Colpaert, F. C., *J. Pharmacol. Exp. Ther.*, 252:349–357 (1990); Kaneko, T. et al., *Arzneim.-Forsch./Drug Res.*, 39:445–450 (1989)]. Certain compounds said to inhibit glutamate release also have been reported to show anticonvulsant activity [Malgouris, C., et al., *J. Neurosci.*, 9: 3720– 3727 (1989); Miller, A. A., et al., in *New Anticonvulsant Drugs*, Meldrum, B. S. and Porter R. J. (eds), London: John Libbey, 165–177 (1986)].

Calcium antagonists acting at L-type Ca channels such as nimodipine have been reported to act both as cerebral vasodilators [Wong, M. C. W. et al., *Stroke*, 24:31–36 (1989)], and to block calcium entry into neurons [Scriabine, A., *Adv. Neurosurg., pp.* 173–179 (1990)]. Modest improvement in the outcome of stroke has been observed in clinical trials [Gelmers, H. J. et al., *N. Eng. J. Med.*, 318:203–207 (1988)]. While there are significant cardiovascular side effects, nimodipine appears less toxic in other respects than certain NMDA antagonists.

Antagonists of voltage-gated Na channels can exhibit neuroprotective properties. [Graham, S. H., et al., *J. Cereb. Blood Flow and Metab.*, 13:88–97 (1993), Meldrum, B. S., et al., *Brain Res.*, 593:1–6 and Stys, P. K., et al., *J. Neurosci.*, 12: 430–439 (1992)]. In stroke, sustained hypoxia in the "core region" results from occlusion of the blood supply by a clot. As hypoxia develops, ATP depletion leads to an inability of the Na, K-ATPase to maintain the ion gradients which generate the normal membrane potential of resting nerve cells. As the cell depolarizes and reaches the threshold for action potential firing, Na channels are activated. Stys et al. [Stys, et al., *J. Neurosci.*, 12: 430–439 (1992)] recently reported the development of Na channel hyperactivity in anoxia of central white matter and demonstrate in vitro the neuroprotective effect of the Na channel blockers tetrodotoxin (TTX) and saxitoxin (STX).

SUMMARY OF THE INVENTION

The present invention provides therapeutically useful substituted guanidine compounds, including compounds that modulate, particularly inhibit, the release of a neurotransmitter such as glutamate, and methods of treatment comprising such compounds. Preferred compounds of the invention modulate, particularly inhibit, neurotransmitter (e.g., glutamate) release from ischemic neuronal cells, especially mammalian cells such as human neuronal cells. The compounds of the invention are useful for a number of therapeutic applications, including treatment of those diseases that result from modulation of a particular neurotransmitter system and that can be counteracted by one or more of the substituted guanidines of the invention which act either on the same or another class of neurotransmitters, and treatment of a variety of disorders of the nervous system and cardiovascular system, and of endocrine function.

In a first aspect, the present invention provides N,N-disubstituted guanidines of Formula I:

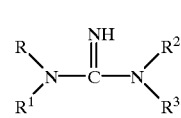

wherein:

R and $R^1$ are each independently substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted aminoalkyl having 1 to about 20 carbon atoms, substituted or unsubstituted alkylthio having from 1 to about 20 carbon atoms, substituted or unsubstituted alkylsulfinyl having from 1 to about 20 carbon atoms, substituted or unsubstituted carbocyclic aryl having at least about 5 ring atoms, substituted or unsubstituted aralkyl having at least about 5 ring atoms, or a substituted or unsubstituted heteroaromatic or heteroalicyclic group having from 1 to 3 rings, 3 to 8 ring members in each ring and from 1 to 3 hetero atoms, with at least one of R and $R^1$ being carbocyclic aryl, aralkyl, a heteroaromatic group or a heterocyclic group;

$R^2$ and $R^3$ each being independently selected from the group consisting of hydrogen, substituted and unsubstituted alkyl having from 1 to about 20 carbon atoms, substituted and unsubstituted alkoxy having from 1 to about 20 carbon atoms, substituted and unsubstituted alkylthio having from 1 to about 20 carbon atoms, substituted and unsubstituted alkylsulfinyl having from 1 to about 20 carbon atoms, substituted and unsubstituted alkylsulfonyl having from 1 to about 20 carbon atoms, and substituted and unsubstituted aminoalkyl; and pharmaceutically acceptable salts thereof.

A preferred group of compounds of Formula I are N,N-disubstituted compounds of the following Formula IA:

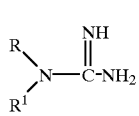

IA wherein R and $R^1$ are as defined above for Formula I, and pharmaceutically acceptable salts thereof.

A further preferred group of compounds of Formula I are compounds of the following Formula IB:

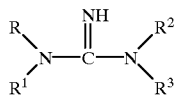

IB wherein R and $R^1$ are as defined above for Formula I, and $R^2$ and $R^3$ each being independently selected from the group consisting of hydrogen, substituted and substituted alkyl having from 1 to about 20 carbon atoms, substituted and unsubstituted alkoxy having from 1 to about 20 carbon atoms, substituted and unsubstituted alkylthio having from 1 to about 20 carbon atoms, substituted and unsubstituted alkylsulfinyl having from 1 to about 20 carbon atoms, substituted and unsubstituted alkylsulfonyl having from 1 to about 20 carbon atoms, and substituted and unsubstituted aminoalkyl, with at least one of $R^2$ and $R^3$ being other than hydrogen; and pharmaceutically acceptable salts thereof.

Preferred compounds of Formulas I, IA or IB include those compounds where at least one, or more preferably both, of R and $R^1$ is substituted or unsubstituted carbocyclic aryl or substituted or unsubstituted aralkyl or substituted or unsubstituted alkaryl. Preferred compounds of Formulas I, IA and IB include those compounds having substituents with 1 to about 6 carbon atoms, particularly $R^2$ and/or $R^3$ groups that have 1 to 6 carbon atoms. Particularly preferred $R^2$ and $R^3$ substituents of compounds of Formulas I, IA or IB include unsubstituted alkyl and heteroalkyl such as alkoxy, alkylthio, alkylsulfinyl, alkylsulfonyl and aminoalkyl. Preferred R and $R^1$ groups include substituted and unsubstituted acenaphthyl, phenyl, biphenyl, naphthyl, fluorenyl and benzyl, particularly alkyl-substituted and alkoxy-substituted phenyl and benzyl. Particularly preferred R and $R^1$ groups include straight and branched chain $C_{1-8}$-alkyl substituted phenyl and benzyl such as tert-butylphenyl, tert-butylbenzyl, sec-butylphenyl, sec-butylbenzyl, n-butylphenyl, n-butylbenzyl, iso-butylphenyl, iso-butylbenzyl, pentylphenyl, pentylbenzyl, hexylphenyl, hexylbenzyl and the like; straight and branched chain $C_{1-8}$-alkoxy (including haloalkoxy, i.e. alkoxy substituted by F, Cl, Br and/or I) substituted phenyl and benzyl such as butoxyphenyl, butoxybenzyl, pentoxyphenyl, pentoxybenzyl, hexoxyphenyl, hexoxybenzyl, trifluoromethoxyphenyl, trifluorobenzyl, fluoro and the like; alkaryl (including alkoxyaryl) substituted phenyl and benzyl, particularly substituted and unsubstituted benzyl and benzyloxy (especially —$OCH_2C_6H_5$). Cycloalkyl and aryl (particularly carbocyclic aryl) such as substituted phenyl, benzyl and naphthyl are also preferred R and $R^1$ groups such as biphenyl, phenylbenzyl (i.e. —$CH_2C_6H_4C_6H_5$), cyclohexylphenyl, cyclohexylbenzyl and the like. Halo (i.e., F, Cl, Br and/or I) substituted R and $R^1$ groups are also preferred including halo-substituted phenyl, naphthyl and benzyl.

In another aspect, the invention provides compounds of the following Formula II:

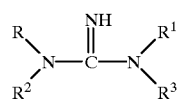

II wherein

R is selected from the group of fluorenyl, phenanthracenyl, anthracenyl and fluoranthenyl;

$R^1$ is substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted aminoalkyl having 1 to about 20 carbon atoms, substituted or unsubstituted alkylthio having from 1 to about 20 carbon atoms, substituted or unsubstituted alkylsulfinyl having from 1 to about 20 carbon atoms, substituted or unsubstituted alkylsulfonyl having from 1 to about 20 carbon atoms, substituted or unsubstituted carbocyclic aryl having at least about 5 ring atoms, substituted or unsubstituted aralkyl having at least about 5 ring atoms, or a substituted or unsubstituted heteroaromatic or heteroalicyclic group having 1 to 3 rings, 3 to 8 ring members in each ring and 1 to 3 heteroatoms;

$R^2$ and $R^3$ are each independently hydrogen or a group as defined for $R^1$ above; and pharmaceutically acceptable salts thereof.

Preferred compounds of Formula II include N,N'-disubstituted compounds, i.e. where $R^2$ and $R^3$ are each hydrogen, as well as tri- and tetra-substituted compounds where one or both of $R^2$ and $R^3$ are other than hydrogen. Preferred $R^1$ groups include cycloalkyl, particularly adamantyl, and carbocyclic aryl, particularly substituted or unsubstituted phenyl, naphthyl or acenaphthyl, more preferably substituted or unsubstituted phenyl or naphthyl, such as alkyl or alkoxy substituted phenyl or naphthyl. Alkyl such as methyl, ethyl or propyl is a preferred $R^2$ or $R^3$ group.

In a further aspect, the invention provides compounds of the following Formula III:

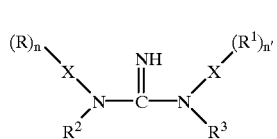

III wherein R and $R^1$ are each independently substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted aryloxy having from 6 to about 20 carbon atoms, substituted or unsubstituted aralkoxy having from 6 to about 20 carbon atoms, substituted or unsubstituted aminoalkyl having 1 to about 20 carbon atoms, substituted or unsubstituted alkylthio having from 1 to about 20 carbon atoms, substituted or unsubstituted alkylsulfinyl having from 1 to about 20 carbon atoms, substituted or unsubstituted alkylsulfonyl having 1 to about 20 carbon atoms, substituted or unsubstituted carbocyclic aryl having at least 5 ring atoms, substituted or unsubstituted aralkyl having at least 5 ring atoms, or a substituted or unsubstituted heteroaromatic or heteroalicyclic group having 1 to 3 rings, 3 to 8 ring members in each ring and 1 to 3 heteroatoms;

$R^2$ and $R^3$ are each independently hydrogen or a group as defined for R and $R^1$ above, and preferably are each substituted or unsubstituted alkyl, alkenyl, alkynyl, alkoxy, aminoalkyl, alkylthio or alkylsulfinyl; or $R^1$ and $R^3$ together form a ring having 5 or more ring members;

n and n' independently are each equal to 1, 2, or 3;

X and X' are each independently a chemical bond (i.e., a bond between the guanidine nitrogen and R or $R^1$), substituted or unsubstituted alkylene having from 1 to about 8 carbon atoms, substituted or unsubstituted alkenylene having from 2 to about 8 carbon atoms, or substituted or unsubstituted alkynylene having from 2 to about 8 carbon atoms, substituted or unsubstituted heteroalkylene having from 1 to about 8 carbon atoms, substituted or unsubstituted heteroalkenylene having 2 to about 8 carbon atoms, and substituted or unsubstituted heteroalkynylene having from 2 to about 8 carbon atoms, with at least one X and X' being other than a bond; and pharmaceutically acceptable salts thereof.

Preferred compounds of Formula III include those where X is substituted or unsubstituted alkylene or alkenylene having 1 to about 3 carbon atoms, particularly where X is a substituted or unsubstituted alkylene having 1 to about 6 carbon atoms, more preferably 1 to about 4 carbon atoms, as specified by the following Formula IIIA:

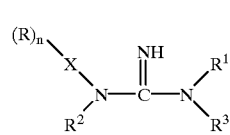

IIIA wherein the groups R, $R^1$, $R^2$ and $R^3$ are as defined above for Formula III, and the value n is equal to 1, 2 or 3; and pharmaceutically acceptable salts thereof.

Preferred compounds of Formula III include those where R and $R^1$ together form a ring having 5 or more ring atoms, either with the guanidine nitrogen as the sole hetero atom or with one or more other N, O or S atoms as ring members, typically just one other N, O or S ring atom in addition to the guanidine N. Generally preferred is where R and $R^1$ together form a ring having 5–7 ring atoms, e.g., forming the following substituted or unsubstituted rings: morpholinyl, 1,2,3,4-tetrahydroisoquinolinyl, thiomorpholinyl, pyrrolidinyl, piperidinyl and tetrahydroquinolinyl. Preferred substituents of such rings include e.g. $C_{1-8}$alkyl, $C_{1-8}$alkoxy and substituted and unsubstituted alkaryl, particularly substituted and unsubstituted benzyl.

Particularly preferred such compounds of Formula III are those of the following Formula IIIB:

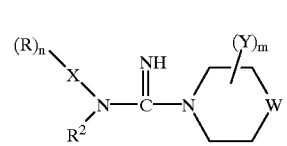

IIIB wherein R and $R^2$ of said formula are each independently substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted aryloxy having from 6 to about 20 carbon atoms, substituted or unsubstituted aralkoxy having from 6 to about 20 carbon atoms, substituted or unsubstituted aminoalkyl having 1 to about 20 carbon atoms, substituted or unsubstituted alkylthio having from 1 to about 20 carbon atoms, substituted or unsubstituted alkylsulfinyl having from 1 to about 20 carbon atoms, substituted or unsubstituted alkylsulfonyl having 1 to about 20 carbon atoms, substituted or unsubstituted carbocyclic aryl having at least 5 ring atoms, substituted or unsubstituted aralkyl having at least 5 ring atoms, or a substituted or unsubstituted heteroaromatic or heteroalicyclic group having 1 to 3 rings, 3 to 8 ring members in each ring and 1 to 3 heteroatoms;

n is 1, 2, or 3, and preferably is 1 or 2, more is preferably 1; W is a carbon atom, or N, O or S; m is an integer of from 0 to 5, and preferably is 1, 2 or 3, more preferably 0, 1 or 2.

X is substituted or unsubstituted alkylene having from 1 to about 8 carbon atoms, substituted or unsubstituted alkenylene having from 2 to about 8 carbon atoms, or substituted or unsubstituted alkynylene having from 2 to about 8 carbon atoms, substituted or unsubstituted heteroalkylene having from 1 to about 8 carbon atoms, substituted or unsubstituted heteroalkenylene having 2 to about 8 carbon atoms, and substituted or unsubstituted heteroalkynylene having from 2 to about 8 carbon atoms, and preferably X is substituted or unsubstituted alkylene, particularly alkylene having 1 to 2 carbon atoms;

each Y substituent is independently halogen, substituted or unsubstituted alkyl having 1 to about 10 carbon atoms, substituted or unsubstituted alkenyl having 2 to about 10 carbon atoms, unsubstituted alkynyl having 2 to about 10 carbon atoms, substituted or unsubstituted alkoxy having from 1 to about 10 carbon atoms, substituted or unsubstituted alkylthio having 1 to about 10 carbon atoms, substituted or unsubstituted aminoalkyl having from 1 to about 10 carbon atoms, or substituted or unsubstituted carbocyclic aryl having about 6 or more ring members; and pharmaceutically acceptable salts thereof.

Particularly preferred compounds of Formula IIIB are those where R and $R_2$ are each independently aryl, particularly substituted or unsubstituted carbocyclic aryl such as substituted or unsubstituted phenyl, substituted or unsubstituted naphthyl or substituted or unsubstituted acenaphthyl.

Especially preferred compounds of Formula IIIB are those where R and $R_2$ are each substituted or substituted phenyl, such as sec-butylphenyl or tert-butylphenyl, particularly para-sec-butylphenyl or para-tert-butylphenyl, n is 1 and X is alkylene of one or two carbons. Particularly preferred are compounds of the following Formula IIIBB:

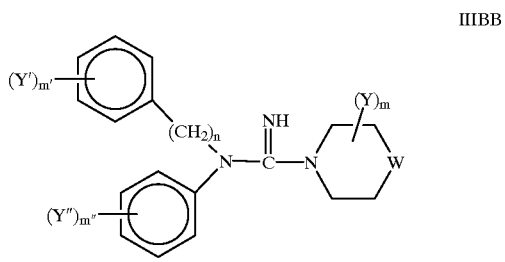

IIIBB wherein W is a carbon atom, or N, O or S;

each Y, each Y' and each Y" is each independently halogen, substituted or unsubstituted alkyl having 1 to about 10 carbon atoms, substituted or unsubstituted alkenyl having 2 to about 10 carbon atoms, unsubstituted alkynyl having 2 to about 10 carbon atoms, substituted or unsubstituted alkoxy having from 1 to about 10 carbon atoms, substituted or unsubstituted alkylthio having 1 to about 10 carbon atoms, substituted or unsubstituted aminoalkyl having from 1 to about 10 carbon atoms, or substituted or unsubstituted carbocyclic aryl having about 6 or more ring members; n is 1 or 2, and each m, m' and m" is independently an integer of from 0 to 5, and preferably is each m, m' and m" is independently 0, 1, 2 or 3, more preferably 0, 1 or 2; and pharmaceutically acceptable salts thereof. Generally preferred compounds of Formulas IIIB and IIIBB are those where a Y group is bonded to the W ring member, particularly where W and Y together form a substituted carbon atom or N atom such as a $C_{1-8}$alkyl or $C_{1-8}$alkoxy substituted carbon or nitrogen ring atom. As will be of course understood by those skilled in the art, where m, m' or m" is 0, the corresponding ring would be "fully" hydrogen-substituted. Specifically preferred compounds of Formula IIIBB include N-(4-butoxyphenyl)-N-(4-tert-butylbenzyl)-N'-(4-piperidinyl)guanidine; N-(4-butoxyphenyl)-N-(4-tert-butylbenzyl)-N'-(4-benzylpiperidinyl)guanidine; N-(4-butoxyphenyl)-N-(4-tert-butylbenzyl)-N'-(4-morpholinyl) guanidine; and N-(4-butoxyphenyl)-N-(4-tert-butylbenzyl)-N'-(3,5-dimethyl-4-morpholinyl)guanidine.

A further group of preferred compounds of Formula III are defined the same as Formulas IIIB and IIIBB above, but where two Y substituents are taken together to form an aryl or alicyclic fused ring. Generally preferred is where the fused ring is a heterocyclic or carbocyclic aryl, particularly phenyl, naphthyl, 1,2,3,6-tetrahydroquinolinyl, thiomorpholinyl, pyrolindinyl, piperazinyl and the like, or a cycloalkyl such as cyclohexyl. A specifically preferred compound is N-(4-sec-butylphenyl)-N-(4-tert-butylbenzyl)-N'-(1,2,3,4-tetrahydroisoquinolinyl)guanidine.

Preferred compounds of Formulas III, IIIA and IIIB include those where R and/or $R^1$ is substituted or unsubstituted carbocyclic aryl, particularly substituted or unsubstituted phenyl, substituted or unsubstituted naphthyl or substituted or unsubstituted acenaphthyl. Particularly preferred are compounds of Formula III and IIIA where R, $R^1$ and $R^2$ are each substituted or unsubstituted carbocyclic aryl, particularly substituted or unsubstituted phenyl, substituted or unsubstituted naphthyl or substituted or unsubstituted acenaphthyl. Especially preferred are compounds of Formula IIIA where R, $R^1$ and $R^2$ are each such a substituted or unsubstituted carbocyclic aryl, $R_3$ is hydrogen or $C_{1-4}$ alkyl such as methyl or ethyl, and n is 1 or 2. Of those especially preferred compounds one or more of R, $R^1$ and $R^2$ is preferably substituted or unsubstituted phenyl e.g. $C_{1-8}$alkyl-substituted phenyl such as sec-butylphenyl tert-butylphenyl and the like, halo-substituted phenyl, $C_{1-8}$alkoxysubstituted phenyl such as butoxyphenyl or pentoxyphenyl or carbocyclic alkaryloxy-substituted phenyl such benzyloxyphenyl.

Preferred compounds of Formula III and IIIA also include N,N'-disubstituted compounds, i.e. where $R^2$ and $R^3$ are each hydrogen, as well as tri- and tetra-substituted compounds where one or both of $R^2$ and $R^3$ are other than hydrogen. Preferred $R^2$ and $R^3$ groups include alkyl such as methyl, ethyl or propyl, and substituted alkyl, particularly haloalkyl such as $C_1$–$C_6$ or $C_1$–$C_4$ alkyl substituted by one or more F, Cl or Br. Alkylene and heteroalkylene are preferred X or X' groups, including those heteroalkylene groups containing 1 or 2 N, O, or S atoms as chain members. Particularly preferred X and X' groups of compounds of Formulas III, IIIA and IIIB include —$CH_2$—, —$CH_2CH_2$—, —$CH(CH_3)CH_2$— and —$CH_2CH(CH_3)$—. Preferred compounds of Formulas III and IIIA include those where each R and $R^1$ group of a compound is bonded to the same carbon atom of the X or X' chain.

In a further aspect, compounds of the following Formula IV are provided:

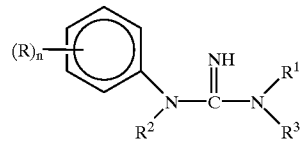

IV wherein each R is independently halo, hydroxy, amino, nitro, substituted or unsubstituted alkyl having from 3 to about 10 carbon atoms and preferably from 4 to about 10 carbon atoms, substituted or unsubstituted alkoxy, substituted or unsubstituted aryloxy, substituted or unsubstituted aralkoxy, substituted or unsubstituted aminoalkyl, substituted or unsubstituted alkylthio, substituted or unsubstituted alkylsulfinyl, substituted or unsubstituted alkylsulfonyl, substituted or unsubstituted alkenyl having 3 to about 10 carbon atoms, or substituted or unsubstituted alkynyl having 3 to about 10 carbon atoms;

n is an integer of from 1 to 5, preferably from 1 to 3;

$R^1$ is substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted aminoalkyl having 1 to about 20 carbon atoms, substituted or unsubstituted aryloxy having from 6 to about 20 carbon atoms, substituted or unsubstituted alkylthio having from 1 to about 20 carbon atoms, substituted or unsubstituted alkylsulfinyl having from 1 to about 20 carbon atoms, substituted or unsubstituted alkylsulfonyl having 1 to about 20 carbon atoms, substituted or unsubstituted carbocyclic aryl having at least 5 ring atoms, substituted or unsubstituted aralkyl having at least 5 ring atoms, or a substituted or unsubstituted heteroaromatic or heteroalicyclic group having 1 to 3 rings, 3 to 8 ring members in each ring and 1 to 3 heteroatoms;

$R^2$ and $R^3$ are each independently hydrogen or a group as defined for $R^1$ above; or $R^2$ and $R^3$ are taken together to form a substituted or unsubstituted alkylene linkage of from 2 to about 6 carbon atoms; and pharmaceutically acceptable salts thereof.

Preferred compounds of Formula IV include those where one or more R substituents is a branched group such as sec-butyl or tert-butyl, or where one or more R substituent is substituted or unsubstituted aralkoxy, particularly substituted or unsubstituted benzyloxy. The value n is preferably 1, 2 or 3. Para-substitution and meta-substitution of the phenyl group by R substituent(s) is preferred. Preferred compounds of Formula IV include N,N'-disubstituted compounds, i.e. where $R^2$ and $R^3$ are each hydrogen, as well as tri- and tetra-substituted compounds where one or both of $R^2$ and $R^3$ are other than hydrogen. Alkyl such as methyl, ethyl or propyl is a preferred $R^2$ or $R^3$ group. Substituted or unsubstituted aryl such as substituted or unsubstituted phenyl or benzyl are preferred $R^1$ groups.

A particularly preferred group of compounds of Formula IV are those of the following Formula IV(A):

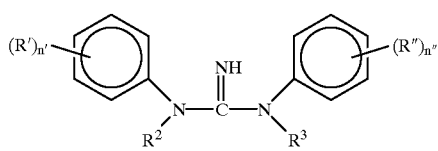

wherein each R' and R" are each independepently selected from the same group as defined for R of Formula IV above; $R^2$ and $R^3$ are defined the same as in Formula IV above; and n' and n" are each an integer of 1 to 5, and preferably are each 1 or 2; and pharmaceutically acceptable salts thereof. It is preferred that n' and n" are each 1, and R' and R" are each a meta or para substituent, more preferably each being a para substituent. It is further preferred that R' and R" are each branched substituents such as tert-butyl, sec-butyl, iso-butyl, iso-pentyl and the like. Preferably $R^2$ and $R^3$ are hydrogen or $C_{1-4}$alkyl such as methyl or ethyl. Specifically preferred compounds of Formula IV(A) include N,N'-bis(3-sec-butylphenyl)guanidine and N,N'-bis(4-tert-butylphenyl)guanidine. In another aspect, the invention provides compounds of said Formula IV(A), particularly for use for the methods of treatment disclosed herein, but where excluded from said Formula IV(A) are the compounds of N,N'-bis(4-neopentylphenyl)guanidine, N,N'-bis(4-t-butylphenyl)guanidine, N,N'-bis(4-n-butylphenyl)guanidine, and N,N'-bis(4-cyclohexylphenyl)guanidine.

Preferred compounds of Formula IV, particularly for use in methods of treatment of the invention, also include those compounds wherein $R^2$ and $R^3$ are taken together to form a substituted or unsubstituted alkylene linkage of from 3 to about 6 carbon atoms, particularly compounds with an alkylene linkage of 3 carbon atoms as represented of the following Formula IV(B):

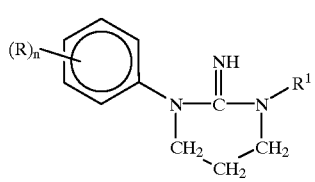

wherein R, $R^1$ and n are each the same as defined above for Formula IV, and pharmaceutically acceptable salts thereof. Preferred $R^1$ groups of compounds of Formula IV(B) include substituted and unsubstituted alkaryl, particularly substituted and unsubstituted benzyl, and substituted and unsubstituted carbocyclic aryl, particularly substituted and unsubstituted phenyl, substituted and unsubstituted naphthyl and substituted and unsubstituted acenaphthyl. Preferred substituents of such substituted phenyl, naphthyl or acenaphthyl $R^1$ groups include $C_{1-8}$alkyl, $C_{1-8}$alkoxy, $C_{1-8}$(mono- or dialkyl)amine, alkoxyaryland carbocyclic aryloxy, such as sec-butyl, tert-butyl, hexyl, butyoxy, phenoxy, benzyloxy, and the like.

Specifically, particularly for use in methods of treatment of the invention, are compounds of the above Formula IV(B) where $R^1$ is a substituted or unsubstituted phenyl, as represented by the following Formula IV(BB):

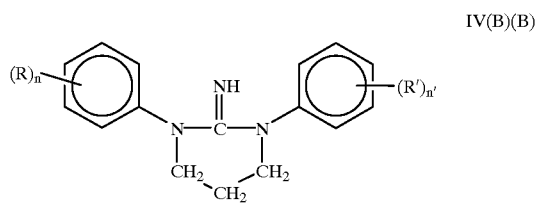

where each R and R' are each independently halo, hydroxy, amino, nitro, substituted or unsubstituted alkyl having from 3 to about 10 carbon atoms and preferably from 4 to about 10 carbon atoms, substituted or unsubstituted alkoxy, substituted or unsubstituted aryloxy, substituted or unsubstituted aralkoxy, substituted or unsubstituted aminoalkyl, substituted or unsubstituted alkylthio, substituted or unsubstituted alkylsulfinyl, substituted or unsubstituted alkylsulfonyl, substituted or unsubstituted alkenyl having 3 to about 10 carbon atoms, or substituted or unsubstituted alkynyl having 3 to about 10 carbon atoms; and each n and n' is independently an integer of from 0 to 5, preferably from 1 to 5, more preferably 1 to 2 or 3. Particularly preferred is where each n and n' is 1. Preferred compounds of Formula IV(BB) include those where one or more R or R' substituents is a branched group such as a branched alkyl group e.g. sec-butyl or tert-butyl, or where one or more R substituent is substituted or unsubstituted aralkoxy, particularly substituted or unsubstituted benzyloxy. Para-substitution and meta-substitution of the phenyl group by R and R' substituent(s) is typically preferred. Particularly preferred is where n and n' are each 1, and R and R' are each para substituents. Preferred R and R' substituents include alkoxy and alkoxyaryl, such as butoxy, pentoxy, hexoxy, substituted and unsubstituted benzyloxy and the like. Specifically preferred compounds of Formula IV(BB) include N,N'-bis-(alkylphenyl)-2-iminopyrimidazolidine including N,N'-bis-(butylphenyl)-2-iminopyrimidazolidine, N,N'-bis-(pentylphenyl)-2-iminopyrimidazolidine, and N,N'-bis-(hexylphenyl)-2-iminopyrimidazolidine.

The invention also includes compounds of Formulas IV(B) or IV(BB) where two R substituents or two R' substituents together form a ring fused to the phenyl ring. Preferred fused rings have 5 to about 7 or 8 ring members and may be a carbocyclic aryl or saturated carbon ring, or a heteroaromatic or heteroalicyclic ring having 1 or 2 N, O or S atoms. Exemplary fused rings include e.g. tetralinyl, indane, or a saturated six carbon ring to form a tetralinyl fused ring.

In another aspect, acenaphthyl-substituted guanidines of the following Formula V are provided:

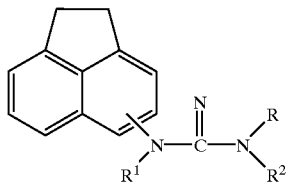

V wherein:

R is substituted or unsubstituted heteroaromatic containing 1–3 rings, 3 to 8 ring members in each ring and 1–3 heteroatoms;

$R^1$ and $R^2$ are each independently hydrogen, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted aminoalkyl having from 1 to about 20 carbon atoms, substituted or unsubstituted alkylthio having from 1 to about 20 carbon atoms, substituted or unsubstituted alkylsulfinyl having from 1 to about 20 carbon atoms, substituted or unsubstituted alkylsulfonyl having from 1 to about 20 carbon atoms, substituted or unsubstituted carbocyclic aryl having at least 5 ring atoms, substituted or unsubstituted aralkyl having at least 5 ring atoms, or a substituted or unsubstituted heteroaromatic or heteroalicyclic group having 1 to 3 rings, 3 to 8 ring members in each ring and 1 to 3 heteroatoms;

and pharmaceutically acceptable salts thereof.

Preferred R groups of Formula V include 1,2,3,4,-tetrahydroquinolinyl, indolinyl, piperonyl, benz[cd]indolinyl and [benz[cd]indo-2[1H]-one. The above depicted acenaphthyl group preferably is substituted by the guanidine nitrogen at the 3-position or 5-position. Preferred compounds of Formula V include N,N'-disubstituted compounds, i.e. where $R^1$ and $R^2$ are each hydrogen, as well as tri- and tetra-substituted compounds where one or both of $R^1$ and $R^2$ are other than hydrogen. Alkyl such as methyl, ethyl or propyl is a preferred $R^1$ and $R^2$ group of compounds of Formula V.

At least some compounds of the invention may exist as any one of a number of tautomeric forms. Each of these tautomeric forms are within the scope of the invention, including as defined by the formulas specified herein.

The present invention includes methods for treatment and/or prophylaxis of neurological conditions such as epilepsy, neurodegenerative conditions and/or nerve cell death resulting from, e.g., hypoxia, hypoglycemia, brain or spinal chord ischemia, brain or spinal chord trauma, stroke, heart attack, drowning or carbon monoxide poisoning. In this regard, compound of the invention are particularly useful to administer to mammals, particularly humans, susceptible or suffering from stroke or heart attack. Compounds of the invention also are useful to treat and/or prevent various neurodegenerative diseases such as Parkinson's disease, Huntington's disease, Amyotrophic Lateral Sclerosis, Alzheimer's disease, Down's Syndrome, Korsakoff's disease, olivopontocerebellar atrophy, HIV-induced dementia and blindness or multi-infarct dementia. Compounds of the invention also may be used to treat anxiety, e.g. by administration to subjects susceptible to generalized anxiety disorder. Compounds of the invention will have particular utility for treatment of global cerebral ischemia as may occur following cardiac arrest, drowning and carbon monoxide poisoning. Compounds of the invention also may be used to treat other disorders of the nervous system, disorders of the cardiovascular system such as hypertension, cardiac arrhythmias or angina pectoris, endocrine disorders such as acromegaly and diabetes insipidus, as well as use for treatment of chronic pain and as a local anesthetic. Compounds of the invention will have further utility for the treatment of those diseases in which the pathophysiology of the disorder involves excessive otherwise inappropriate (e.g., hypersecretory) cellular secretion, e.g., secretion of an endogenous substance such as a catecholamine, a hormone or a growth factor. Exemplary diseases are specifically discussed infra. Compounds of the invention also will have utility for the treatment of those diseases in which the pathophysiology of the disorder involves excessive or otherwise inappropriate (e.g., hypersecretory) cellular secretion, e.g., secretion of an endogenous substance such as a catecholamine, a hormone or a growth factor. The methods of treatment of the invention (which includes prophylactic therapy) generally comprise administration of a therapeutically effective amount of one or more compounds of the invention to an animal, including a mammal, particularly a human.

Further provided are diagnostic methods comprising use of the compounds of the invention. More specifically, a compound of the invention can be suitably labelled such as by radiolabelling a compound with $^{125}I$, tritium, $^{32}P$, $^9Tc$, or the like, preferably $^{125}I$. The labelled compound can be administered to a subject such as a human and the subject imaged for a disease or disorder involving ion-channel activity such as stroke.

The invention also provides pharmaceutical compositions that comprise one or more compounds of the invention and a suitable carrier.

DETAILED DESCRIPTION OF THE INVENTION

It has been found that compounds of the invention have the ability to modulate, i.e. inhibit or potentiate the release of neurotransmitter(s), or to decrease or lengthen the time course of release of neurotransmitter(s), from neuronal tissue. It has thus been found that the compounds will have utility to treat or prevent those pathophysiologic conditions which result from excessive or inadequate release of neurotransmitters. It is thought that substituted guanidines of the invention mediate the inhibition of neurotransmitter release by blocking presynaptic calcium channels and/or sodium channels. Accordingly, the invention provides methods for blockage of voltage-activated calcium channels or sodium channels of neuronal cells, particularly mammalian cells such as human neuronal cells, comprising the administration to the cells of an effective amount of a compound of the invention, particularly such administration to a mammal in need of such treatment. By such blockage of calcium channels and/or sodium channels of neuronal cells, conditions associated with excessive endogenous neurotransmitter release can be treated.

More particularly, some disorders such as neuronal damage in stroke may be alleviated by inhibiting the release of excitatory amino acids such as glutamate. Some disorders such as depression may be alleviated by inhibiting the release of inhibitory neurotransmitters such as gamma-aminobutyric acid. Further and without wishing to be bound by theory, inhibiting the release of an excitatory neurotransmitter such as glutamate by administration of a compound of the invention may indirectly potentiate the release or subsequent actions of an inhibitory transmitter such as gamma-aminobutyric acid, and thus the compound of the invention may treat disorders known to be alleviated by more direct potentiation of inhibitory neurotransmission, e.g., anxiety or insomnia.

Compounds of the invention may be considered effective inhibitors of neurotransmitter release if the compound causes at least about a 50% inhibition of neurotransmitter release, such as release of glutamate, at a concentration of about 100 $\mu$M according to the protocol disclosed in Example 146 infra. More preferably the compound will cause at least about a 50% inhibition of release of a neurotransmitter, such as glutamate, at a concentration of about 30 $\mu$m according to the protocol disclosed in Example 146 infra. As used herein, the phrase "high inhibition of glutamate release" indicates that the specified compound(s) will cause at least 50% inhibition of glutamate release at a concentration of about 100 $\mu$M according to the protocol disclosed in Example 146 infra.

Compounds of the invention may modulate release of neurotransmitters that include glutamate, dopamine, GABA ($\delta$-amino butyric acid), norepinephrine, glycine, aspartate, serotonin, acetylcholine, adenosine triphosphate and epinephrine, particularly glutamate. Compounds of the invention also may modulate release of peptides such as tachykinins, including substance P and substance k, enkephalins, luteinizing hormone-releasing hormone (LHRH) or derivatives thereof (see Harrington's Principles of Internal Medicine, 1705 (McGraw Hill 1987)), bombesin, cholecystokinin, neuropeptide Y, dynorphin, gastrin-releasing hormone (GRH), neurotensin, somatostatin, and vasoactive intestinal peptide (VIP).

Specifically, compounds of the invention show significant ability to block depolarization-stimulated, calcium-dependent glutamate release from brian synaptosomes, when tested by the rapid superfusion method described in Example 146, infra. Said method identifies compounds that act to block voltage-activated presynaptic Ca channels in nerve terminals, but may also identify compounds that block glutamate release by interfering with other processes involved in the control of Ca-dependent glutamate release. Compounds of the invention have demonstrated significant ($\geqq$50%) attenuation of glutamate release at concentrations of 10 $\mu$M or less, and many are effective at concentrations at or below 3 $\mu$M. See, e.g., Table I of Example 146, infra. Moreover, these compounds of the invention exhibit relatively low binding affinity for the ion channel of the NMDA subclass of glutamate receptors and the di-tolyl guanidine (DTG) binding site associated with the sigma receptor. This indicates that compounds of the invention have a clearly distinct therapeutic mechanism of action relative to that of known compounds which exhibit high affinity for either the ion channel of the NMDA subclass of glutamate receptors, and/or the DTG binding site of sigma receptors.

More particularly, a number of preferred compounds of the inventtion, including compounds of Formula IV and IV(A), will exhibit high inhibition of glutamate release (as that phrase is defined to mean above), but relatively low affinity for the PCP receptor, specifically an $IC_{50}$ of 5 to 100 $\mu$M or more in a typical PCP receptor assay as described in U.S. Pat. No. 4,906,779 (see columns 10–11). A number of preferred compounds of the invention also will exhibit high inhibition of glutamate release, but relatively low affinity for the sigma receptor in a typical sigma receptor binding assay such as the assay disclosed in Weber et al., Proc. Natl. Acad. Sci. (USA), 83:8784–8788 (1986), specifically an $IC_{50}$ of 10–200 $\mu$M or more in the DTG sigma binding assay disclosed in Weber et al., Proc. Natl. Acad. Sci. (USA), 83:8784–8788 (1986). As used herein, the phrase "low affinity to the NMDA receptor" is intended to mean the specified compound(s) exhibits an $IC_{50}$ of 5 to 100 $\mu$M or greater in said PCP receptor assay described in U.S. Pat. No. 4,906,779; and the term "low affinity to the sigma receptor" is intended to mean the specified compounds) exhibits an $IC_{50}$ of 10–200 $\mu$M or greater in the DTG sigma binding assay disclosed in Weber et al., Proc. Nat]. Acad. Sci. (USA), 83:8784–8788 (1986).

The preferred mechanism which underlies the ability of compounds of the invention to block neurotransmitter release in vivo is blockade of voltage-activated Na channels and/or Ca channels which regulate neurotransmitter release [McBurney et al., *J. Neurotrauma,* 9, Suppl. 2:S531–S543 (1992); Kattragadda, S. et al., *Abs. Soc. for NeuroSci. Abs.,* 18:436 (1992)]. Examples 146–148 below describe the ability of compounds of the invention to block said voltage-activated Na and Ca channels, providing further indication that compounds of the invention will effectively block release of a variety of neurotransmitters upon administration of the compounds to a mammal including a human.

Secretion of a variety of substances from non-neuronal secretory cells occurs by a process of Ca-dependent exocytosis closely resembling the mechanism of Ca-dependent neurotransmitter release [Rubin, R. P., *Pharmacol. Rev.,* 22:389–428 (1970)]. Examples of this include release of norepinephrine from adrenal chromaffin cells [Landsberg, L. et al., *Harrington's Principles of Internal Medicine,* 11 th Ed., eds., New York, McGraw-Hill, pp.358–370 (1987); Neher, E. et al., *Neuron,* 10:21–30 (1993)], secretion of peptide hormones from the pituitary [Tse et al., *Science,* 260:82–84 (1993); Chang, J. P. et al., *Endocrinology,* 123:87–94 (1988)], secretion of digestive enzymes from pancreatic acinar cells [Muallem, S., *Ann. Rev. Physiol.,* 51:83–105 (1989)], and secretion of insulin from pancreatic beta cells [Larner, J., *The Pharmacological Basis of Therapeutics,* 7th Ed., eds., New York, MacMillan, pp. 1490–1503 (1985)]. The voltage-activated Ca channels that play a major role in governing said processes resemble those that govern neurotransmitter release, in terms of structure, pharmacology, and mechanism [Bean, B. P., *Ann. Rev. Physiol.* 51:367–384 (1989); Hess, P., *Ann. Rev. Neurosci.* 13:337–56 (1989); Cohen, C. J. et al., *J. Physiol.,* 387:195–225 (1987)]. Accordingly the ability of compounds of the invention to block neurotransmitter release as described in Example 146, infra and the ability of said compounds to block the activity of voltage-activated Ca channels described in Examples 147 and 148, infra, constitutes strong evidence that compounds of the invention will be effective inhibitors of exocytotic secretion of a variety of substances from a variety of non-neuronal cells. In particular, Example 148 demonstrates the ability of compounds of the invention to block Ca channels in GH4C1 clonal pituitary cells. Said pituitary cells secrete prolactin and growth hormone [Tashjian, A. H. *Meth. Enyzmol.,* 58:527–535, Acad. Press, N.Y. (1979)]. Block of voltage-activated Ca channels of pituitary GH4C1 cells inhibits secretion of said peptides [Tan, K. N. et al., *J. Biol. Chem.,* 259:418–426 (1984)]. Therefore, the results disclosed in Example 148 indicate compounds of the invention can function as effective antisecretory agents.

Example 147 infra, describes the ability of a subset of the compounds of the invention to block the presynaptic voltage-activated Ca channels which regulate release of neurotransmitters from mammalian brain synaptosomes.

Said presynaptic Ca channels are structurally and functionally related, and in some instances are identical, to Ca channels found in the cell bodies of neurons in the brain, elsewhere in the central nervous system, and in the peripheral nervous system [Zhang, J. F. et al., *Neuropharmacol.*, 32:1075–1088 (1993); Snutch, T. P. et al., *Curr. Opin. Neurobiol.*, 2:247–253 (1992)]. Therefore, the results disclosed in Example 147 indicate the general ability of compounds of the invention to block neuronal Ca channels.

Example 149 infra, describes the ability of a subset of the compounds of the invention to block Type II (alias $R_{II}$) voltage-activated Na channels, which are identical or closely related to the presynaptic and axonal voltage-activated Na channels which also govern release of neurotransmitters from mammalian brain synaptosomes [Westenbrook et al. *Neuron*, 3:695–704 (1989); Catterall, W. A., *Physiolog. Rev.*, 72:S15–S48 (1992)]. Said presynaptic and axonal Type II Na channels are structurally and functionally similar, and in some instances are identical, to Na channels found in the cell bodies of neurons in the brain; elsewhere in the central nervous system; the peripheral nervous system; the cardiac conduction system comprising the Purkinje cell network and the atrial bundle branches; and cardiac, skeletal, and smooth muscle cells [Catterall, W. A., ibid.; Trimmer, J. S. et al., *Ann. Rev. Physiol.*, 51:401–418 (1989)].

Example 148 infra describes the ability of a subset of the compounds of the invention to block L-type voltage-activated Ca channels. L-type Ca channels regulate release of certain peptide neurotransmitters from mammalian brain nerve terminals [Rane et al., *Pflugers Arch.*, 409:361–366], and the secretion of a variety of substances such as peptide hormones of the pituitary [DeRiemer, S. A. et al., *Exp. Brain Res. Suppl.* 14:139–154 (1986)]. Said L-type Ca channels are structurally and functionally related, and in some instances are identical, to L-type Ca channels found in the cell bodies of neurons in the brain; elsewhere in the central nervous system; the peripheral nervous system; the cardiac conduction system comprising the Purkinje cell network and the atrial bundle branches; and cardiac, skeletal, and smooth muscle cells [Bean, B. P., *Ann. Rev. Physiol.*, 51:367–384 (1989); Snutch, T. P. et al., *Curr. Opin. Neurobiol.* 2:247–253 (1992)]. Therefore, the results disclosed in Example 148 indicate the ability of compounds of the invention to block said channels in the aforementioned tissues.

Compounds of the invention may be considered effective blockers of said voltage-activated Na and Ca channels if the compound causes at least a 50% reduction of the flow of cations through said channels at concentrations of about 100 $\mu$M according to the protocols disclosed in Examples 146–148, infra. More preferably the compound will cause at least a 50% inhibition of cation flow through said channels at a concentration of about 10 $\mu$M according to the protocols of said Examples 146–148, infra.

Compounds of the invention have also demonstrated anticonvulsant activity in an in vivo as disclosed in Example 150, infra.

Suitable halogen groups of compounds of the invention (including compounds of Formulas I, IA, IB, II, III, IIIA, IIIB, IIIBB, IV, IV(A), IV(B), IV(BB) or V as specified above) are F, Cl, Br and I. Preferred alkyl groups include those having 1 to about 12 carbon atoms, more preferably 1 to about 10 carbon atoms such as methyl, ethyl, n-propyl, iso-propyl, n-butyl, t-butyl, iso-butyl, sec-butyl, pentyl, hexyl, heptyl, etc. Preferred alkenyl and alkynyl groups include those groups having one or more unsaturated linkages, preferably one or two unsaturated linkages and from 2 to about 12 carbon atoms, more preferably 2 to about 8 carbon atoms. Each of the terms alkyl, alkenyl and alkynyl as used herein refer to both cyclic and noncyclic groups, although typically straight or branched chain noncyclic groups are generally more preferred. Preferred alkoxy groups of compounds of the invention include groups having one or more oxygen linkages and from 1 to about 12 carbon atoms, more preferably 1 to about 8 carbon atoms, still more preferably 1 to about 6 carbons. Straight and branched chain butocy, pentoxy, and hexoxy are particularly preferred. Preferred aryloxy groups have 6 to about 20 carbon atoms or from 6 to about 12 carbon atoms and include an oxygen atom. Substituted or unsubstituted phenoxy and naphthoxy are preferred aryloxy groups. Preferred aralkoxy groups have from 6 to about 20 carbon atoms and include an alkoxy group as specified above that contains one or more aryl substituents, particularly one or more carbocyclic aryl substituents. Typically an oxygen will be the terminal group of the substituent. Substituted or unsubstituted benzyloxy (i.e., $C_6H_5CH_2O$—) are preferred aralkoxy groups. Preferred thioalkyl groups include groups having one or more thioether linkages and from 1 to about 12 carbon atoms, more preferably 1 to about 8 carbon atoms, still more preferably 1 to about 6 carbons. Preferred aminoalkyl groups include those groups having one or more primary, secondary and/or tertiary amine groups, and from 1 to about 12 carbon atoms, more preferably 1 to about 8 carbon atoms, still more preferably 1 to about 6 carbons. Secondary and tertiary amine groups are generally more preferred than primary amine moieties. Preferred alkylsulfinyl groups have one or more sulfinyl (SO) groups, more typically one sulfinyl group, and from 1 to about 12 carbon atoms, more preferably 1 to about 6 carbons, and even more preferably 1–3 carbon atoms. Preferred alkylsulfonyl groups have one or more sulfono ($SO_2$) groups, more typically one sulfono group, and from 1 to about 12 carbon atoms, more preferably 1 to about 6 carbons, and even more preferably 1–3 carbon atoms. Preferred alkenylene and alkynylene X and X' groups of compounds of Formulas III and IIIA have one or two carbon-carbon multiple bonds. Preferred heteroalkylene, heteralkenylene and heteroalkynylene X and X' groups of compounds of Formulas III and IIIA contain 1 to about 3 hetero atoms consisting of N, O and/or S atoms, where one or more of said hetero atoms is a chain member of the X or X' group, and more preferably contain about 1–3 carbon atoms in addition to said hetero atoms. Suitable heteroaromatic and heteroalicyclic groups of compounds of the invention contain one or more N, O or S atoms and include, e.g., quinolinyl including 8-quinolinyl, indolinyl including 5-indolinyl, furyl, thienyl, pyrrolyl, thiazolyl, pyridyl, pyrimidinyl, pyridazinyl, oxazolyl and phthalimido groups all of which may be optionally independently substituted at one or more available positions and/or fused to a benzene ring; and substituted or unsubstituted tetrahydrofuranyl, tetrahydropyranyl, piperidinyl, piperazinyl, morpholino, pyrrolidinyl groups, pyrazinyl, coumarinyl, tetrahydroquinolinyl, tetrahydroisoquinolinyl, benzothiazolyl, benzotriazolyl, and bezimidazolyl. Preferred carbocyclic aryl groups include those having about 6 to about 20 carbons, more preferably about 1 to 3 separate or fused rings and from 6 to about 18 carbon atoms such as phenyl, naphthyl, acenaphthyl, phenanthryl, anthracyl and fluorene groups.

Said substituted moieties of compounds of the invention may be substituted at one or more available positions by one or more suitable groups such as, e.g., halogen such as F, Cl, Br, or I; cyano; hydroxyl; nitro; azido; carboxy; carbocyclic aryl; alkyl groups including alkyl groups having from 1 to about 12 carbon atoms or from 1 to about 6 carbon atoms; alkenyl and alkynyl groups including groups having one or more unsaturated linkages and from 2 to about 12 carbon atoms or from 2 to about 6 carbon atoms; alkoxy groups such as those groups having one or more oxygen linkages and from 1 to about 12 carbon atoms or from 1 to about 6 carbon atoms; thioalkyl groups such as those groups having one or more thioether linkages and from 1 to about 12 carbon atoms or from 1 to about 6 carbon atoms; aminoalkyl groups such as groups having one or more N atoms and from 1 to about 12 or 1 to about 6 carbon atoms; alkylsulfinyl such as those groups having one or more sulfinyl groups and from 1 to about 12 carbon atoms or from 1 to about 6 carbon atoms; alkylsulfonyl such as those groups having one or more sulfono groups and from 1 to about 1 2 carbon atoms or from 1 to about 6 carbon atoms.

Specifically preferred substituted groups include carboxylic acyl groups, preferably having from 1 to about 12 or 1 to about 6 carbon atoms such as acetyl, propanoyl, isopropanoyl, butanoyl, sec-butanoyl, pentanoyl and hexanoyl groups. Also preferred substituted moieties are alkaryl groups which include single and multiple ring compounds, including multiple ring compounds that contain separate and/or fused aryl groups, e.g., above-mentioned aryl groups substituted by one or more $C_3-C_{10}$ alkyl groups such as phenylpropyl, phenylbutyl, phenylpentyl and phenylhexyl groups as well as the branched chain isomers thereof such as tert-butylphenyl, sec-butylphenyl, etc. Haloalkyl and haloalkoxy are also preferred, particularly fluoroalkyl and fluoroalkoxy such as trifluoromethyl and trifluoroalkoxy. Aroyl groups are also preferred substituted groups such as carbonyl substituted by phenyl, naphthyl, acenaphthyl, phenanthryl, and anthracyl groups and carboxylic acyl groups substituted by one or more aryl groups, e.g., diphenylacetoxy and fluorenecarboxy groups. Aralkanoyl groups are also preferred and include carbonyl substituted by the aralkyl groups described above. Aralkoxy groups are also preferred substituted groups and include alkoxy groups substituted by phenyl, naphthyl, acenaphthyl, phenanthyl, and anthracyl groups. Preferred substituted aryl groups include the above described aryl groups substituted by halo, hydroxy, alkyl, alkenyl, alkynyl, alkoxy, amino, aminoalkyl, thioalkyl and the like.

Particularly preferred R and $R^1$ substituent groups of compounds of Formula I, as defined above, include substituted and unsubstituted carbocyclic aryl such as phenyl, butylphenyl including tert-butylphenyl, cyclohexylphenyl, butoxyphenyl, trifluoromethoxyphenyl, halophenyl, methylthiophenyl, acenaphthyl, naphthyl including substituted naphthyl such as methoxy-1-naphthyl, and the like; and aralkyl groups including substituted and unsubstituted benzyl groups such as tert-butylbenzyl, isopropylbenzyl, halobenzyl, trifluoromethoxybenzyl, cinnamylmethylene, naphthylmethylene, benzyloxy and the like.

Specifically preferred compounds of Formula I include:
N-(4-sec-butylphenyl)-N-benzylguanidine;
N-(5-acenaphthyl)-N-benzylguanidine;
N-(3-acenaphthyl)-N-benzylguanidine;
N-(5-acenaphthyl)-N-(4-isopropylbenzyl)guanidine;
N-(3-acenaphthyl)-N-(4-isopropylbenzyl)guanidine;
N-(4-cyclohexylphenyl)-N-(4-isopropylbenzyl)guanidine;
N-(4-cyclohexylphenyl)-N-(4-tert-butylbenzyl)guanidine;
N-(2-fluorenyl)-N-(4-tert-butylbenzyl)guanidine;
N-(4-sec-butylphenyl)-N-(cinnamylmethylene)guanidine;
N-(4-n-butoxyphenyl)-N-(4-tert-butylbenzyl)guanidine;
N-(3-biphenyl)-N-(4-tert-butylbenzyl)guanidine;
N-(5-indanyl)-N-(4-tert-butylbenzyl)guanidine;
N-(3-trifluoromethoxyphenyl)-N-(4-tert-butylbenzyl) guanidine;
N-(4-sec-butylphenyl)-N-(4-tert-butylbenzyl)guanidine;
N-(5-acenaphthyl)-N-(4-tert-butylbenzyl)guanidine;
N-(3-acenaphthyl)-N-(4-tert-butylbenzyl)guanidine;
N-(methoxy-1-naphthyl)-N-(4-tert-butylbenzyl)guanidine;
N-(1-naphthyl)-N-(4-tert-butylbenzyl)guanidine;
N-(3-iodophenyl)-N-(4-tert-butylbenzyl)guanidine;
N-(4-chloro-1-naphthyl)-N-(4-tert-benzyl)guanidine;
N-(4-tert-butylphenyl)-N-(4-tert-butylbenzyl)guanidine;
N-(4-iodophenyl)-N-(4-tert-butylbenzyl)guanidine;
N-(1-naphthylmethyl)-N-(4-tert-butylbenzyl)guanidine;
N-(5-acenaphthyl)-N-(3-phenoxybenzyl)guanidine;
N-(3-trifluoromethylphenyl)-N-(4-tert-butylbenzyl) guanidine;
N-(3-methylthiophenyl)-N-(4-tert-butylbenzyl)guanidine;
N-(5-acenaphthyl)-N-(3-iodobenzyl)guanidine;
N-(5-acenaphthyl)-N-(cinnamyl)guanidine;
N-(5-acenaphthyl)-N-(4-iodobenzyl)guanidine;
N-(5-acenaphthyl)-N-(4-trifluoromethoxybenzyl)guanidine;
and pharmaceutically acceptable salts thereof.

Specifically preferred compounds of Formula II include:
N,N'-bis(2-fluorenyl)guanidine;
N,N'-bis(2-fluorenyl)-N-methylguanidine;
N,N'-bis(2-fluorenyl)-N,N'-dimethylguanidine;
N,N'-bis(anthracenyl)guanidine;
N,N'-bis(anthracenyl)-N-methylguanidine;
N,N'-bis(anthracenyl)-N,N'-dimethylguanidine;
N,N'-bis(phenanthracenyl)guanidine;
N,N'-bis (phenanthracenyl)-N-methylguanidine;
N,N'-bis(phenanthracenyl)-N,N'-dimethylguanidine;
N,N'-bis(fluoranthenyl)guanidine;
N,N'-bis(fluoroanthenyl)-N-methylguanidine;
N,N'-bis(fluoroanthenyl)-N,N'-dimethylguanidine;
N-(anthracenyl)-N'-(1-adamantyl)guanidine;
N-(anthracenyl)-N'-(1-adamantyl)-N-methylguanidine;
N-(anthracenyl)-N'-(1-adamantyl)-N'-methylguanidine;
N-(anthracenyl)-N'-(1-adamantyl)-N,N'-dimethylguanidine;
N-(anthracenyl)-N'-(2-adamantyl)guanidine;
N-(anthracenyl)-N'-(2-adamantyl)-N-methylguanidine;
N-(anthracenyl)-N'-(2-adamantyl)-N'-methylguanidine;
N-(anthracenyl)-N'-(2-adamantyl)-N,N'-dimethylguanidine;
N-(phenanthracenyl)-N'-(1-adamantyl)guanidine;
N-(phenanthracenyl)-N'-(1-adamantyl)-N-methylguanidine;
N-(phenanthracenyl)-N'-(1-adamantyl)-N'-methylguanidine;
N-(phenanthracenyl)-N'-(1-adamantyl)-N,N'-dimethylguanidine;
N-(phenanthracenyl)-N'-(2-adamantyl)guanidine;
N-(phenanthracenyl)-N'-(2-adamantyl)-N-methylguanidine;
N-(phenanthracenyl)-N'-(2-adamantyl)-N'-methylguanidine;
N-(phenanthracenyl)-N'-(2-adamantyl)-N,N'-dimethylguanidine;
N-(fluorenyl)-N'-(1-adamantyl)guanidine;
N-(fluorenyl)-N'-(1-adamantyl)-N-methylguanidine;
N-(fluorenyl)-N'-(1-adamantyl)-N'-methylguanidine;
N-(fluorenyl)-N'-(1-adamantyl)-N,N'-dimethylguanidine;
N-(fluorenyl)-N'-(2-adamantyl)guanidine;
N-(fluorenyl)-N'-(2-adamantyl)-N-methylguanidine;
N-(fluorenyl)-N'-(2-adamantyl)-N'-methylguanidine;
N-(fluorenyl)-N'-(2-adamantyl)-N,N'-dimethylguanidine;
N-(fluorenyl)-N'-(methoxynaphthyl)guanidine;
N-(fluorenyl)-N'-(methoxynaphthyl)-N-methylguanidine;
N-(fluorenyl)-N'-(methoxynaphthyl)-N'-methylguanidine;

N-(fluorenyl)-N'-(methoxynaphthyl)-N,N'-dimethylguanidine;

and pharmaceutically acceptable salts of said compounds.

Particularly preferred R substituent groups of compounds of Formulas III and IIIA, as those formulas are defined above, include phenyl and naphthyl. Preferred values of n, n' and m of compounds of Formulas III and IIIA are 1 and 2. The R groups are suitably the same where n is greater than one. Carbocyclic aryl groups of compounds of Formulas III and IIIA are preferred $R^1$ groups, particularly substituted and unsubstituted phenyl, naphthyl and acenaphthyl. Preferred X groups of compounds of Formulas III and IIIA include alkenylene groups substituted by halogen of F, Cl, Br and I; aryloxy such as substituted and unsubstituted phenoxy; aryl such as substituted and unsubstituted phenyl including phenyl substituted by $C_1$–$C_6$ alkyl, $C_1$–$C_8$ alkoxy, halogen such as F, Cl, Br or I.

Specifically preferred compounds of Formulas III and IIIA include:
N-5-acenaphthyl-N'-benzhydrylguanidine;
N-5-acenaphthyl-N'-benzhydryl-N-methylguanidine;
N-5-acenaphthyl-N'-benzhydryl-N'-methylguanidine;
N-5-acenaphthyl-N'-benzhydryl-N,N'-dimethylguanidine;
N-3-acenaphthyl-N'-benzhydrylguanidine;
N-3-acenaphthyl-N'-benzhydryl-N-methylguanidine;
N-3-acenaphthyl-N'-benzhydryl-N'-methylguanidine;
N-3-acenaphthyl-N'-benzhydryl-N,N'-dimethylguanidine;
N-(5-acenaphthyl)-N'-[(1-naphthyl)-methyl]guanidine;
N-(5-acenaphthyl)-N'-[(1-naphthyl)-methyl]-N-methylguanidine;
N-(5-acenaphthyl)-N'-[(1-naphthyl)-methyl]-N'-methylguanidine;
N-(5-acenaphthyl)-N'-[(1-naphthyl)-methyl]-N,N'-dimethylguanidine;
N-(5-acenaphthyl)-N'-(1-methyl-2-phenoxyethyl)guanidine;
N-(5-acenaphthyl)-N'-(1-methyl-2-phenoxyethyl)-N-methylguanidine;
N-(5-acenaphthyl)-N'-(1-methyl-2-phenoxyethyl)-N'-methylguanidine;
N-(5-acenaphthyl)-N'-(1-methyl-2-phenoxyethyl)-N,N'-dimethylguanidine;
N-(5-acenaphthyl)-N'-(1-methyl-2-(4-chlorophenyl)ethyl)guanidine;
N-(5-acenaphthyl)-N'-(1-methyl-2-(4-chlorophenyl)ethyl)-N-methylguanidine;
N-(5-acenaphthyl)-N'-(1-methyl-2-(4-chlorophenyl)ethyl)-N'-methylguanidine;
N-(5-acenaphthyl)-N'-(1-methyl-2-(4-chlorophenyl)ethyl)-N,N'-dimethylguanidine;
N-(5-acenaphthyl)-N'-(1,2-diphenylethyl)guanidine;
N-(5-acenaphthyl)-N'-(1,2-diphenylethyl)-N-methylguanidine;
N-(5-acenaphthyl)-N'-(1,2-diphenylethyl)-N'-methylguanidine;
N-(5-acenaphthyl)-N'-(1,2-diphenylethyl)-N,N'-dimethylguanidine;
N-(5-acenaphthyl)-N'-(3-phenylpropyl)guanidine;
N-(5-acenaphthyl)-N'-(3-phenylpropyl)-N-methylguanidine;
N-(5-acenaphthyl)-N'-(2-methyl-2-phenylethyl)-N'-methylguanidine;
N,N'-(sec-butylphenyl)-N'-(2-phenoxyethyl)guanidine;
N,N'-(sec-butylphenyl)-N'-(2-phenoxyethyl)-N-methylguanidine;
N,N'-(sec-butylphenyl)-N'-(2-phenoxyethyl)-N'-methylguanidine;
N,N'-(sec-butylphenyl)-N'-(2-phenoxyethyl)-N,N'-dimethylguanidine;
N-(5-acenaphthyl)-N'-((4-tert-butylphenyl)-(4-sec-butylphenyl)-methyl)guanidine;
N-(5-acenaphthyl)-N'-((4-tert-butylphenyl)-(4-sec-butylphenyl)-methyl)-N-methylguanidine;
N-(5-acenaphthyl)-N'-((4-tert-butylphenyl)-(4-sec-butylphenyl)-methyl)-N'-methylguanidine;
N-(5-acenaphthyl)-N'-((4-tert-butylphenyl)-(4-sec-butylphenyl)-methyl)-N,N'-dimethylguanidine;
N-(4-butoxyphenyl)-N,N'-bis(4-tert-butylbenzyl)guanidine;
N-(4-butoxyphenyl)-N,N'-bis(4-tert-butylbenzyl)-N-methylguanidine;
N-(4-butoxyphenyl)-N,N'-bis(4-tert-butylbenzyl)-N'-methylguanidine;
N-(4-butoxyphenyl)-N,N'-bis(4-tert-butylbenzyl)-N,N'-dimethylguanidine;

and pharmaceutically acceptable salts of said compounds.

Particularly preferred R substituent groups of compounds of Formula IV, as that formula is defined above, include halo, alkyl, alkoxy, benzyloxy, aminoalkyl, alkylthio, alkylsulfinyl, alkylsulfono, alkenyl and alkynyl. Further preferred is where $R^1$ is carbocyclic aryl, particularly substituted or unsubstituted phenyl, naphthyl or acenaphthyl. Alkyl including methyl, ethyl and propyl are preferred $R^2$ or $R^3$ groups.

Specifically preferred compounds of Formula IV include:
N,N'-di-(4-sec-butylphenyl)guanidine;
N,N'-di-(4-sec-butylphenyl)-N-methylguanidine;
N,N'-di-(4-sec-butylphenyl)-N,N'-dimethylguanidine;
N-(2-naphthyl)-N'-(4-isopropylphenyl)guanidine;
N-(2-naphthyl)-N'-(4-isopropylphenyl)-N-methylguanidine;
N-(2-naphthyl)-N'-(4-isopropylphenyl)-N'-methylguanidine;
N-(2-naphthyl)-N'-(4-isopropylphenyl)-N,N'-dimethylguanidine;
N,N'-bis(4-tert-butylphenyl)guanidine;
N,N'-bis(4-tert-butylphenyl)-N-methylguanidine;
N,N'-bis(4-tert-butylphenyl)-N'-methylguanidine;
N,N'-bis(4-tert-butylphenyl)-N,N'-dimethylguanidine;
N-(4-sec-butylphenyl)-N'-(2,3,4-trichlorophenyl)guanidine;
N-(4-sec-butylphenyl)-N'-(2,3,4-trichlorophenyl)-N-methylguanidine;
N-(4-sec-butylphenyl)-N'-(2,3,4-trichlorophenyl)-N'-methylguanidine;
N-(4-sec-butylphenyl)-N'-(2,3,4-trichlorophenyl)-N,N'-dimethylguanidine;
N-(4-methoxy-1-naphthyl)-N'-(2,3,4-trichlorophenyl)guanidine;
N-(4-methoxy-1naphthyl)-N'-(2,3,4-trichlorophenyl)-N-methylguanidine;
N-(4-methoxy-1-naphthyl)-N'-(2,3,4-trichlorophenyl)-N'-methylguanidine;
N-(4-methoxy-1-naphthyl)-N'-(2,3,4-trichlorophenyl)-N,N'-dimethylguanidine;
N,N'-bis-(4-sec-butyl phenyl)-2-iminopyrimidazolidine;
N,N'-bis(3-biphenyl)guanidine;
N,N'-bis(3-biphenyl)-N-methylguanidine;
N,N'-bis(3-biphenyl)-N'-methylguanidine;
N,N'-bis(3-biphenyl)-N,N'-dimethylguanidine;
N,N'-di-(3-tert-butyl phenyl)guanidine;
N,N'-di-(3-tert-butylphenyl)-N-methylguanidine;
N,N'-di-(3-tert-butylphenyl)-N'-methylguanidine;
N,N'-di-(3-tert-butylphenyl)-N,N'-dimethylguanidine;
N,N'-bis(4-methoxy-1-naphthyl)guanidine;
N,N'-bis-(4-methoxy-1-naphthyl)-N-methylguanidine;

N,N'-bis-(4-methoxy-1-naphthyl)-N'-methylguanidine;
N,N'-bis-(4-methoxy-1-naphthyl)-N,N'-dimethylguanidine;
N,N'-bis-(3-sec-butylphenyl)guanidine;
N,N'-bis-(3-sec-butylphenyl)-N-methylguanidine;
N,N'-bis-(3-sec-butylphenyl)-N'-methylguanidine;
N,N'-bis-(3-sec-butylphenyl)-N,N'-methylguanidine;
N,N'-bis(4-n-butylphenyl)guanidine;
N,N'-bis(4-n-butylphenyl)-N-methylguanidine;
N,N'-bis(4-n-butylphenyl)-N'-methylguanidine;
N,N'-bis(4-n-butylphenyl)-N,N'-dimethylguanidine;
N,N'-(sec-butylphenyl)-N'-(n-pentyl)guanidine;
N,N'-bis(3-benzyloxyphenyl)guanidine;
N,N'-bis(3-benzyloxyphenyl)-N-methylguanidine;
N,N'-bis(3-benzyloxyphenyl)-N,N'-dimethylguanidine;
N,N'-bis(4-benzyloxyphenyl)guanidine;
N,N'-bis(4-benzyloxyphenyl)-N-methylguanidine;
N,N'-bis (4-benzyloxyphenyl)-N,N'-dimethylguanidine;
N-(3-benzyloxyphenyl)-N'-(4-benzyloxyphenyl)guanidine;
N-(3-benzyloxyphenyl)-N'-(4-benzyloxyphenyl)-N-methylguanidine;
N-(3-benzyloxyphenyl)-N'-(4-benzyloxyphenyl)-N'-methylguanidine;
N-(3-benzyloxyphenyl)-N'-(4-benzyloxyphenyl)-N,N'-dimethylguanidine;
N,N'-bis-(4-tert-butylphenyl)-2-iminopyrimidazolidine;
N,N'-bis-(4-pentylphenyl)-2-iminopyrimidazolidine;
N,N'-bis-(4-hexylphenyl)-2-iminopyrimidazolidine;
N,N'-bis-(naphthyl)-2-iminopyrimidazolidine;
N,N'-bis-(5-acenaphthyl)-2-iminopyrimidazolidine;
N,N'-bis-(tetralinyl)-2-iminopyrimidazolidine;
and pharmaceutically acceptable salts of said compounds.

Specifically preferred compounds of Formula V, as defined above, include:
N-(5-acenaphthyl)-N'-(1,2,3,4tetrahydroquinolinyl)guanidine;
N-(5-acenaphthyl)-N'-(1,2,3,4tetrahydroquinolinyl)-N-methylguanidine;
N-(5-acenaphthyl)-N'-(1,2,3,4tetrahydroquinolinyl)-N'-methylguanidine;
N-(5-acenaphthyl)-N'-(1,2,3,4tetrahydroquinolinyl)-N,N'-dimethylguanidine;
N-(3-acenaphthyl)-N'-(indolinyl)guanidine;
N-(3-acenaphthyl)-N'-(indolinyl)-N-methylguanidine;
N-(3-acenaphthyl)-N'-(indolinyl)-N'-methylguanidine;
N-(3-acenaphthyl)-N'-(indolinyl)-N,N'-methylguanidine;
N-(5-acenaphthyl)-N'-(piperonyl)guanidine;
N-(5-acenaphthyl)-N'-(piperonyl)-N-methylguanidine;
N-(5-acenaphthyl)-N'-(piperonyl)-N'-methylguanidine;
N-(5-acenaphthyl)-N'-(piperonyl)-N,N'-dimethylguanidine;
and pharmaceutically acceptable salts of such compounds.

The invention also includes the following compounds, particularly for use in the methods of treatment disclosed herein:
N-(2-naphthyl)-N'-(2-adamantyl)guanidine;
N-(2-naphthyl)-N'-(2-adamantyl)-N-methylguanidine;
N-(2-naphthyl)-N'-(2-adamantyl)-N'-methylguanidine;
N-(2-naphthyl)-N'-(2-adamantyl)-N,N'-dimethylguanidine;
N,N'-bis-(5-indanyl)-guanidine;
N,N'-bis(6-benz[cd]indolinyl-2[1H]-one)guanidine;
and pharmaceutically acceptable salts thereof.

Other specifically preferred compounds of the invention, including of the Formulas I–V above, include the following and are particularly preferred for use in the methods of treatment disclosed herein:
N-(3-sec-butylphenyl)-N-(4-tert-butylbenzyl)guanidine;
N-(3-tert-butylphenyl)-N-(4-tert-butylbenzyl)guanidine;
N-(3-pentoxyphenyl)-N-(4-tert-butylbenzyl)guanidine;
N-(5-acenaphthyl)-N-(4-benzyloxybenzyl)guanidine;
N-(4-sec-butylphenyl)-N-(4-benzyloxybenzyl)guanidine;
N-(4-benzyloxyphenyl)-N-(4-benzyloxybenzyl)guanidine;
N-(5-acenaphthyl)-N-(3-benzyloxybenzyl)guanidine;
N-(4-isopropylphenyl)-N-(4-tert-butylbenzyl)guanidine;
N-(4-benzyloxyphenyl)-N-(4-tert-butylbenzyl)guanidine;
N-(4-hexylphenyl)-N-(4-tert-hexylbenzyl)guanidine;
N-(4-sec-butylphenyl)-N-(4-t-butylbenzyl)-N'-pyrrolidinylguanidine;
N-(4-sec-butylphenyl)-N-(4-t-butylbenzyl)-N'-(4-thiomorpholinyl)guanidine;
N-(4-sec-butylphenyl)-N-(4-tert-butylbenzyl)-N'-piperidinylguanidine;
N-(4-sec-butylphenyl)-N-(4-tert-butylbenzyl)-N'-(4-morpholinyl)guanidine;
N-(4-sec-butylphenyl)-N-(4-tert-butylbenzyl)-N'-(4-propylpiperidinyl)guanidine;
N-(4-butoxyphenyl)-N-(4-tert-butylbenzyl)-N'-(4-piperidinyl)guanidine;
N-(4-sec-butylphenyl)-N-(4-tert-butylbenzyl)-N'-(4-benzylpiperidinyl)guanidine;
N-(4-benzyloxyphenyl)-N-(4-tert-butylbenzyl)-N'-(4-morpholinyl)guanidine;
N-(4-sec-butylphenyl)-N-(4-tert-butylbenzyl)-N'-(1,2,3,4-tetrahydroisoquinolinyl)guanidine;
N-(3-butoxy-4-methoxyphenyl)-N-(4-tert-butylbenzyl)-N'-(4-morpholinyl)guanidine;
N-(4-sec-butylphenyl)-N-(4-tert-butylbenzyl)-N'-(3,5-dimethyl-4-morpholinyl)guanidine;
N-(4-tert-butylphenyl)-N-(4-tert-butylbenzyl)-N'-(4-sec-butylphenyl)-N'-(methyl)guanidine;
N-(4-sec-butylphenyl)-N-(4-tert-butylbenzyl)-N'-(4-sec-butylphenyl)-N'-(methyl)guanidine;
N-(4-sec-butylphenyl)-N-(4-tert-butylbenzyl)-N'-(phenyl)guanidine;
N-(4-sec-butylphenyl)-N-(4-tert-butylbenzyl)-N'-(4-chlorophenyl)guanidine;
N-(4-butoxyphenyl)-N-(4-tert-butylbenzyl)-N'-(phenyl)guanidine;
N-(4-sec-butylphenyl)-N-(4-tert-butylbenzyl)-N'-(phenyl)-N'-methylguanidine;
N-(4-sec-butylphenyl)-N-(4-tert-butylbenzyl)-N'-(3,4-dichlorophenyl)guanidine;
N-(4-hexylphenyl)-N-(4-tert-hexylbenzyl)-N'-phenylguanidine;
N-(4-sec-butylphenyl)-N-(4-tert-butylbenzyl)-N'-(4 benzyloxyphenyl)guanidine;
N,N'-bis-(4-tert-butylphenyl)-N,N'-dimethylguanidine
N-(4-benzyloxyphenyl)-N'-(4-tert-butylphenyl)guanidine;
N,N'-bis-(3-(1'-methyl-2'-phenyl)ethyl)guanidine;
N-methyl-N-4-benzyloxyphenyl-N'-(4-tert-butylphenyl)guanidine;
N,N'-bis-(4-hexylphenyl)guanidine;
N-(3-(1-(4'-ethoxy)benzyl)phenethyl)-N'-(4-tert-butylphenyl)guanidine;
N-(4-benzyloxyphenyl)-N'-methyl-N-(4-tert-butylphenyl)guanidine;
N-(3-(4-tert-butylbenzyloxy) phenyl)-N'-(4-tert-butylphenyl)guanidine;
N-(3-(1'-benzylbutyl)phenyl)-N'-(4-tert-butylphenyl)guanidine;
N,N'-bis-(4-butylphenyl)-N-methylguanidine;
N,N'-bis-(4-tert-butylphenyl)-N,N'-dimethylguanidine;
N-(3-naphthaloxyphenyl)-N'-(4-tertbutylphenyl)guanidine;
N-(4-benzyloxyphenyl)-N'-(4-butylphenyl)guanidine;
N,N'-bis-(4-butylphenyl)-N-butylguanidine;
N-3-(benzyloxymethyl)phenyl-N'-(4-tert-butylphenyl)guanidine;

N-(3,4-bis-butyloxyphenyl)-N'-(4-tert-butylphenyl) guanidine;
N-(3-benzyloxy) phenyl-N'-(4-tert-butylphenyl)guanidine;
N,N'-bis-(3-butoxy-4-methoxy)phenylguanidine;
N-(4-benzyloxyphenyl)-N-methyl-N'-(4-butylphenyl) guanidine;
N-(4-benzyloxyphenyl)-N'-methyi-N'-(4-butylphenyl) guanidine;
N,N'-bis-(6-tetralinyl)guanidine;
N-(6-tetralinyl)-N'-(4-tert-butylphenyl)guanidine;
N-(5-acenaphthyl)-N'-(6-benzothiozolyl)guanidine;
N-(5-acenaphthyl)-N'-(6-N-benzylindolinyl)guanidine;
N-(5-acenaphthyl)-N'-(4-benzo-2,1,3-thiadizaole) guanidine;
N-(5-acenaphthyl)-N'-[4-(6-methyl-benzothiazole) phenylguanidine;
N-(5-acenaphthyl)-N'-(1-benz[cd]indolinyl)guanidine;
N-(5-acenaphthyl)-N'-(6-benz[cd]indo-2[1H]-one) guanidine;
N-(4-butoxyphenyl)-N'-(4-chlorophenylethyl)guanidine;
N-(4-benzyloxyphenyl)-N,N'-diphenylguanidine;
N-(4-benzyloxyphenyl)-N'-benzyl-N'-phenylguanidine;
N-(3-benzyloxyphenyl)-N'-(4-thiobenzylphenyl)guanidine;
N,N'-bis(4-(phenylthio)phenyl)guanidine;
N,N'-bis(3-(phenylthio)phenyl)guanidine;
N-(5-acenaphthyl)-N'-(2-phenylethyl)guanidine;
N-(5-acenaphthyl)-N'-(3-butoxypropyl)guanidine;
N,N'-bis(2,2-diphenylethyl)guanidine;
N-(4-butoxyphenyl)-N'-(4-chlorophenylethyl)guanidine;
N-(4-butoxyphenyl)-N-(4-chlorobenzhydryl)guanidine;
(5-acenaphthyl)-N'-(phenethyl)-N'-benzylguanidine;
N-4-benzyloxyphenyl)-N'-(3-benzyloxyphenyl)-N'-(4-chlorobenzyl)guanidine;
N,N'-bis(4-benzyloxyphenyl)-N'-methylguanidine;
N-(4-benzyloxyphenyl)-N'-(3-benzyloxyphenyl)-N'-(4-chlorobenzyl)guanidine;
N-(3-benzyloxyphenyl)-N'-(4-benzyloxyphenyl)-N'-phenylguanidine;
N-(4-sec-butylphenyl)-N'-(4-isopropoxyphenyl)-N'-phenylguanidine;
N-(4-benzyloxyphenyl)-N'-(4-benzyloxyphenyl)-N'-phenylguanidine;
N,N'-bis(3-octyloxyphenyl)guanidine;
N,N'-bis(4-butoxyphenyl)guanidine;
N,N'-bis(4-phenoxyphenyl)guanidine;
N-(3-benzyloxyphenyl)-N'-(4-phenoxyphenyl)guanidine;
N-(3-benzyloxyphenyl)-N'-(4-phenylazophenyl)guanidine;
N,N'-bis(3-benzyloxyphenyl)-N'-methylguanidine;
N-(4-benzyloxphenyl)-N'-(4-benzyloxyphenyl)-N'-methylguanidine;
N-(4-butoxyphenyl)-N'-(4-isopropoxyphenyl)guanidine;
N-N'-bis(4(1-hydroxybutyl)phenyl)guanidine;
N-(4-butoxyphenyl)-N'-(3-methoxyphenyl)-N'-phenylguanidine;
N-(4-secbutylphenyl)-N'-phenyl-N'-(4-(2-isopropoxy) phenyl)guanidine;
N-(4-n-butoxyphenyl)-N'-(2-(4-chlorophenyl)ethyl) guanidine;
and pharmaceutically acceptable salts thereof.

Compounds of the invention can be prepared by reaction of an amine, typically an amine salt such as an amine hydrochloride, with a preformed alkyl or aryl cyanamide (see S. R. Safer, et al., *J. Org. Chem.*, 13:924 (1948)) or the corresponding N-substituted alkyl or aryl cyanamide. See also G. J. Durant, et al., *J. Med. Chem.*, 28:1414 (1985); C. A. Maryanoff, et al., *J. Org. Chem.*, 51:1882 (1986); M. P. Kavanaugh, et al., Proc. Natl. Acad. Sci. USA, 85:2844–2848 (1988); E. Weber, et al., Proc. Natl. Acad. Sci. USA, 83:87848788 (1986); H. W. J. Cressman, Org. Syn. Coll., 3:608–609 (1955); International Applications WO 91/12797 and PCT/US92/01050.

More particularly, synthesis of N,N-disubstituted compounds of Formula I can be achieved by condensation of a disubstituted amine with cyanamide. For example, a disubstituted amine is prepared having the desired substituents R and $R^1$ (as those substituents are defined in Formula I above), e.g., by condensation of a primary amine of the formula $R-NH_2$ with a compound of the formula $R^1$ wherein L is a leaving group and R and $R^1$ are as defined above for Formula I. Suitable reaction conditions can be readily determined based on the constituents employed. For example, a benzylhalide is suitably added to an arylamine at reduced temperature in the presence of a tertiary amine such as triethylamine and, after addition completion, the mixture is stirred at room temperature for about 15 hours. The resulting secondary amine can be purified by conventional means such as chromatography and then reacted with a suitable acid such as methanesulfonic acid to form the amine salt. The amine salt is reacted with a large molar excess of cyanamide in a suitable solvent such as methanol for a time and temperature sufficient to form the N,N-disubstituted guanidine.

Synthesis of symmetrical N,N'-disubstituted guanidines of the invention can be typically achieved by directly reacting two equivalents of the amine with one equivalent of cyanogen bromide in suitable solvent such as ethanol as depicted in "Method A" of Scheme 1 below. Unsymmetrical N,N'-disubstituted guanidines can be prepared by reacting a substituted cyanamide such as aryl cyanamides with the appropriate amine hydrohalide salts in suitable solvent such as refluxing chlorobenzene or toluene as depicted in "Method B" of Scheme 1 below. The requisite cyanamides can be synthesized from the corresponding amines by treatment with cyanogen bromide in suitable solvent such as ether.

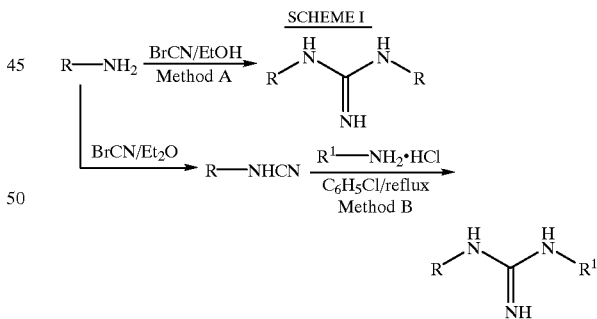

SCHEME I

N,N,N'-tri-substituted or N,N,N',N'-tetra-substituted guanidines of the invention can be synthesized (Scheme II below, Method C and D respectively) by reacting a substituted cyanamide such as a N-alkyl-N-arylcyanamide with an appropriate amine hydrohalide salt in a suitable solvent such as refluxing chlorobenzene or toluene. The starting cyanamides can be synthesized, e.g., by an alkylation of an arylcyanamide with sodium hydride/alkyl halide in suitable solvent such as tetrahydrofuran.

SCHEME II

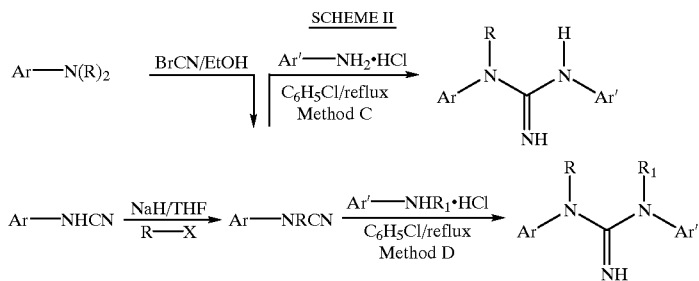

Method C

Method D

Appropriate substituted amine and cyanamide reagents are available or can be prepared by recognized procedures. A nitro acenaphthyl derivative having one or more additional ring substituents can be prepared as described by M. D. Varney, et al., *J. Med. Chem.,* 35:671 (1992). Such a substituted nitro acenaphthyl derivative can be reduced to the corresponding amine by hydrogenation, and the amine reacted with BrCN as discussed above. For preparation of other acenaphthyl derivatives having an amine or amine precursor group and one or more additional ring substituents, see V. N. Komissarov, *Zh. Org. Khim.,* 26(5): 1106–10 (1990); L. Skulski, et al., *Pol. J. Chem.,* 55(9): 1809–24 (1981); A. F. Pozharskii, *Isobret. Prom. Obraztsy, Tovarnye Znaki,* (3), 96–7 (1982); J. P. Li, et al., US 78-890736 (1978); N. S. Vorozhtsov, *Zh. Org. Khim.,* 8(2): 353–7 (1972); J. Wolinski et al., *Rocz. Chem.,* 44(9): 1721–31 (1970); A. P. Karishin, et al., *Zh. Obshch. Khim.,* 39(9): 2098–101 (1969); and V. V. Mezheritskii, et al., *Zh. Org. Khim.,* 27(10): 2198–204 (1991).

Compounds of Formula IV where $R^2$ and $R^3$ taken together form a substituted or unsubstituted alkylene linkage of from 2 to about 6 carbon atoms can be prepared as exemplified by the procedure disclosed in Example 8 which follows. Thus, as clearly understood by those skilled in the synthesis arts, an appropriate N-substituted diaminealkylene is suitably reacted with cyanogen bromide in an appropriate solvent such as an alcohol and the reaction conducted at a temperature and for a time sufficient to carry out the reaction. The cyclic reaction product can be suitably purified by conventional techniques if desired, such as by chromatography.

As discussed above, the substituted guanidines of the invention are useful for a number of therapeutic applications, including treatment of those diseases that result from modulation of a particular neurotransmitter system that can be counteracted by one or more of the substituted guanidines of the invention. As mentioned above, modulation of neurotransmitter release involves either the inhibition of neurotransmitter release, the potentiation of neurotransmitter release, or the increase or decrease of the time course of neurotransmitter release from neuronal tissue. Neurotransmitters which may be modulated by compounds of the invention include, but are not limited to those neurotransmitters identified above. One of ordinary skill in the art can select those compounds which are effective or particularly effective modulators of neurotransmitter release using the procedures disclosed herein, or in the literature such as PCT/US92/01050, with no more than routine experimentation. For example, compounds for the prevention of neuronal death in brain ischemia can be evaluated in vivo in one or more variations of the rat middle cerebral artery occlusion model. Such models are generally considered to be particularly predictive of neuroprotective efficacy in stroke [Ginsberg, et al., *Stroke,* 20:1627–1642 (1989)]. Efficacy of compounds of the invention also may be assessed in the 4vessel occlusion model of global ischemia [Pulsinelli, et al., *Stroke:*19:913–941 (1988)].

In particular, the invention provides methods for treatment and/or prophylaxis of neurological conditions such as epilepsy, neurodegenerative conditions and/or nerve cell death resulting from, e.g., hypoxia, hypoglycemia, brain or spinal chord ischemia, brain or spinal chord trauma, stroke, heart attack or drowning. Typical candidates for treatment include heart attack, stroke, brain or spinal cord injury patients, patients undergoing major surgery where brain ischemia is a potential complication and patients such as divers suffering from decompression sickness due to gas emboli in the blood stream.

The invention also provides methods to treat and/or prevent various neurodegenerative diseases of a subject such as an animal, particularly a human, by administering a therapeutically effective dose of one or more compounds of the invention. Typical neurodegenerative diseases that can be treated and/or prevented include Parkinson's disease, Huntington's disease, Amyotrophic Lateral Sclerosis, Alzheimer's disease, Down's Syndrome, Korsakoff's disease, olivopontocerebellar atrophy, HIV-induced dementia and blindness, multi-infarct dementia or diabetic neuropathy. As disclosed by Dreyer et al., *Science,* 248:364–367 (1990), gp120 neurotoxicity is associated with increased levels of $Ca^{2+}$ which are apparently mediated by Ca channels and blocked by dihydropyridine Ca channel antagonists. Though again not wishing to be bound by theory, compounds of the invention should have utility in treating HIV-induced dementia and blindness by means of preventing the release of excessive glutamate.

As noted above the invention provides methods of treating Korsakoff's disease, a chronic alcoholism-induced condition, comprising administering to a subject including a mammal, particularly a human, one or more compounds of the invention in an amount effective to treat the disease. Pretreatment of animals with the NMDA antagonist MK-801 (Merck Index, monograph 3392, 11th ed., 1989) markedly attenuates the extent of cell loss, hemorrhages and amino acid changes in a rat model of Korsakoff's disease. See P. J. Langlais, et al., *Soc. Neurosci. Abstr.,* 14:774 (1988). Therefore, compounds of the invention have utility for the attenuation of cell loss, hemorrhages and amino acid changes associated with Korsakoff's disease.

At least some compounds of the invention will have utility in treating or preventing conditions treatable by the blockage of voltage-activated sodium ion-channels. Accordingly, the invention provides methods for blockage of voltage-activated sodium channels of neuronal cells, particularly mammalian cells such as human neuronal cells, comprising the administration to the cells of an effective amount of a compound of the invention, particularly by such administration to a mammal in need of such treatment. Conditions that can be treated by blockage of sodium channels will include, e.g., epilepsy. The invention also provides methods of for blockage of sodium channels of mammalian smooth or skeletal muscle cells, comprising administering to such cells an effective amount of one or more a compounds of the invention. Such methods will also be useful, e.g., for therapy of a mammal such as a human having or susceptible to paramyotonia or hyperkalemic periodic paralysis [See Cannon, S. C. et al., *Neuron,* 10:317–326 (1993)].

Moreover, some compounds of the invention will block both sodium channels as well as presynaptic calcium channels. This dual action may be particularly desirable for neuroprotective therapies [Kucharczyk, J. et al., *Radiology,* 179:221–227 (1991)].

It has been reported that NMDA antagonists which do not cross the blood/brain barrier may be used to alleviate certain undesirable side effects of cancer chemotherapy, e.g. nausea and emesis [A. Fink-Jensen et al., *Neurosci. Lett.,* 137(2):173 (1992)]. See also Price, M. T., et al., *Soc. NeuroSci. Abstr.,* 16:377, abstr. 161.16 (1990). These actions of NMDA antagonists are presumably mediated by blockade of the postsynaptic activity of glutamate released from neurons of the peripheral nervous system. Again without wishing to be bound by theory, this indicates that compounds which block the release of glutamate will be useful for this therapeutic indication. Compounds of the invention, particularly those compounds that are charged such as in the form of a pharmaceutically acceptable salt, and those compounds that are otherwise hydrophilic such as compounds that comprise one or more polar functionalities e.g. carboxy, amino, hydroxy and the like, may have comparatively limited ability to cross the blood brain barrier. It is thus believed that compounds of the invention, especially charged or otherwise hydrophilic compounds of the invention with limited blood brain barrier permeability, will be clinically useful to ameliorate the side effects associated with chemotherapy, particularly cancer chemotherapy, that may be experienced by a mammal, particularly a human receiving such chemotherapy. The compound of the invention would be typically administered to the subject in coordination with the chemotherapy regime.

Compounds of the invention may be used in therapy in conjunction with other medicaments. For example, for treatment of a stroke victim, one or more compounds of the invention may be suitably administered together with a pharmaceutical targeted for interaction in the blood clotting mechanism such as streptokinase, TPA and urokinase. See VonKummer, R. et al., *Stroke,* 23:646–652 (1992); Sereghy, T. et al., *Stroke,* 24:1702–1708 (1993).

Compounds of the invention will be useful for treatment of secretory disorders, particularly in view of the demonstrated ability of the compounds to block Ca channels which are identical or closely related to those which regulate secretion. The invention thus includes methods for blocking voltage-activated calcium channels of mammalian secretory cells which comprises administering to such cells a blockage-effective amount of a compound of the invention. The invention further provides methods for treatment of a disease in which the pathophysiology of the disorder involves inappropriate or excessive cellular secretion of a catecholamine, a growth factor or precursor thereof (including those growth factors specifically discussed infra), a hormone or precursor thereof (including those hormones specifically discussed infra) or a member of the neuregulin family of proteins including glial growth factors, the heregulins and the neu differentiation factors. Such a method will be particularly useful for treating a mammal such as a human suffering from or susceptible to hypersecretory disorders discussed below.

More particularly, compounds of the invention could be used in treatment of a hypersecretory disorder such as pheochromocytoma, which is a disorder resulting from the presence of a tumor of the chromaffin cells in the adrenal medulla [Bravo, E. L. and Gifford, R. W. (1984) *New Eng. J. Med.* 311: 1298–1300]. This disorder is characterized by the hypersecretion of catecholamines, resulting in hypertension which may be paroxysmal and associated with attacks of palpitation, headache, nausea, breathing difficulty, and anxiety. Compound(s) of the invention also could be used in treatment of pancreatitis, which is an inflammation of the pancreas leading to hypersecretion of hormones and enzymes from the acinar cells of the pancreas, among them hormones such as vasoactive intestinal peptide (VIP) and insulin; digestive enzymes and their inactive precursors, among them lipases and proteases, deoxyribonucleases, ribonucleases, and amylase [Greenberger, N. J. et al. *Harrison's Principles of Internal Medicine,* 11 th Ed., New York, McGraw-Hill, pp.1372–1380 (1987)]. In severe cases of pancreatitis, autodigestion of the pancreas by the hypersecretion and subsequent activation of said digestive enzymes can be fatal [Greenberger, N. J. et al., ibid]. For these and other indications mediated by hypersecretory activity outside the central nervous system, compounds of the invention, particularly those which are charged and/or hydrophilic or otherwise have limited blood/brain barrier permeability should be clinically useful upon systemic and/or local administration.

Certain hypersecretory disorders may result from abnormal activity of cells within the central nervous system, among them cells of the pituitary gland, also termed the hypophysis, located at the base of the brain. Secretion of hormones and related substances from cells of the adenohypophysis is regulated by releasing factors, primarily those secreted by the hypothalamus [Cooper, P. E. et al., *Diseases of the Nervous System: Clinical Neurobiology,* eds, Saunders, Philadelphia, pp. 567–583 (1992)]. Substances secreted by the adenohypophysis include growth hormone, prolactin, thyroid stimulating hormone (TSH), and adrenocorticotrophic hormone (ACTH). Hypersecretion of these substances from the pituitary can lead to a variety of disorders of growth (e.g. acromegaly due to hypersecretion of growth hormone) and metabolism (e.g. secondary hyperthyroidism triggered by hypersecretion of TSH, and Cushing's disease, which results from excessive secretion by the pituitary of precursor peptides containing ACTH) [see Cooper, P. E. et al. ibid.]. These disorders are often due to benign tumors of the pituitary secretory cells. Compounds of the invention, particularly those that are relatively hydrophobic and/or by some means penetrate the blood/brain barrier, should have utility for treatment of such disorders by suitable administration to a subject, particularly a human. In some instances pharmacotherapy with compounds of the invention may obviate the necessity and attendant risk of neurosurgery performed for the purpose of removing such benign tumors. As referred to above, hydrophobic compounds of the invention would include those compounds that do not comprise highly polar moieties such as carboxy and the like.

Compounds of the invention also may be used in treatment of disorders involving hypersecretion of substances produced by the hypothalamus such as diabetes insipidus, which may be caused by hypersensitivity to, or excessive release of, AVP. AVP is a peptide synthesized in and released from neurons of the supraoptic and paraventricular nuclei of the hypothalamus [see Copper, P. E. et al., *Diseases of the Nervous System: Clinical Neurobiology,* eds, Saunders, Philadelphia, pp. 567–583 (1992)]. A current means of treatment of diabetes insipidus is surgical destruction of most of the cells in the supraoptic nucleus. Pharmacotherapy with compounds of the invention could in at least some instance obviate the need for such neurosurgery.

The pituitary has been indicated to secrete growth factors. Evidence shows a family of proteins, termed glial growth factors ("GGF"'s), to be a group of such growth factors secreted by the pituitary. GGF's are mitogenic for myelin-forming Schwann cells, and as such may play an important role in development and regeneration of the nervous system [Marchionni et al., *Nature,* 362:312–318 (1993)]. Bovine pituitary glands have been identified as an enriched source of GGF's, and a GGF of $M_r$ 31,000 has been purified from bovine pituitary [Lemke, G. E. et al., *J. Neurosci.,* 4:75–83 (1984)]. Multiple molecular forms of GGF may be secreted from the pituitary, either in active form or as precursors. GGF's from bovine pituitary extracts can be resolved into at least 3 activities with different molecular masses: GGF-I (34,000), GGFII (59,000), and GGFIII (45,000) [Goodearl et al., *J. Biol Chem.,* 268:18095–18102 (1993)]. GGF's are structurally related to members of a family of proteins which are known to activate the p185$^{erB2}$ receptor kinase, including the heregulins [Holmes, W. E. et al., *Science,* 256:1205–1210 (1992)], and neu differentiation factor [Wen, D. et al., *Cell,* 69:559–572 (1992)].

While the precise role of GGF's and the aforementioned related proteins in the development, maintenance, and/or repair of the nervous system and muscle has yet to be elucidated, and the mechanism of secretion of GGF's and related molecules has yet to be defined, existing evidence indicates that pathophysiological circumstances may arise in which it may be desirable to regulate the secretion of GGF's and related proteins from the pituitary and/or other secretory sites. One such circumstance may be diseases that involve the deterioration of nerve, for example diabetic neuropathy [Duchen, L. W. (1983) in *Autonomic Failure: A Textbook of Clinical Disorders of the Nervous System,* Bannister, R., ed., N.Y., Oxford Univ. Press; Foster, D. W. (1987) in *Harrison's Principles of Internal Medicine,* 11th Ed., New York, McGraw-Hill, pp. 1788–1795], or the deterioration of muscle, among them muscular dystrophies [Brooke, M. H. (1985) A Clinician's View of Neuromuscular Disease, 2nd ed., Baltimore, Williams and Wilkins; Huges, S. M., and Blau, H. M. (1990) Nature 345: 350–352]. Compounds of the invention should have therapeutic utility in treating such disorders involving the deterioration of nerve or muscle. Without wishing to be bound by theory, it is believed that compounds of the invention will have utility in treating such disorders by modulating the exocytosis from the cells in which they are synthesized of GGF's, other members of the neuregulin family, and other factors secreted into the blood which are involved in development, maintenance, or repair of nerve and/or muscle.

The aforementioned ability of compounds of the invention to block Ca channels which are identical or closely related to those which regulate cardiovascular function, as demonstrated in the examples which follow, indicate that compounds of the invention will find utility in therapy of cardiovascular disorders. Among the disorders currently known to be treatable by inhibitors of L-type Ca channels such as verapamil, diltiazem, and nifedipine are hypertension, angina pectoris, cardiac arrhythmias. As shown in Example 148, a subset of compounds of the invention show equal or greater potency for block of L-type Ca channels when compared with the ability of verapamil or diltiazem to block said channels using the same assay protocol.

The aforementioned ability of compounds of the invention to block Na channels which are closely related to those which regulate cardiovascular function, as shown in Example 149, infra, indicate that compounds of the invention will find utility in therapy of cardiovascular disorders treatable by blockers of Na channels. The invention thus includes methods for blocking voltage-activated sodium channels of mammalian cardiac cells comprising administration to such cells a blockage-effective amount of one or more compounds of the invention. A major indication for such Na channel blockers is cardiac arrhythmias, which are currently treated by blockers of Na channels, among them quinidine, procainamide, lidocaine, and diphenylhydantoin (phenytoin). Among the cardiac arrhythmias successfully treatable by said Na channel blockers are ventricular tachycardia; ventricular premature depolarizations; digitalis-induced atrial tachycardia and atrial and ventricular arrhythmias; paroxysmal supraventricular tachycardia; atrial fibrillation; and prophylaxysis against the development of supraventricular arrhythmias (see Bigger, J. T. et al., *The Pharmacological Basis of Therapeutics,* 7th Ed., eds., New York, MacMillan, pp. 748–783 (1985)). Accordingly, compounds of the invention should find utility in treatment of cardiac arrhythmias treatable by blockers of cardiac Na channels. Compounds of the invention should find utility in treatment of hypertension and/or angina pectoris treatable by blockers of cardiac Na channels. For these and other indications treatable by blocking cardiac Na channel activity, compounds of the invention, particularly those which are charged and/or hydrophilic and otherwise do not cross the blood/brain barrier, are believed to be clinically useful upon systemic and/or local administration.

Some cardiac arrhythmias, among them paroxysmal supraventricular tachycardia and other supraventricular arrhythmias, are treatable by both blockers of cardiovascular L-type channels and by blockers of cardiac Na channels. Compounds of the invention with dual actions against Na channels and Ca channels (such as N-(5-acenaphthyl)-N-(4-iso-propylbenzyl) guanidine and N-(4-methoxynaphthyl)-N'-(2,3,4-trichlorophenyl) guanidine), should thus have particular utility in treatment of said arrhythmias.

As discussed above, compounds of the invention also will be useful for treatment of chronic pain and as a local anesthetic.

The compounds of this invention can be administered to a subject such as a human intranasally, orally or by injection, e.g., intramuscular, intraperitoneal, subcutaneous or intravenous injection, or by transdermal, intraocular or enteral means. The optimal dose can be determined by conventional means including the assays described in the examples which follow. Guanidines of the invention are suitably administered to a subject in the protonated and water-soluble form, e.g., as a pharmaceutically acceptable salt of an organic or inorganic acid, e.g., hydrochloride, hydrobromide, sulfate, hemi-sulfate, mesylate, gluconate, phosphate, nitrate, acetate, oxalate, citrate, maleate, etc., prepared by procedures such as those disclosed in the examples which follow.

The compounds of this invention can be employed, either alone or in combination with one or more other therapeutic agents as discussed above, as a pharmaceutical composition in mixture with conventional excipient, i.e., pharmaceutically acceptable organic or inorganic carrier substances suitable for parenteral, enteral or intranasal application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

Intravenous or parenteral administration, e.g., subcutaneous, intraperitoneal or intramuscular administration are generally preferred.

Instances may arise in which site-specific drug-delivery methods would constitute a preferred method of delivering compounds of the invention to the tissue in need of therapy [see Tomlinson, E., *Advanced Drug Delivery Reviews,* 1:87–198 (1987)]. For example, in the case of disorders of muscle function originating from a pathophysiological condition of Na channels of skeletal muscle, among them hyperkalemic periodic paralysis, it may be desirable to microencapsulate compounds of the invention within delivery vehicles such as liposomes [Yagi, K., *Medical Applications of Liposomes,* Japan Soc. Press, Tokyo (1986); Gregoriadis, G., ed. Liposome Technology, Vol. I-III, CRC press, Inc., Cleveland (1984)], said liposomes containing a monoclonal antibody targeted to specific antigens on or near the surface of the diseased muscle cells. Said method of drug delivery should result in selective binding of the liposomes to the target tissue, and release of the compound of the invention near the abnormally functioning skeletal muscle Na channels, where said compound will inhibit the persistent activation of muscle Na channels which constitutes the molecular abnormality underlying the disease.

A targeted delivery method of one or more compounds of the invention also may be preferred for treatment of pheochromocytoma or another abnormality which results in hypersecretion of catecholamines into the blood. Because the Ca channels of chromaffin cells are closely related to those of nerve, cardiac cells, and muscle (Neher, E. et al., *Neuron,* 10:21–30 (1993); Bean, B. P. *Ann. Rev. Physiol.,* 51:367–384 (1989); Hess, P., *Ann. Rev. Neurosci.,* 13:337–56 (1990)), systemic administration of a compound of the invention at concentrations sufficient to block release of catecholamines from chromaffin cells may produce certain side effects resulting from block of, for example, neuronal and cardiovascular Ca channels. Accordingly, delivery of compounds of the invention to chromaffin cells may be enhanced and said side effects reduced by their incorporation into liposomes containing a monoclonal antibody targeted to specific antigens on or near the surface of the chromaffin cells of the hypersecreting adrenal medulla.

This method of liposome-mediated drug targeting has been reported for delivery of a variety of agents, to be used for indications such as cancer chemotherapy and destruction of tumors [e.g., Bassett, J. B. et al. *J. Urol.,* 135:612–615 (1986)]. Suitable refinements of that method as well as new methods for site-specific drug delivery will be useful for administration of compounds of the invention to a subject. In particular, appropriate methods for site-specific delivery of compounds of the invention may include incorporation of said compounds into polymer beads which afford slow site-specific release [Mathiowitz, E. et al., *J. Controlled Release,* 5:13–18 (1987)], and delivery to the target tissue by means of surgically implanted pumps.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. In general, a suitable effective dose of one or more compounds of the invention, particularly when using the more potent compound(s) of the invention, will be in the range of from 0.5 to 500 milligrams per kilogram bodyweight of recipient per day, preferably in the range of 1 to 100 milligrams per kilogram bodyweight of recipient per day. The desired dose is suitably administered once daily, or in several sub-doses, e.g., 2 to 4 sub-doses, are administered at appropriate intervals through the day, or other appropriate schedule. Such sub-doses may be administered as unit dosage forms, e.g., containing from 0.25 to 25 milligrams of compound(s) of the invention per unit dosage, preferably from 0.5 to 5 milligrams per unit dosage.

Alternatively, compounds of the invention may be administered continuously for a period of time, for example by an intravenous infusion or by means of a suitably placed transdermal patch incorporating and releasing compounds of the invention.

As disclosed above, suitably labeled compounds of the invention can be used to detect ion channel (e.g., Ca or Na) activity, which will serve to diagnosis certain human diseases as discussed herein. A compound of the invention may be suitably radiolabeled, e.g. with 1251 such as on an aryl ring of the compound, and the labeled compound administered to a subject and the subject then scanned for binding of the compound to ion channels using an appropriate scanning tool. For example, single photon emission computed topography ("SPECT") may be suitably employed to detected such binding. Suitable radiolabeled compounds of the invention may be prepared by known procedures. For example, a compound of the invention having an aromatic group, such as phenyl, that has a bromo or chloro ring substituent can be employed in an exchange labeling reaction to provide the corresponding compound having an $^{25}$I ring substituent.

As with prior guanidines such as those reported in U.S. Pat. No. 1,411,713, the guanidines of the present invention should have utility as rubber accelerators.

All documents mentioned herein are incorporated herein by reference in their entirety.

The present invention will be further illustrated with reference to the following examples which aid in the understanding of the present invention, but which are not to be construed as limitations thereof.

General Comments

In the following examples, all percentages reported herein, unless otherwise specified, are percent by weight. All temperatures are expressed in degrees Celsius.

Melting points were determined in open capillary tubes on a Thomas-Hoover apparatus and are uncorrected. Thin-layer chromatography was performed on Baker-flex 1B2-F silica gel plates. Guanidines were visualized on TLC with 254-nM UV light or as a blue spot with bromcresol spray reagent (Sigma Chemical Co.). Preparative TLC was performed on Analtech GF precoated silica gel (1000 µm) glass-backed plates (20×20 cm). The IR, $^1$H and $^{13}$C NMR spectra of all compounds were consistent with their assigned structures. NMR spectra were recorded on Varian Gemini 300 and the chemical shifts were reported in ppm (δ) relative to the residual signal of the deuterated solvent ($CHCl_3$, δ 7.26; $CHD_2OD$, δ 3.30). Infrared spectra were recorded in $CHCl_3$ (unless otherwise noted) on Perkin-Elmer model 1420. All new compounds were analyzed either for C, H, and N elemental analyses or for exact mass. Elemental analyses were performed by either Galbraith Laboratories (Knoxville, Tenn.) or MHW Laboratories (Tuscon, Ariz.). High Resolution Mass spectra (HRMS) were recorded on a Finnegan MAT 90. HPLC were performed on a C18 reverse phase column using 50:50 water:acetonitrile with 0.1% TFA as the mobile phase. BrCN was obtained from Aldrich Chemical Co., and was used as received. All starting amines were obtained from commercial sources and were purified by standard procedures before use, or they were prepared, where noted, by published procedures. Chlorobenzene, ether ($Et_2O$) and tetrahydrofuran (THF) were anhydrous quality solvents (Sure Seal) supplied by Aldrich. All other solvents were reagent grade. Alkyl- and arylcyanamides were prepared as described above and according to published procedures (e.g., PCT/US92/01050) by reaction of the amines with BrCN in ether.

EXAMPLE 1

Preparation of N-(4-sec-Butylphenyl)-N-(4-tert-butylbenzyl)guanidine.HCl

Part 1: Preparation of N-(4-sec-Butylphenyl)-4-tert-butylbenzylamine

A mixture of 4-sec-butylaniline (2.89 g, 20 mmol) and triethylamine (2.5 g, 25 mmol) in toluene (100 mL) was stirred at 4° C. for 15 hours and precipitates formed. The precipitates (triethylamine.HBr) were filtered out; the filtrate was concentrated to dryness. Then the crude reaction mixture was purified by column chromatography ($SiO_2$, hexane/$CH_2Cl_2$=5/1). N-(4-sec-butylphenyl)-4-tert-butylbenzylamine (4.5 g, an oil) was obtained.

Part 2: Preparation of N-(4-sec-Butylphenyl)-4-tert-butylbenzylamine.HCl

To a solution of N-(4-sec-butylphenyl)-4-tert-butylbenzylamine (4.5 g) in diethylether (10 mL) was added ether at HCl solution at 4° C., then the reaction mixture was stirred at 25° C. for 10 minutes. The resulting solution was the evaporated and dried under vacuum to afford 4.7 g of N-(4-sec-butylphenyl)-4-tert-butylbenzylamine.HCl.

Part 3: Preparation of N-(4-sec-Butylphenyl)-N-(4-tert-butylbenzyl)guanidine.HCl A mixture of N-(4-sec-butylphenyl)-4-tert-butylbenzylamine.HCl (0.8 g, 2.7 mmol) and cyanamide (2 g) in methanol was heated at 70° C. for 40 hours. During the 40 hour period, another two portions of cyanamide (0.5 g, each time) were added. The reaction did not go to completion; a small percentage of N-(4-sec-butylphenyl)-4-tert-butylbenzylamine.HCl remained in the mixture. The crude product was purified by column chromatography ($SiO_2$, $CH_2Cl_2$/MeOH=9/1). Then the purified compound (a mixture of the guanidine and some cyanamide) dissolved in water (20 mL) was basified to pH 14. The guanidine•free base was extracted with $CH_2Cl_2$ (20 mL, two times) and the combined extracts were concentrated. Finally, the pure N-(4-sec-butylphenyl)-N-(4-tert-butylbenzyl)guanidine was converted into its HCl salt by methanolic HCl treatment. After drying under vacuum for 15 hours, the pure product (0.6 g) was obtained as a white solid, mp: 177–178° C.; TLC: $R_f$=0.4 ($SiO_2$, $CH_2Cl_2$/MeOH=9/1); $^1$H NMR ($CD_3OD$): δ ppm 7.39–7.12 (m, ArH, 8H), 4.90 (s, $CH_2$, 1H), 4.88 (s, $CH_2$, 1H), 2.63 (m, CH, 1H), 1.57 (m, $CH_2$, 2H), 1.29 (s, $CH_3$, 9H), 1.21 (d, $CH_3$, 3H), 0.80 (t, $CH_3$, 3H); HRMS: 337.2524 (337.2518 Calcd. for $C_{22}H_{31}N_3$); HPLC: 99% pure.

EXAMPLE 2

Preparation of N-(5-Acenaphthyl)-N-(4-tert-butylbenzyl)guanidine

Part 1: Preparation of 5-Acenaphthylamine

A mixture of 5 and 3-nitroacenaphthene was reduced with Pd/C in ethyl acetate under hydrogen at 40 psi pressure and the resulting amines were separated by recrystallization from cyclohexane/ethyl acetate.

Part 2: Preparation of N-(5-Acenaphthyl)-4-tert-butylbenzylamine

A mixture of 5-acenaphthylamine (1.0 g, 6 mmol) and triethylamine (0.76 g, 7.5 mmol) in toluene (50 mL) was stirred at 4° C., and 4-tert-butylbenzyl-bromide (1.36 g, 6 mmol) was added in slowly. The reaction mixture was stirred at 23° C. for 15 hours and precipitates formed. The precipitates (triethylamine.HBr) were filtered out; the filtrate was concentrated to dryness. Then the crude reaction mixture was purified by column chromatography ($SiO_2$, hexane/$CH_2Cl_2$=5/1). N-(5-acenaphthyl)-4-tert-butylbenzylamine (1.67 g, an oil) was obtained.

Part 3: Preparation of N-(5-Acenaphthyl)-4-tert-butylbenzylamine.mesylate

To a solution of N-(5-acenaphthyl)-4-tert-butylbenzylamine (1.1 g) in diethylether (10 mL) was added methanesulfonic acid (0.8 g) at 4° C., then the reaction mixture was stirred at 25° C. for 10 minutes. The resulting solution was then evaporated and dried under vacuum to afford N-(5-acenaphthyl)-4-tert-butylbenzylamine.mesylate.

Part 4: Preparation of N-(5-Acenaphthyl)-N-(4-tert-butylbenzyl)guanidine

A mixture of N-(5-acenaphthyl)-4-tert-butylbenzylamine.mesylate (3.5 mmol) and cyanamide (0.4 g) in methanol was heated at 70° C. for 40 hours. During the 40 hour period, another two portions of cyanamide (0.5 g, each time) were added. The reaction did not go to completion; a small percentage of N-(5-acenaphthyl)-4-tert-butylbenzylamine.HCl remained in the mixture. The crude product was purified by column chromatography ($SiO_2$, MeOH/$CH_2Cl_2$=0 to 10%). The purified compound (a mixture of the guanidine and some cyanamide) dissolved in water (20 mL) was basified to pH 14. Then the guanidine-.free base was extracted with $CH_2Cl_2$ (20 mL, two times) and the combined extracts were concentrated. Finally, the pure N-(5-acenaphthyl)-N-(4-tert-butylbenzyl)guanidine was dried under vacuum for 15 hours to afford the pure product (0.6 g) as a white solid, mp: 85–86° C.; TLC: $R_f$=0.4 ($SiO_2$, $CH_2Cl_2$/MeOH=9/1); $^1$H NMR ($CD_3OD$): δ ppm 7.60–7.20 (m, ArH, 9H), 4.90 (s, $CH_2$, 2H), 3.41–3.31 (m, $CH_2$, 4H), 1.26 (s, $CH_3$, 9H); MS(EI): m/e 357.2 (M$^+$:

$C_{24}H_{27}N_3 \cdot 1/4H_2O$); Calcd. (%): C, 79.62, H, 7.66, N, 11.60; Found (%): C, 79.47; H, 7.48, N, 11.79.

EXAMPLE 3
Preparation of N-(5-Acenaphthyl)-N'-benzhydrylguanidine.HCl

Step 1. 5-Acenaphthyl cyanamide 5-aminoacenaphthene (7.0 g, 41.4 mmol) was dissolved in a mixture of ether (100 mL) and ethyl acetate (25 mL). To this solution was added 5.2 mL of a 5 M solution of cyanogen bromide in acetonitrile (25.6 mmol of cyanogen bromide). The solution was stirred overnight, with the gradual appearance of gray precipitate. The solid was removed by filtration (the hydrobromide of 5-aminoacenaphthene) and the resulting filtrate concentrated in vacuo to afford a semi-solid residue. Ether (60 mL) was added to the residue and the mixture was stirred overnight. The solid was removed (more hydrobromide of 5-aminoacenaphthene) and the filtrate concentrate to approximately 20 mL and then diluted with warm cyclohexane (15 mL). Upon standing at room temperature, off-white crystals were deposited. They were collected, washed with cyclohexane-ether (1:1) and dried in vacuo to give 1.5 g of pure product, mp: 163–65° C.

Step 2. Preparation of N-(5-Acenaphthyl)-N'-benzhydrylguanidine.HCl

A mixture of 5-acenaphthyl cyanamide (0.194 g, 1 mmol) and benzhydryl amine hydrochloride (0.209 g, 0.95 mmol; prepared from benzhydryl amine and 1.0 N HCl-ether) were heated at reflux in 10 mL of chlorobenzene. After 6 hours reflux, the mixture turned into a clear solution and the reflux continued another 12 hours. The mixture was cooled to 20° C. and concentrated on a rotavapor to give a brown syrup. This syrup was treated with norite-A in a boiling ethanol for 20 minutes to give a colorless glass. Upon stirring this glass in anhydrous ether for 10 hours at room temperature resulted in a bright white solid. The solid was collected by filtration and washed with excess of ether and dried in vacuo at 40° C. to give product (0.326 g, 79%) as a white solid, mp: 225–27° C.; TLC: $R_f$=0.4 ($CH_2Cl_2$:MeOH; 9:1); $^1H$ NMR ($CD_3OD$): 67.47–7.33 (m, 15H, ArH), 6.14 (s, 1H), 3.41 (bs, 4H, 2× —$CH_2$); MS(EI): m/e 378 ($M^+$1).

EXAMPLE 4
Preparation of N,N'-bis(4-sec-Butylphenyl)guanidine.HCl

Cyanogen bromide (0.390 g, 3.7 mmol) was added in portions to a stirred 4-sec-butyl aniline (0.746 g, 5 mmol) at room temperature. Ethanol (absolute) was added (4 mL) and the resultant clear reaction mixture was heated to reflux on an oil bath (bath temperature 80–85° C.) under argon for about 30 hours. The reaction mixture was allowed to cool to room temperature, diluted with ethanol (15 mL), treated with Norite-A (charcoal) and then 10% NaOH solution (4–5 mL) was added (pH>10). The resultant white solid was filtered and crystallized from ethanol-water to give the title compound (0.204 g, 13%) as a bright white solid, mp: 113–15° C.; TLC: $R_f$=0.4 ($CH_2Cl_2$:MeOH:$NH_4OH$; 9:1:2 drops); $^1H$ NMR ($CDCl_3$): δ 7.12 (d, 4H, J=8.48 Hz, ArH), 7.03 (d, 4H, J=8.45 Hz, ArH), 2.56 (m, 2H, 1× —CH—), 1.57 (m, 4H, 2× —$CH_2$—), 1.21 (d, 6H, J=6.99 Hz, 2× —$CH_3$), 0.82 (t, 6H, J=7.23 Hz, 2× —$CH_3$); MS(EI): m/e 324 ($M^+$1); Anal.: $C_{21}H_{29}N_3$ (323.46); Calcd. (%): C, 77.97, H, 9.04, N, 12.99; Found (%): C, 77.51, H, 9.08, N, 13.16.

EXAMPLE 5
Preparation of N,N'-bis(4-sec-Butylphenyl)-N-methyl guanidine.HCl

Step 1. Preparation of N-methyl-N-4-sec-butylphenyl cyanamide

A solution of 4-sec-butylphenyl cyanamide (2.3 g, 13.56 mmol) in THF (33 mL) was slowly added to a stirred suspension of sodium hydride (1.08 g, 27 mmol) in THF (12 mL) at room temperature. After 2 hours reflux, the reaction mixture was cooled to 20° C., methyl iodide (7.04 g, 49.6 mmol) was added and the mixture stirred the contents at 20° C. After 19 hours, the reaction was quenched by careful addition of methanol (45 mL) followed by water (100 mL). The aqueous mixture was extracted with methylene chloride (3×90 mL), dried over $MgSO_4$ and the residue was purified on flash chromatography to yield the product (2.0 g, 79%) as a orange syrup. TLC ($CHCl_3$:$CH_3OH$; 10:1); $R_f$=0.76.

Step 2. Preparation of N,N'-bis(4-sec-Butylphenyl)-N-methyl guanidine.HCl

Aluminum chloride (0.42 g, 3.1 mmol) was added to a stirred solution of N-4-sec-butylphenyl-N-methyl cyanamide (0.534 g, 2.84 mmol) in chlorobenzene (15 mL) at 145° C. After 10 minutes 4-sec-butylphenyl amine hydrochloride (0.474 g, 2.56 mmol, prepared from 4-sec-butyl aniline and 1.0 M HCl-ether) was added and continued reflux. After 2 hours, the reaction mixture was evaporated and the product was purified by flash chromatography to afford the title compound (0.45 g, 65%) as a syrup. TLC: $R_f$=0.22 ($CH_2Cl_2$:$CH_3OH$; 10:1); $^1H$ NMR ($CD_3OD$): δ 7.27 (d, 4H, J=8.18 Hz, ArH), 7.20 (d, 4H, J=8.36 Hz, ArH), 3.46 (s, 3H, —$NCH_3$), 2.69–2.58 (m, 2H, 2× —CH), 1.68–1.57 (m, 4H, 2× —$CH_2$), 1.25 (d, 6H, 2× —$CH_3$), 0.85 (t, 6H, 2× —$CH_3$); HRMS: 337.2484 (337.2528 Calcd. for $C_{22}H_{31}N_3$); HPLC: ($CH_3CN$:$H_2O$; 50:50 with 0.1% TFA): 98% pure.

EXAMPLE 6
Preparation of N,N'-Bis(4-sec-butylphenyl-N,N'-bis-methylguanidine.HCl Step 1. Preparation of N-Methyl-N-4-sec-butylphenyl cyanamide Prepared as per Step 1 of Example 5 above.

Step 2. Preparation of N-Methyl-N-4-sec-butyl aniline 4-sec-butyl aniline (4.28 g, 28.7 mmol) was dissolved in formic acid (97%, 1.85 g, 40.2 mmol) and magnetically stirred at 100–105° C. under argon. After 6 hours, the reaction mixture was cooled to 25° C. and diluted with dichloromethane (40 mL). The mixture was washed with saturated sodium bicarbonate (3×30 mL), brine (3×30 mL) and the organic phase dried over $MgSO_4$ and then evaporated to afford the formamide (3.85 g, 76%) as an amber syrup, which was used in the next step without further purification.

$LiAlH_4$-THF solution (1.0 M, 1.0 g, 26 mmol) in THF (23 mL) at ice-bath temperature. After stirring the contents at 25° C. for 20 hours, the reaction mixture was combined with saturated solution of sodium sulfate (150 mL) then filtered and washed with THF. The filtrate was evaporated and the residue was chromatographed on silica gel using hexane/ethyl acetate (8:2) as eluent to afford the title compound (1.76 g, 50%) as a liquid.

Step 3. Preparation of N,N'-Bis(4-sec-butylphenyl)-N,N'-bis-methyl guanidine.HCl Aluminum chloride (0.39 g, 2.93 mmol) was added to a stirred solution of 4-sec-butylphenyl-N-methyl cyanamide (0.5 g, 2.66 mmol) in chlorobenzene (14 mL) at 145° C. After 10 minutes 4-sec-butylphenyl-N-methyl amine hydrochloride (0.466 g, 2.34 mmol; prepared from 4-sec-butylphenyl-N-methyl amine and 1.0 M HCl-ether) was added and continued reflux. After 5 hours, the reaction mixture was evaporated on rotavapor and the product was purified by flash chromatography using chloroform/methanol (10:1) to afford the title compound (0.34 g, 38%) as an extremely hygroscopic solid, mp: 65–66° C.; TLC: $R_f$=0.13 ($CHCl_3$:$CH_3OH$; 10:1); $^1H$ NMR ($CD_3OD$): δ 6.99 (d, 4H, J=8.46 Hz, ArH), 6.80 (d, 4H, J=8.34 Hz, ArH), 3.36

(s, 6H, 2× —NCH$_3$), 2.50 (m, 2H, 2× —CH), 1.58–1.53 (m, 4H, 2× —CH$_2$), 1.16 (d, 6H, 2× —CH$_3$), 0.79 (t, 6H, J=7.35 Hz, 2× —CH$_3$); HRMS: 351.2660 (351.2674 Calcd. for C$_{23}$HH$_{33}$N$_3$); Anal.: C$_{23}$H$_{33}$N$_3$.HCl; 1.75 H$_2$O (418.74); Calcd. (%): C, 66.19, H, 8.64, N, 10.07; Found (%): C, 66.56, H, 8.55, N, 11.27; HPLC: (CH$_3$CN:H$_2$O 50:50 with 0.1% TFA): 99% pure.

EXAMPLE 7
Preparation of N-(5-Acenaphthyl)-N'-(1,2,3,4-tetrahydroquinolinyl)guanidine.mesylate Part 1: Preparation of 5-Acenaphthyl cyanamide A mixture of 5 and 3-nitroacenaphthene was reduced with Pd/C in ethyl acetate under hydrogen at 40 psi pressure and the resulting amines were separated by recrystallization from cyclohexane/ethyl acetate. 5-acenaphthyl amine further reacted with cyanogen bromide to yield 5-acenaphthyl cyanamide.

Part 2: Preparation of N-(5-Acenaphthyl)-N'-(1,2,3,4tetrahydroquinolinyl) guanidine.mesylate A mixture of 5-acenaphthyl cyanamide (582 mg, 3 mmol), 1,2,3,4 tetrahydroquinolinyl e mesylate (688 mg, 3 mmol), and chlorobenzene (2 mL) in a round bottom flask were heated at 150–160° C. for 1 hour and a precipitate formed. The precipitate was collected by filtration, washed with ether, and dried under vacuum to yield the pure product (1.25 g) as a white solid, mp: 203–204° C.; TLC: R$_f$=0.3 (SiO$_2$, CH$_2$Cl$_2$/MeOH=9/1); $^1$H NMR (CD$_3$OD): δ ppm 7.70–7.15 (m, ArH, 9H), 3.90 (t, CH$_2$, 2H), 3.443.35 (m, CH$_2$, 4H), 2.87 (t, CH$_2$, 2H), 2.69 (s, CH$_3$, 3H), 2.15 (m, CH$_2$, 2H); MS(EI): m/e 327.2 (M$^+$: C$_{22}$H$_{21}$N$_3$); Anal.: (C$_{23}$H$_{25}$N$_3$O$_3$S); Calcd. (%): C, 65.23, H, 5.95, N, 9.92; Found (%): C, 64.81, H, 6.00, N, 9.74.

EXAMPLE 8
Preparation of N,N'-Bis-(4-sec-butylphenyl)-2-iminopyrimidazolidine.HBr Part 1: Preparation of N,N'-Bis-(4-sec-butylphenyl) melonyldiamide Malonyldichloride (10 mmol) in methylene chloride (10 mL) was added dropwise to a solution of 4-sec-butylaniline (52 mmol) in methylene chloride (30 mL) over a period of 10 minutes at 4° C. After the exotherm subsided, the solution was removed from ice bath and stirred at 25° C. for 2 hours. The methylene chloride solution was concentrated down to dryness. The crude reaction mixture was purified by column chromatography (SiO$_2$, CH$_2$Cl$_2$/EtOAc=2/1) to yield the pure N,N'-bis-(4-sec-butylphenyl)melonyldiamide (75% in yield).

Part 2: Preparation of N,N'-Bis-(4-sec-butylphenyl)-1,3-diaminopropane

Diborane (38.24 mmol, 38.24 mL, 1M) in THF was added dropwise to a dry THF solution of N,N'-bis-(4-sec-butylphenyl)melonyldiamide (9.56 mmol) over 10 minutes at 4° C. After 15 minutes, the reaction mixture was heated at refluxing temperature for 16 hours. The reaction mixture was then quenched by aqueous HCl (1M) at 0° C. Then the THF was evaporated, and the solution was basified to pH 14 and extracted with CH$_2$Cl$_2$. The combined organic extracts were dried over MgSO$_4$, filtered, and concentrated to yield the pure N,N'-bis-(4-sec-butylphenyl)-1,3-diaminopropane as a yellow liquid (78% in yield).

Part 3: Preparation of N,N'-Bis-(4-sec-butylphenyl-2-imino-pyrimidazolidine.HBr

N,N'-bis-(4-sec-butylphenyl)-1,3-diaminopropane (1.69 g, 5 mmol) in EtOH (15 mL) was added cyanogen bromide, then the solution was brought to reflux for 16 hours. After the reaction, the mixture was concentrated down and purified by column chromatography (SiO$_2$, MeOH/CH$_2$Cl$_2$=0% to 10%). The pure N,N'-bis-(4-sec-butylphenyl)-2-imino-pyrimidazolidine.HBr was obtained as a white solid (75% in yield), mp: >250° C.; TLC: R$_f$=0.5 (SiO$_2$, CH$_2$Cl$_2$/MeOH= 9/1); MS(EI): m/e 363.2 (M$^+$: C$_{24}$H$_{33}$N$_3$); Anal.: (C$_{24}$H$_{33}$N$_3$.HBr.1/4H$_2$O); Calcd. (%): C, 64.17, H, 7.74, N, 9.40; Found (%): C, 64.18, H, 7.82, N, 9.19.

EXAMPLE 9
Preparation of N-N'-Bis(3-fluoroanthenyl)guanidine hydrobromide

To a solution of 3-aminofluoroanthene (1.95 g, 8.98 mmol) in ethanol (100.0 ml) was slowly added cyanogen bromide (0.922 g, 8.7 mmol) while the flask was surrounded by an ice bath and under static Ar. The solution was refluxed for 9.5 hours then let stir at room temperature for 18 hours. The yellow mixture was suction filtered and the yellow solid washed with ether and a little ethyl acetate to yield the title compound as a yellow solid, 1.53 g, 63.0% yield.

Yellow solid; mp: >300° C.; R$_f$=0.24 (10:1 CHCl$_3$/MeOH); $^1$H NMR (300 MHz, CD$_3$OD) d 8.10–8.55 (m, 6H, Ar—H), 7.94–8.00 (m, 4H, ArH), 7.73–7.85 (m, 4H, ArH), 7.39–7.42 (m, 4H, ArH); MS(EI): m/e 459 (M$^+$ for free base); Anal. Calcd. for C$_{33}$H$_{21}$N$_3$.HBr: C, 73.34, H, 4.1, N, 7.77; Found: C, 73.34, H, 4.48, N, 6.94, 6.76.

EXAMPLES 10–145

By methods indicated above and using appropriately substituted reagents, the following compounds were prepared having the specified physical characteristics.

EXAMPLE 10
N-(5-Acenaphthyl)-N'-[(1-naphthyl)-methylene] guanidine.CH$_3$SO$_3$H White solid; mp: 262° C.

EXAMPLE 11
N-($^2$-Naphthyl)-N'-(4-isopropylphenyl)guanidine.HCl

White solid; mp: 208–10° C.; $^1$H NMR (CDCl$_3$): δ 7.82–7.15 (m, 11H, ArH), 2.90–2.75 (m, 1H, —CH), 1.16 (d, 6H, J=6.84 Hz, 2× —CH$_3$); HRMS: 303.1738 (303.1735 Calcd. for C$_{20}$H$_{21}$N$_3$).

EXAMPLE 12
N,N'-Bis(2-fluorenyl)guanidine.HBr

White solid; mp: 281° C.

EXAMPLE 13
N,N'-Bis(4-tert-butylphenyl)guanidine

White solid; mp: 161–62° C.; TLC (CHCl$_3$:CH$_3$OH; 9:1): R$_f$=0.54; $^1$H NMR (CDCl$_3$): δ 7.34 (d, 4H, J=8.57 Hz, ArH), 7.05 (d, 4H, J=8.52 Hz, ArH), 1.28 (s, 18H, 2× —CH$_3$); HRMS: 323.2372 (323.2362 Calcd. for C$_{21}$H$_{29}$N$_3$).

EXAMPLE 14
N-(4-tert-Butylphenyl)-N'-(2,3,4-trichlorophenyl) guanidine.HCl

White solid; mp: 227–29° C.; TLC (CH$_2$Cl$_2$:CH$_3$OH; 9:1): R$_f$=0.43; $^1$H NMR (CD$_3$OD): δ 7.63 (d, 1H, J=8.7 Hz, ArH), 7.52 (d, 2H, J=8.67 Hz, ArH), 7.44 (d, 1H, J=8.67 Hz, ArH), 7.27 (d, 2H, J=8.66 Hz, ArH), 1.33 (s, 9H, 3× —CH$_3$); Anal. Calcd. for C$_{17}$H$_{18}$N$_3$Cl.HCl (414.17): C, 50.15; H, 4.7; N, 10.32. Found: C, 49.97; H, 4.57; N, 10.22.

EXAMPLE 15
N-(4-Methoxy-1-naphthyl)-N'-(2,3,4-trichlorophenyl) guanidine.HCl White solid; mp: 238–40° C.; TLC (CH$_2$Cl$_2$:CH$_3$OH; 9:1): R$_f$=0.48; $^1$H NMR (CD$_3$OD): δ 8.45 (d, 1H, J=8.43 Hz, ArH), 8.08 (d, 1H, J=8.24 Hz, ArH), 7.82–7.63 (m, 5H, ArH), 7.13 (d, 1H, J=8.27 Hz, ArH), 4.19 (s, 3H, —OCH$_3$); Anal. Calcd. for C$_1$H$_{14}$N$_3$Cl$_3$.HCl (431.14): C, 50.14; H, 3.51; N, 9.75.; Found: C, 49.38; H, 3.59; N, 9.57.

EXAMPLE 16
N-(2-Naphthyl)-N'-(2-adamantyl)guanidine.HCl

White solid; mp: 219–20° C.; $^1$H NMR (CDCl$_3$): δ 7.81–7.22 (m, 7H, ArH), 1.97–1.51 (m, 15H, ArH); Anal. Calcd. for $_{21}$H$_{25}$N$_3$.HCl (355.45): C, 70.90; H, 7.31; N, 11.82; Found: C, 70.90, H, 7.34; H, 11.73.

EXAMPLE 17
N-(4-sec-Butylphenyl)-N-benzylguanidine mp: 65–67° C.; TLC: R$_f$=0.5 (SiO$_2$, CH$_2$Cl$_2$/MeOH=9/1); $^1$H NMR (CD$_3$OD): δ 7.30–6.90 (m, ArH, 9H), 4.98 (s, CH$_2$, 2H), 2.58 (m, CH, 1H, 1.55 (m, CH$_2$, 2H), 1.20 (d, CH$_3$, 3H), 0.79 (t, CH$_3$, 3H); HRMS: 281.1891 (281.1891 calculated for C$_{18}$H$_{23}$N$_3$).

EXAMPLE 18
N-(5-Acenaphthyl)-N-benzylguanidine mp: 138–140° C.; TLC: R$_f$=0.5 (SiO$_2$, CH$_2$Cl$_2$/MeOH=9/1); $^1$H NMR (CD$_3$OD): 67 7.45–6.93 (m, ArH, 10H), 5.54 (d, CH$_2$, J=15.8 Hz, 1H), 4.63 (d, CH$_2$, J=15.6 Hz, 1H), 3.45–3.40 (m, CH$_2$, 4H); HRMS: 301.1559 (301.1589 calculated for C$_{20}$H$_{19}$N$_3$).

EXAMPLE 19
N-(5-Acenaphthyl)-N-(4-isopropylbenzyl)guanidine mp: 153–155° C.; TLC: R$_f$=0.3 (SiO$_2$, CH$_2$Cl$_2$/MeOH=9/1); $^1$H NMR (CD$_3$OD): δ ppm 7.60–7.10 (m, ArH, 9H), 5.17 (d, CH$_2$, J=16.2 Hz, 1H), 4.57 (d, CH$_2$, J=16.1 Hz, 1H), 3.45–3.40 (m, CH$_2$, 4H), 2.85 (m, CH, 1H), 1.20 (d, CH$_3$, 6H); HRMS: 343.2048 (343.2067 calculated for C$_{23}$H$_{25}$N$_3$); HPLC: 92% pure.

EXAMPLE 20
N-(4-Cyclohexylphenyl)-N-(4-isopropylbenzyl)guanidine.HCl mp: 130–131° C.; TLC: R$_f$=0.4 (SiO$_2$, CH$_2$Cl$_2$/MeOH=9/1); $^1$H NMR (CD$_3$OD): δ ppm 7.35–7.12 (m, ArH, 8H), 4.92 (s. CH$_2$, 2H), 2.90 (m, CH, 1H), 2.53 (m, CH, 1H), 1.87–1.25 (m, CH$_2$, 10H), 1.12 (d, CH$_3$, 6H); HRMS: 349.2512 (349.2518 calculated for C$_{23}$H$_{31}$N$_3$); HPLC: 99% pure.

EXAMPLE 21
N-(4-Cyclohexylphenyl)-N-(4-tert-butylbenzyl)guanidine.HCl mp: 219–220° C.; TLC: R$_f$=0.4 (SiO$_2$, CH$_2$Cl$_2$/MeOH=9/1); $^1$H NMR (CDCl$_3$): δ ppm 7.45–7.18 (m, ArH, 8H), 4.88 (s, CH$_2$, 2H), 2.55 (s, CH, 1H), 1.90–1.30 (m, CH$_2$, 10H), 1.32 (s, CH$_3$, 9H); MS(EI): m/e 363.2 (M$^+$: C$_{24}$H$_{33}$N$_3$); Anal.: (C$_{24}$H$_{33}$N$_3$.HCl); Calcd. (%): C, 72.06, H, 8.57, N, 10.50; Found (%): C, 71.97, H, 8.32, N, 10.33.

EXAMPLE 22
N-(2-Fluorenyl)-N-(4-tert-butylbenzyl)guanidine.HCl mp: 155–157° C.; TLC: R$_f$=0.6 (SiO$_2$, CH$_2$Cl$_2$/MeOH=9/1); $^1$H NMR (CDCl$_3$): δ 7.90–7.20 (m, ArH, 11 H), 4.95 (s, CH$_2$, 2H), 3.95 (s, CH$_2$, 2H), 1.32 (s, CH$_3$, 9H); MS(EI): m/e 369.2 (M$^+$: C$_{25}$H$_{27}$N$_3$); Anal.: (C$_{25}$H$_{27}$N$_3$.HCl.H$_2$O); Calcd. (%): C, 70.89, H, 7.14, N, 9.93; Found (%): C, 71.14, H, 6.88, N, 9.77.

EXAMPLE 23
N-(4-sec-Butylphenyl)-N-(trans-cinnamyl)guanidine.HCl mp: 169–170° C.; TLC: R$_f$=0.2 (SiO$_2$, CH$_2$Cl$_2$/MeOH=9/1); $^1$H NMR (CDCl$_3$): δ ppm 7.40–7.20 (m, ArH, 9H), 6.68 (d, CH, J=16 Hz, 1H), 6.25 (dt, CH, J=16 Hz, 1H), 4.55 (d, CH$_2$, 2H), 2.66 (m, CH, 1H), 1.60 (m, CH$_2$, 2H), 1.25 (d, CH$_3$, 3H), 0.83 (t, CH$_3$, 3H); Anal.: (C$_{20}$H$_{25}$N$_3$.HCl); Calcd. (%): C, 69.93, H, 7.64, N, 12.24; Found (%): C, 69.79, H, 7.45, N, 12.29.

EXAMPLE 24
N-(4-n-Butoxyphenyl)-N-(4-tert-butylbenzyl)guanidine.HCl mp: 188–189° C.; TLC: R$_f$=0.5 (SiO$_2$, CH$_2$Cl$_2$/MeOH=9/1); 1H NMR (CDCl$_3$): δ ppm 7.44–6.90 (m, ArH, 8H), 4.84 (s, CH$_2$, 2H), 3.97 (t, CH$_2$, 2H), 1.73 (p, CH$_2$, 2H), 1.49 (p, CH$_2$, 2H), 1.32 (s, CH$_3$, 9H), 0.94 (t, CH$_3$, 3H); MS(EI): m/e 353.3 (M$^+$: C$_{22}$, H$_{31}$N$_3$O); Anal.: (C$_{22}$H$_{31}$N$_3$O.HCl); Calcd. (%): C, 67.83, H, 8.29, N, 10.79; Found (%): C, 68.00, H, 8.18, N, 11.04.

EXAMPLE 25
N-($^3$-Biphenyl)-N-(4-tert-butylbenzyl)guanidine.HCl mp: 255–256° C.; TLC: R$_f$=0.5 (SiO, CH$_2$Cl$_2$/MeOH=9/1); $^1$H NMR (CDCl$_3$): δ 7.70–7.15 (m, ArH, 13H), 4.93 (s, CH$_2$, 2H), 1.30 (s, CH$_3$, 9H); MS(EI): m/e 357.3 (M$^+$: C$_{24}$H$_{27}$N$_3$); Anal.: (C$_{24}$H$_{27}$N$_3$.HCl); Calcd. (%): C, 73.25, H, 7.18, N, 10.68; Found (%): C, 73.41, H, 7.18, N, 10.86.

EXAMPLE 26
N-(5-Indanyl)-N-(4-tert-butylbenzyl)guanidine.HCl

TLC: R$_f$=0.5 (SiO$_2$, CH$_2$Cl$_2$/MeOH=9/1); $^1$H NMR (CDCl$_3$): δ ppm 7.45–6.90 (m, ArH, 7H), 4.86 (s, CH$_2$, 2H), 2.87 (m, CH$_2$, 4H), 2.08 (m, CH$_2$, 2H), 1.29 (s, CH$_3$, 9H); MS(EI): m/e 321.2 (M$^+$: C$_{21}$H$_{27}$N$_3$).

EXAMPLE 27
N-(3-Trifluoromethoxyphenyl)-N-(4-tert-butylbenzyl)guanidine.HCl

TLC: R$_f$=0.5 (SiO$_2$, CH$_2$Cl$_2$/MeOH=9/1); $^1$H NMR (CDCl$_3$): δ ppm 7.65–7.10 (m, ArH, 8H), 4.94 (s, CH$_2$, 2H), 1.29 (s, CH$_3$, 9H); MS(EI): m/e 365.1 (M$^+$: C$_{19}$H$_{22}$F$_3$N$_3$O).

EXAMPLE 28
N-(Methoxy-1-naphthyl)-N-(4-tert-butylbenzyl) guanidine.HCl

TLC: R$_f$=0.5 (SiO$_2$, CH$_2$Cl$_2$/MeOH=9/1); $^1$H NMR (CDCl$_3$: δ ppm 8.35–6.80 (m, ArH, 10H), 5.25 (d, CH$_2$, J=15.6 Hz, 1H), 4.59 (d, CH$_2$, J=15.6 Hz, 1H), 1.29 (s, CH$_3$, 9H); MS(EI): m/e 361.5 (M$^+$: C$_{23}$H$_{27}$N$_3$O).

EXAMPLE 29
N-(5-Acenaphthyl)-N'-(indolinyl)guanidine.mesylate mp: 249–250° C.; TLC: R$_f$=0.3 (SiO$_2$, CH$_2$Cl$_2$/MeOH=9/1); $^1$H NMR (CD$_3$OD): δ ppm 7.70–7.15 (m, ArH, 9H), 4.27 (t, CH$_2$, 2H), 3.44–3.35 (m, CH$_2$, 4H), 3.30 (t, CH$_2$, 2H), 2.69 (s, CH$_3$, 3H); MS(EI): m/e 313.2 (M$^+$: C$_{21}$H$_{19}$N$_3$); Anal.: (C$_{22}$H$_{23}$N$_3$O$_3$S.1/2H$_2$O); Calcd. (%): C, 63.13, H, 5.78, N, 10.04; Found (%): C, 63.13, H, 5.70, N, 10.06.

EXAMPLE 30
N,N'-Bis(3-biphenyl)guanidine.HBr

White solid; mp: 176–178° C.; TLC(CH$_2$Cl$_2$:CH$_3$OH; 15:1): R$_f$=0.50; $^1$H NMR (CD$_3$OD): 7.66–7.33 (m, ArH). Anal. Calcd. for C$_{25}$H$_{33}$N$_3$.HBr (444.37): C, 67.27; H, 5.42; N, 9.41.; Found: C, 67.01, H, 4.86, N, 9.29.

EXAMPLE 31
N,N'-Di-(3-tert-butylphenyl)guanidine.HBr

White solid; mp: 206–208° C.; TLC (CH$_2$CL$_2$: MeOH; 15:1): R$_f$=0.50; $^1$H NMR (CD$_3$OD): 7.53–7.23 (m, 8H, ArH), 1.34 (s, 18H, —C(CH$_3$)$_3$); Anal. Calcd. for C$_{21}$H$_{29}$N$_{32}$.HBr (404.39): C, 62.37, H, 7.48, N, 10.39; Found: C, 62.49, H, 7.45, N, 10.52.

EXAMPLE 32
N,N'-Bis-(4-methoxy-1-naphthyl)guanidine.HBr

Light green solid; mp: 236–238° C.; TLC (CH$_2$CL$_2$:MeOH; 15:1): R$_f$=0.48; $^1$H NMR (CD$_3$OD): 8.32 (d, 2H, J=7.72 Hz, ArH), 7.97 (d, 2H, J=8.18 Hz, ArH), 7.69 (t, 2H, J=7.52 Hz, ArH), 7.57 (q, 4H, J=7.52 Hz, ArH), 7.00 (d, 2H, J=8.18 Hz, ArH), 4.05 (s, 3H, —OCH$_3$); Anal. Calcd. for C$_{23}$H$_{21}$N$_3$O$_2$.HBr (452.35): C, 61.07, H, 4.90, N, 9.29; Found: C, 60.98, H, 4.99, N, 9.50.

EXAMPLE 33
N,N'-Bis-(5-indanyl)guanidine.HBr

White solid; mp: 118–120° C.; TLC (CH$_2$Cl$_2$:MeOH; 15:1): R$_f$=0.31; $^1$H NMR (CD$_3$OD): 7.30 (d, J=8.25 Hz, 2H, ArH), 7.18 (s, 2H, ArH), 7.07 (d, 2H, J=7.27 Hz, ArH), 2.93 (q, J=7.10 Hz, 8H, —CH$_2$), 2.11 (p, 4H, —CH$_2$, J=7.42 Hz); Anal. Calcd. for Cl$_{19}$H$_{21}$N$_3$.HBr (372.31): C, 61.30, H, 5.96, N, 11.29; Found: C, 61.12; H, 5.81; N, 11.11.

EXAMPLE 34
N,N'-Bis-(3-sec-butylphenyl)guanidine.HBr

White solid; mp: 85–87° C.; TLC(CH$_2$Cl$_2$:MeOH; 15:1): R$_f$=0.31; $^1$H NMR (CD$_3$OD): 7.39 (t, J=7.57 Hz, 2H, ArH), 7.17 (t, J=7.15 Hz, 4H, ArH), 2.65 (m, 2H, —CH), 1.64 (m, 4H, —CH$_2$), 1.58 (d, J=0.82 Hz, 6H, —CH$_3$), 0.84 (t, J=1.90 Hz, 6H, —CH$_3$); Anal. Calcd. for C$_{21}$H$_{29}$N$_3$.HBr (404.39): C, 62.37, H, 7.29, N, 10.39; Found: C, 62.58, H, 7.29, N, 10.61.

EXAMPLE 35
N,N'-Bis(4-tert-butylphenyl)-N-methylguanidine.HBr

White solid; mp: 194–196° C.; TLC (CH$_2$Cl$_2$: MeOH; 10:1): R$_f$=0.35; $^1$H NMR (CD$_3$OD): 7.60–7.57 (d, J=8.39 Hz, 2H, ArH), 7.51–7.48 (d, J=8.24 Hz, 2H, ArH), 7.38–7.35 (d, J=8.52 Hz, 2H, ArH), 7.22–7.20 (d, J=8.24 Hz, 2H, ArH), 3.46 (s, 1H, —CH$_3$), 1.35 (s, 9H, —C(CH$_3$)$_3$), 1.33 (s, 9H, —C(CH$_3$)$_3$); Anal. Calcd. for C$_{22}$H$_3$,N$_3$.HCl(373.97): C, 70.66, H, 8.62, N, 11.29; Found: C, 70.69, H, 8.31, N, 11.39.

EXAMPLE 36
N,N'-Bis(4-tert-butylphenyl)-N,N'-methylguanidine-HBr

White solid; mp: 175–177° C.; TLC(CH$_2$Cl$_2$:MeOH; 10:1): R$_f$=0.39; $^1$H NMR (CD$_3$OD): 7.21–7.18 (d, J=8.52 Hz, 4H, ArH), 6.80–6.78 (d, J=8.51 Hz, 4H, ArH), 3.35 (s, 6H, —CH$_3$), 1.26 (s, 18H, —C(CH$_3$)$_3$); Anal. Calcd. for C$_{23}$H$_{33}$N$_3$.HCl(388.00): C, 71.20, H, 8.83, N, 10.83; Found: C, 70.88, H, 8.61, N, 10.75.

EXAMPLE 37
N,N'-Bis(4-n-butylphenyl)guanidine-mesylate

White solid: M.P. 120–22° C.; $^1$H NMR (300 MHz, CD$_3$OD): δ 7.28 (dd, 4H, J=8.5 Hz and J=2.2 Hz, ArH); 7.23 (dd, 4H, J=8.5 Hz and J=2.2 Hz, ArH); 2.69 (s, 3H, —SO$_3$H—CH$_3$); 2.64 (t, 4H, J=7.69 Hz, 2× ArCH$_2$—); 1.65–1.55 (m, 4H, 2× —CH$_2$—CH$_2$CH$_3$); 1.43–1.30 (m, 4H, 2× —CH$_2$—CH$_3$); 0.94 (t, 6H, J=7.35 Hz, 2× —CH$_3$); Anal Calcd. for C$_{21}$H$_{29}$N$_{30}$CH$_4$SO$_3$ (419.56): C, 62.98, H. 7.93, N, 10.01; Found: C, 62.96, H, 7.69, N, 9.93.

EXAMPLE 38
N-(5-Acenaphthyl)-N'-(1-methyl-2-phenoxyethyl) guanidine.HCl ((5-C$_{12}$H$_9$)NHC(=NH)NHCH(CH$_3$)CHOC$_6$H$_5$.HCl)

Bubbly white solid: mp: 107–1 10° C.; R$_f$=0.24 (10:1 CHCl$_3$MeOH); $^1$H NMR (300 MHz, CD$_3$OD): δ 7.29–7.56 (m, 7H, ArH), 6.96–7.01 (t, 3H, J=16 Hz, ArH), 4.20–4.32 (m, 1H, CH), 4.11–4.89 (m, 1H, CH), 3.90–4.00 (m, 1H, CH), 3.40–3.50 (m, 4H, CH$_2$); MS(EI): m/e 345 (M$^+$ for free base); Anal. Calcd. for C$_{22}$H$_{23}$N$_3$O.HCl: C, 69.19, H, 6.33, N, 11.00; Found: C, 69.07, H, 6.40, N, 10.87.

EXAMPLE 39
N-(5-Acenaphthyl)-N'-(piperonyl)guanidine.HCl

Tan solid: mp: 142–144° C.; R$_f$=0.20 (10:1 CHCl$_3$/MeOH); $^1$H NMR (300 MHz, CD$_3$OD): 5 7.347.54 (m, 5H, ArH), 6.84 (s, 3H, ArH), 5.98 (s, 2H, CH$_2$), 4.41 (s, 2H, CH$_2$), 3.43–3.50 (m, 4H, 2-CH$_2$); MS(EI): m/e 345 (M$^+$ for free base); Anal. Calcd. for C$_{21}$H$_{19}$N$_3$O$_2$.HCl.0.5C$_4$H$_8$O$_2$: C, 64.92, H, 5.69, N, 9.88; Found: C, 64.37, H, 5.93, N, 10.25.

EXAMPLE 40
N-(5-Acenaphthyl)-N'-(1-methyl-2-(4-chlorophenyl)ethyl) guanidine.HCl ((5-C$_{12}$H$_9$)NHC(=NH)NHCH(CH$_3$)CH(4-ClC$_6$H$_4$).HCl)

Bubbly amber solid: M.P. 123–125° C.; R$_f$=0.22 (10:1 CHCl$_3$/MeOH); $^1$H NMR (300 MHz, CD$_3$OD): δ 7.51–7.54 (m, 1H, ArH), 7.18–7.37 (m, 8H, ArH), 4.00–4.12 (m, 1H, CH), 3.41–3.51 (m, 4H, 2-CH$_2$), 2.90–3.00 (dd, 1H, CH), 2.71–2.82 (dd, 1H, CH) 1.33–1.35 (d, 3H, J=6.53 Hz, CH$_3$); MS(EI): m/e 363 (M$^+$ for free base); Anal. Calcd. for C$_{22}$H$_{22}$N$_3$Cl.HCl: C, 66.00, H, 5.79, N, 10.50; Found: C, 65.94, H, 5.91, N, 10.30.

EXAMPLE 41
N-(5-Acenaphthyl)-N'-(1,2-diphenylethyl)guanidine.HCl

Cream colored solid: M.P. 167–170° C.; R$_f$=0.18 (10:1 CHCl$_3$/MeOH); $^1$H NMR (300 MHz, CD$_3$OD): δ 7.16–7.44 (m, 15H, ArH), 5.1–5.2 (m, 1H, CH) 3.30–3.41 (m, 4H, 2-CH$_2$), 3.13–3.30 (m, 2H, CH$_2$); MS(EI): m/e 391 (M$^+$ for free base); Anal. Calcd. for $_{27}$H$_{25}$N$_3$.HCl: C, 75.77, H, 6.12, N, 9.82; Found: C, 75.60, H, 6.00, N, 9.71.

EXAMPLE 42
N-(3-Benzyloxyphenyl)-N'-(4-benzyloxyphenyl) guanidine.HCl

Bubbly pink solid: mp: 59–62° C.; R$_f$=0.19 (10:1 CHCl$_3$/MeOH); $^1$H NMR (300 MHz, CD$_3$OD): δ 7.24–7.45 (m, 13H, ArH), 6.90–7.10 (m, 5H, ArH), 5.12 (brs, 4H, 2-CH$_2$); MS(EI): m/e 423 (M$^+$ for free base); Anal. Calcd. for C$_{27}$H$_{25}$N$_3$O$_2$.HCl.1.5H$_2$O: C, 66.64, H, 6.01, N, 8.64; Found: C, 67.21, 66.95, H, 6.12, 6.01, N, 8.25, 7.98.

EXAMPLE 43
N-(5-Acenaphthyl)-N'-(3-phenylpropyl)guanidine.HCl

White solid: mp: 84° C.; R$_f$=0.28 (1:5 MeOH:EtOAc); $^1$H NMR (300 MHz, CD$_3$OD): δ 7.54–7.57 (m, 2H, ArH), 7.35–7.41 (m, 3H, ArH), 7.25–7.35 (m, 2H, ArH), 7.18–7.24 (m, 3H, ArH), 3.40–3.48 (brs, 4H, 2-CH$_2$), 3.29–3.34 (t, J=7 Hz, 2H, CH$_2$-N), 2.66–2.71 (t, J=8 Hz, 2H, CH$_2$), 1.91–2.00 (m, 2H, CH$_2$—Ar); MS(EI): m/e 329 (M$^+$ for free base); Anal. Calcd. for C$_{24}$H$_{21}$N$_3$.HCl.0.5H$_2$O: C, 70.48, H, 6.72, N, 11.26; Found: C, 70.52, H, 6.65, N, 11.18.

EXAMPLE 44

N-(5-Acenaphthyl)-N'-(2-methyl-2-phenylethyl) guanidine.HCl

White solid: mp: 110° C.; $R_f$=0.26 (1:5 MeOH:EtOAc); $^1$H NMR (300 MHz, CD$_3$OD): δ 7.49–7.54 (t, J=7 Hz, 1H, ArH), 7.24–7.38 (m, 8H, ArH), 7.15–7.18 (m, 1H, ArH), 3.51–3.53 (d, J=6 Hz, 2H, CH$_2$—Ar), 3.38–3.48 (m, 4H, 2-CH$_2$), 3.03–3.10 (m, 1H, CH), 1.30–1.33 (d, J=7 Hz, 3H, CH$_3$); MS(EI): m/e 329 (M$^+$ for free base); Anal. Calcd. for C$_{24}$H$_{21}$N$_3$.HCl.0.5H$_2$O: C, 70.48, H, 6.72, N, 11.26; Found: C, 70.62, H, 6.58, N, 11.17.

EXAMPLE 45

N,N'-(sec-Butylphenyl)-N'-(2-phenoxyethyl)guanidine.HCl

Semisolid: $R_f$=0.20 (1:5 MeOH:EtOAc); $^1$H NMR (300 MHz, CD$_3$OD): δ 7.22–7.34 (m, 6, ArH), 7.16–7.22 (d, J=7 Hz, 2, ArH), 7.00–7.07 (d, J=7 Hz, 2H, ArH), 6.87–6.98 (m, 3H, ArH), 4.20 (brs, 4H, 2-CH$_2$), 2.51–2.70 (m, 2H, 2-CH), 1.53–1.68 (m, 4H, 2-CH$_2$), 1.20–1.27 (2d, J=6 Hz, 6H, 2-CH$_3$); MS(EI): m/e 444 (M$^+$ for free base); Anal. Calcd. for C$_{29}$H$_{37}$N$_3$.0.75HCl: C, 73.96, H, 8.08, N, 8.92; Found: C, 74.21, H, 8.26, N, 9.21.

EXAMPLE 46

N,N'-(sec-Butylphenyl)-N'-(n-pentyl)guanidine.HCl

White solid: $R_f$=0.17 (1:5 MeOH:EtOAc); $^1$H NMR (300 MHz, CD$_3$OD): δ 7.31–7.38 (m, 4H, ArH), 7.25–7.28 (d, J=8.5 Hz, 2H, ArH), 7.16–7.19 (d, J=8.5 Hz, 2H, ArH), 3.75–3.80 (t, J=8 Hz, 2H, N—CH$_2$), 2.59–2.71 (m, 2H, 2-CH), 1.56–1.68 (m, 6H, 3-CH$_2$), 1.30–1.34 (m, 4H, 2-CH$_2$), 1.22–1.26 (2d, J=7 Hz, 6H, 2-CH$_3$), 0.80–0.91 (m, 9H, 3-CH$_3$); MS(EI): m/e 394 (M$^+$ for free base); Anal. Calcd. for C$_{26}$H$_{39}$N$_3$.HCl.H$_2$O: C, 69.69, H, 9.45, N, 9.38; Found: C, 69.89, H, 8.88, N, 10.09.

EXAMPLE 47

N-(1-Naphthyl)-N-(4-tert-butylbenzyl)guanidine.HCl $^1$H NMR (CDCl$_3$): δ ppm 8.35–7.10 (m, ArH, 11H), 5.25 (d, CH$_2$, J=15.6 Hz, 1H), 4.67 (d, CH$_2$, J=15.6 Hz, 1H), 1.29 (s, CH$_3$, 9H). MS(EI): m/e 331 (M$^+$: C$_{22}$H$_{25}$N$_3$); Anal. (C$_{22}$H$_2$,N$_3$.HCl): Calcd. (%): C, 71.82, H, 7.12, N, 11.42; Found (%): C, 71.79, H, 7.12, N, 11.43; TLC: $R_f$=0.50 (SiO$_2$, CH$_2$Cl$_2$/MeOH=9/1); mp: 241–242° C.

EXAMPLE 43

N-(3-Iodophenyl)-N-(4-tert-butylbenzyl)guanidine.HCl $^1$H NMR (CD$_3$OD): δ ppm 7.78–7.13 (m, ArH, 8H), 4.87 (s, ArCH$_2$, 2H), 1.30 (s, CH$_3$, 9H); MS(EI): m/e 407.3 (M$^+$: C$_{18}$H$_{22}$N$_3$I); Anal. (C$_{18}$H$_{22}$IN$_3$.HCl): cal.(%): C, 48.72, H, 5.22, N. 9.47; found (%): C, 48.90, H, 5.46, N, 9.52; TLC: $R_f$=0.42 (SiO$_2$, CH$_2$Cl$_2$/MeOH=10/1); mp: 271–272° C.

EXAMPLE 49

N-(4-Chloro-1-naphthyl)-N-(4-tert-benzyl)guanidine.HCl $^1$H NMR (CD$_3$OD): δ ppm 8.37–7.13 (m, ArH, 10H), 5.25 (d, CH$_2$, J=15.5 Hz, 1 H), 4.69 (d, CH$_2$, J=15.4 Hz, 1 H), 1.26 (s, CH$_3$, 9H); MS(EI): m/e 365.1 (M$^+$: C$_{22}$H$_{24}$ClN$_3$); Calcd. (C$_{22}$H$_{24}$ClN$_3$.HCl.H$_2$O): Calcd. (%): C, 62.86, H, 6.47, N, 10.03; Found (%): C, 63.19, H, 6.27, N, 9.69; TLC: $R_f$=0.52 (SiO$_2$, CH$_2$Cl$_2$/MeOH=10/1); mp: 115–117° C.

EXAMPLE 50

N-(4-tert-Butylphenyl)-N-(4-tert-butyl benzyl)guanidine.HCl $^1$H NMR (CDCl$_3$): δ ppm 7.51–7.18 (m, ArH, 8H), 4.93 (s, ArCH$_2$, 2H), 1.33 (s, CH$_3$, 9H), 1.31 (s, CH$_3$, 9H); MS(EI): m/e 338 (M$^+$: C$_{22}$H$_{31}$N$_3$); Anal. (C$_{22}$H$_{31}$N$_3$.HCl): Calcd. (%): C, 70.66, H, 8.62, N, 11.24; Found (%): C, 70.43, H, 8.42, N, 11.17; TLC: $R_f$=0.45 (502, CH$_2$Cl$_2$/MeOH=1011); mp: 290–291 IC.

EXAMPLE 51

N-(4-Iodophenyl)-N-(4-tert-butylbenzyl)guanidine.HCl $^1$H NMR (CD$_3$OD): δ ppm 7.81–7.02 (m, ArH, 8H), 4.89 (s, ArCH$_2$, 2H), 1.30 (s, CH$_3$, 9H); MS(EI): m/e 408 (M$^+$: Cl$_8$H$_{22}$N$_3$1); Anal. (C$_{18}$H$_{22}$IN$_3$.HCl): Calcd. (%): C, 48.72, H, 5.22, N, 9.47; Found (%): C, 48.72, H, 5.26, N, 9.28; TLC: $R_f$=0.45 (SiO$_2$, CH$_2$Cl$_2$/MeOH=1011); mp: 219–220° C.

EXAMPLE 52

N-(1-Naphthylmethyl)-N-(4-tert-butylbenzyl)guanidine.HCl ((1-C$_{10}$H$_7$CH$_2$)(4(C(CH$_3$)$_3$C$_6$H$_4$CH$_2$)NC(=NH)NH$_2$).HCl)

$^1$H NMR (CDCl$_3$): δ ppm 7.95–7.10 (m, ArH, 11H), 5.10 (s, CH$_2$, 2H), 4.58 (s, CH$_2$, 2H), 1.32 (s, CH$_3$, 9H); MS(EI): m/e 346 (M$^+$: C$_{23}$H$_{27}$N$_3$); Anal. (C$_{23}$H$_{27}$N$_3$.HCl.H$_2$O): Calcd. (%): C, 69.07, H, 7.56, N, 10.51; Found (%): C, 68.70, H, 7.71, N, 10.19; TLC: $R_f$=0.50 (SiO$_2$, CH$_2$Cl$_2$/MeOH=9/1); mp: 134–135° C.

EXAMPLE 53

N-(5-Acenaphthyl)-N-(3-phenoxybenzyl)guanidine.HCl $^1$H NMR (CD$_3$OD): δ ppm 7.62–6.80 (m, ArH, 14H), 5.20 (d, CH$_2$, J=15.7 Hz, 1H), 4.70 (d, CH$_2$, J=15.9 Hz, 1H), 3.46–3.40 (m, CH$_2$, 4H); MS(EI): m/e 393.5 (M$^+$: C$_{28}$H$_{23}$ON$_3$); Anal. (C$_2$,H$_{23}$ON$_3$.HCl): Calcd. (%): C, 72.63, H, 5.63, N, 9.77; Found (%): C, 72.77, H, 5.57, N, 9.67; TLC: $R_f$=0.45 (SiO$_2$, CH$_2$Cl$_2$/MeOH=10/1); mp: 100–101° C.

EXAMPLE 54

N-(3-Trifluoromethylphenyl)-N-(4-tert-butyl benzyl)guanidine.HCl $^1$H NMR (CD$_3$OD): δ 7.63–7.13 (m, ArH, 8H), 4.92 (s, ArCH$_2$, 2H), 1.29 (s, CH$_3$, 9H); MS(EI): m/e 349.1 (M$^+$: C$_{19}$H$_{22}$F$_3$N$_3$); Anal. (C$_{19}$H$_{22}$F$_3$N$_3$.HCl): Calcd. (%): C, 59.14, H, 6.01, N, 10.89; Found (%): C, 59.14, H, 6.12, N, 10.88; TLC: RI=0.$^{49}$ (S502, CH$_2$Cl$_2$/MeOH=10/1); mp: 281–282° C.

EXAMPLE 55

N-(3-Methylthiophenyl)-N-(4-tert-butyl benzyl)guanidine.HCl $^1$H NMR (CD$_3$OD): δ ppm 7.42–7.15 (m, ArH, 8H), 4.87 (s, ArCH$_2$, 2H), 235 (s, SCH$_3$, 3H), 1.30 (s, CH$_3$, 9H); MS(EI): m/e 327.3 (M$^+$: C$_1$H$_{25}$SN$_3$); Anal. (C$_{19}$H$_{25}$SN$_3$.HCl): Calcd. (%): C, 62.70, H, 7.20, N, 11.55; Found (%): C, 62.81, H, 7.27, N, 11.57; TLC: $R_f$=0.37 (SiO$_2$, CH$_2$Cl$_2$/MeOH=10/1); mp: 247–248° C.

EXAMPLE 56

N-(5-Acenaphthyl)-N-(3-iodobenzyl)guanidine-HCl $^1$H NMR (CDCl$_3$): δ ppm 7.62–7.00 (m, ArH, 9H), 5.46 (d, CH$_2$, J=0.55 Hz, 1H), 4.75 (d, CH$_2$, J=1.98 Hz, 1H), 3.49–3.42 (m, CH$_2$, 4H); MS(EI): m/e 427.1 (M$^+$: C$_{20}$H$_{18}$IN$_3$); Anal. (C$_{20}$H$_{18}$IN$_3$.HCl): Calcd. (%): C, 51.80, H, 4.13, N, 9.06; Found (%): C, 52.00, H, 4.14, N, 9.00; TLC: $R_f$=0.46 (SiO$_2$, CH$_2$Cl$_2$/MeOH=10/1); mp: 249–250° C.

EXAMPLE 57

N-(5-Acenaphthyl)-N-(cinnamyl)guanidine.HCl $^1$H NMR (CDCl$_3$): δ ppm 7.62–7.18 (m, ArH, 10H), 6.65 (d, CH$_2$, J=15.66 Hz, 1 H), 6.30 (dd, CH$_2$, J=15.5 Hz, 1 H), 5.27 (m, =CH, 0.5H), 4.92 (m, =CH, 0.5H), 4.40 (m, =CH, 1H), 3.57–3.41 (m, CH$_2$, 4H); MS(EI): m/e 327.2 (M$^+$: C$_{22}$H$_{21}$N$_3$); Anal. (C$_{22}$H$_2$IN$_3$.HCl·3/4H$_2$O): Calcd. (%): C, 70.01, H, 6.27, N, 11.13; Found (%): C, 70.21, H, 6.31, N, 11.10; TLC: R$_f$=0.46 (SiO$_2$, CH$_2$Cl$_2$/MeOH=10/1); mp: 205–206.5° C.

EXAMPLE 58
N-(5-Acenaphthyl)-N-(4-iodobenzyl)guanidine.HCl $^1$H NMR (CD$_3$OD): δ ppm 7.65–7.00 (m, ArH, 9H), 5.20 (d, CH$_2$, J=15.7 Hz, 1H), 4.70 (d, CH$_2$, J=15.9 Hz, 1H), 3.46–3.40 (m, CH22, 4H); MS(EI): m/e 427.2 (M$^+$: C$_{20}$H$_{18}$IN$_3$); Anal. (C$_{20}$H$_{18}$IN$_3$.HCl·3/2H$_2$O): Calcd. (%): C, 48.95, H, 4.52, N, 8.56; Found (%): C, 48.62, H, 4.42, N, 8.39; TLC: R$_f$=0.43 (SiO$_2$, CH$_2$Cl$_2$/MeOH=10/1); mp: 269–270° C.

EXAMPLE 59
N-(5-Acenaphthyl)-N-(4-trifluoromethoxy benzyl)guanidine.HCl $^1$H NMR (CD$_3$OD): δ ppm 7.56–7.17 (m, ArH, 9H), 5.25 (d, CH$_2$, J=15.9 Hz, 1 H), 4.82 (d, CH$_2$, J=15.7 Hz, 1 H), 3.43–3.41 (m, CH$_2$, 4H); MS(EI): m/e 385.3 (M$^+$: C$_{21}$H$_{18}$F$_3$ON$_3$); Anal. (C$_{21}$H$_{18}$F$_3$ON$_3$.HCl·2H$_2$O): Calcd. (%): C, 55.09, H, 5.06, N, 9.18; Found (%): C, 55.33, H, 4.78, N, 9.08; TLC: R$_f$=0.53 (SiO$_2$, CH$_2$Cl$_2$/MeOH=10/1); mp: 120–122° C.

EXAMPLE 60
N-(5-Acenaphthyl)-N'-((4-tert-butylphenyl)-(4-sec-butylphenyl)-N'-methylguanidine.HCl $^1$H NMR (CD$_3$OD): δ ppm 8.20–7.15 (m, ArH, 13H), 6.10 (d, CH, 1H), 3.43–3.41 (m, CH$_2$, 4H), 2.62 (m, CH, 1H), 1.59 (m, CH$_2$, 2H), 1.29 (s, CH$_3$, 9H), 1.21 (d, CH$_3$, J=7.0 Hz, 3H), 0.8 (t, CH$_3$, J=7.0 Hz, 3H); MS(EI): m/e 489.4 (M$^+$: C$_{34}$H$_{39}$N$_3$); Anal. (C$_{34}$H$_{39}$N$_3$.HCl): Calcd. (%): C, 77.61, H, 7.66, N. 7.99; Found (%): C, 77.43, H. 7.45, N. 7.97; TLC: R$_f$=0.5 (SiO$_2$, CH$_2$Cl$_2$/MeOH=10/1); mp: 173–174° C.

EXAMPLE 61
N-(4-Butoxyphenyl)-N,N'-bis(4-tert-butyl benzyl)guanidine.HCl $^1$H NMR (CD$_3$OD): δ ppm 7.50–6.60 (m, ArH, 12H), 4.90 (s, CH$_2$ 2H), 4.43 (s, CH$_2$, 2H), 3.97 (t, CH$_2$, J=6.4 Hz, 2H), 1.73 (m, CH$_2$, 2H), 1.49 (m, CH$_2$, 2H), 1.31 (s, CH$_3$, 18H), 0.94 (t, CH$_3$, J=7.4 Hz, 3H); MS(EI): m/e 499.3 (M$^+$: C$_{33}$H$_{45}$N$_3$O$_1$); Anal. (C$_{33}$H$_{45}$N$_3$O$_1$HCl): Calcd. (%): C, 73.92, H, 8.65, N, 7.84; Found (%): C, 73.87, H, 8.46, N, 7.91; TLC: R$_f$=0.4 (SiO$_2$, CH$_2$Cl$_2$/MeOH=10/1); mp: 112–113° C.

EXAMPLE 62
N-(3-sec-Butylphenyl)-N-(4-tert-butylbenzyl)guanidine.HCl $^1$H NMR (CD$_3$OD): δ ppm 7.38–6.81 (m, ArH, 8H), 4.86 (s, ArCH$_2$, 2H), 2.53 (m, CH, 1H), 1.45 (m, CH$_2$, 2H), 1.29 (s, CH$_3$, 9H), 1.12 (d, CH$_3$, J=6.93 Hz, 3H), 0.71 (t, CH$_3$, J=7.37 Hz, 3H); MS(EI): m/e 337.4 (M$^+$: C$_{22}$H$_{31}$N$_3$); Anal. (C, H, N; C$_{22}$H$_{31}$N$_3$.HCl·0.5H$_2$O): Calcd. (%): C, 68.79, H, 8.68, N, 10.97; Found (%): C, 69.23, H, 8.35, N, 10.92; TLC: R$_f$=0.46 (SiO$_2$, CH$_2$Cl$_2$/MeOH=10/1); mp: 190–191° C.

EXAMPLE 63
N-(3-tert-Butylphenyl)-N-(4-tert-butylbenzyl)guanidine.HCl $^1$H NMR (CDCl$_3$): δ ppm 7.51–7.19 (m, ArH, 8H), 4.92 (s, ArCH$_2$, 2H), 1.34 (s, CH$_3$, 9H), 1.31 (s, CH$_3$, 9H); MS(EI): m/e 337.4 (M$^+$: C$_{22}$H$_{31}$N$_3$); Anal. (C, H, N; C$_{22}$H$_{31}$N$_3$.HCl); Calcd. (%) C, 70.66, H, 8.62, N, 11.24; Found (%): C, 70.50, H, 8.55, N, 11.29; TLC: R$_f$=0.45 (SiO$_2$, CH$_2$Cl$_2$/MeOH=10/1); mp: 291–292° C.

EXAMPLE 64
N-(3-Pentoxyphenyl)-N-(4-tert-butylbenzyl)guanidine.HCl $^1$H NMR (CD$_3$OD): δ ppm 7.41–7.20 (m, ArH, 8H), 4.93 (s, ArCH$_2$, 2H), 3.90 (t, OCH$_2$, J=6.49 Hz, 2H), 1.78–1.60 (m, CH$_2$, 2H), 1.44–1.40 (m, 2CH$_2$, 4H), 1.31 (s, CH$_3$, 9H), 0.94 (t, CH$_3$, J=6.98 Hz, 3H); MS(EI): m/e 367.3 (M$^+$: C$_{23}$H$_{33}$N$_3$O); Anal. (C, H, N; C$_{23}$H$_{33}$N$_3$O.HCl·0.5H$_2$O); Calcd. (%): C, 66.89, H, 8.54, N, 10.17; Found (%): C, 66.98, H, 8.33, N, 10.05; TLC: R$_f$=0.51 (SiO$_2$, CH$_2$Cl$_2$/MeOH=10/1); mp: 198–199° C.

EXAMPLE 65
N-(5-Acenaphthyl)-N-(4-benzyloxybenzyl)guanidine.HCl ((5-C$_{12}$H$_9$)(4-(C$_6$H$_5$CH$_2$O)C$_6$H$_4$CH$_2$)NC(=NH)NH$_2$).HCl)

$^1$H NMR (CDCl$_3$): δ ppm 7.56–6.86 (m, ArH, 14H), 5.31 (d, CH$_2$, J=15.02 Hz, 1 H), 5.02 (s, CH$_2$, 2H), 4.70 (d, CH$_2$, J=15.41 Hz, 1 H), 3.50–3.41 (m, 2CH$_2$, 4H); MS(EI): m/e 407.3 (M$^+$: C$_{27}$H$_{25}$N$_3$O); Anal. (C, H, N; C$_{27}$H$_{25}$N$_3$O.HCl); Calcd. (%): C, 73.04, H, 5.90, N, 9.46; Found (%): C, 72.93, H, 5.68, N, 9.30; TLC: R$_f$=0.51 (SiO$_2$, CH$_2$Cl$_2$/MeOH=10/1); mp: 118–119° C.

EXAMPLE 66
N-(4-sec-Butylphenyl)-N-(4-benzyloxybenzyl)guanidine.HCl $^1$H NMR (CD$_3$OD): δ ppm 7.39–6.92 (m, ArH, 13H), 5.05 (s, OCH$_2$, 2H), 4.82 (s, CH$_2$, 2H), 2.62 (m, CH, 1H), 1.60 (m, CH$_2$, 2H), 1.21 (d, CH$_3$, J=6.96 Hz, 3H), 0.81 (t, CH$_3$, J=7.4 Hz, 3H); MS(EI): m/e 387.3 (M$^+$: C$_{25}$H$_{29}$N$_3$O); Anal. (C, H, N; C$_{25}$H$_{29}$N$_3$O.HCl·0.6H$_2$O); Calcd.(%): C, 69.06, H, 7.23, N, 9.66; Found (%): C, 68.86, H, 6.83, N, 9.80; TLC: R$_f$=0.48 (SO$_2$, CH$_2$Cl$_2$/MeOH=10/1); mp: 84–85° C.

EXAMPLE 67
N-(4-Benzyloxyphenyl)-N-(4-benzyloxybenzyl)guanidine.HCl $^1$H NMR (CD$_3$OD): δ ppm 7.40–6.93 (m, ArH, 18H), 5.08 (s, OCH$_2$, 2H), 5.06 (s, OCH$_2$, 2H), 4.79 (s, CH$_2$, 2H); MS(EI): m/e 437.2 (M$^+$: C$_{28}$H$_{27}$N$_3$O$_2$); Anal. (C, H, N; C$_{28}$H$_{27}$N$_3$O$_2$.HCl); Calcd.(%): C, 70.95, H, 5.95, N, 8.86; Found (%): C, 70.81, H, 5.71, N, 8.71; TLC: R$_f$=0.44 (SiO$_2$, CH$_2$Cl$_2$/MeOH=10/1); mp: 193–194° C.

EXAMPLE 68
N-(5-Acenaphthyl)-N-(3-benzyloxybenzyl)guanidine.HCl $^1$H NMR (CDCl$_3$): δ ppm 7.45–6.55 (m, ArH, 14H), 5.25–5.45 (m, CH$_2$, 1H), 4.86 (s, CH$_2$, 2H), 4.45–4.65 (d, CH$_2$, 1H), 3.25–3.50 (m, 2CH$_2$, 4H); MS(EI): m/e 407.4 (M$^+$: C$_{27}$H$_{25}$N$_3$O); Anal. (C, H, N; C$_{27}$H$_2$,N$_3$O.HCl.H$_2$O); Calcd. (%): C, 70.20, H, 6.11, N, 9.10; Found (%): C, 70.42, H, 6.00, N, 9.18; TLC: R$_f$=0.38 (SiO$_2$, CHCl$_3$/MeOH=10/1); mp: 140–141° C.

EXAMPLE 69
N-(4-isopropylphenyl)-N-(4-tert-butylbenzyl)guanidine.HCl $^1$H NMR (CD$_3$OD): δ ppm 7.12–7.41 (m, ArH, 8H), 4.88 (s, CH$_2$, 2H), 2.80–3.00 (m, CH, 1H), 1.30 (s, CMe$_3$, 9H), 1.23 (d, CH$_3$, J=6.9 Hz, 3H); MS(EI): m/e 324 (M$^+$: C$_{21}$H$_{29}$N$_3$); HRMS: 323.2366 (Calcd. 323.2361); Anal. (C, H, N; C$_{21}$H$_{29}$N$_3$.HCl); Calcd. (%): C, 70.08, H, 8.40, N, 11.67; Found (%): C, 69.85, H, 8.24, N, 11.90; TLC: $R_f$=0.64 (SiO$_2$, CHCl$_3$/MeOH=10/1); HPLC: 100%; mp: 260–261° C.

EXAMPLE 70
N-(4-Benzyloxyphenyl)-N-(4-tert-butylbenzyl) guanidine.HCl $^1$H NMR (CD$_3$OD): δ ppm 7.00–7.50 (m, ArH, 13H), 5.08 (s, OCH$_2$, 2H), 4.84 (s, CH$_2$, 2H), 1.30 (s, CMe$_3$, 9H); MS(EI): m/e 388 (M$^+$: C$_{25}$H$_{29}$N$_3$O); HRMS: 387.2315 (Calcd.: 387.2311); TLC: R$_f$=0.49 (SiO$_2$, CHCl$_3$/MeOH=10/1); HPLC: 99.8%; mp: 178–179° C.

EXAMPLE 71
N-(4-Hexylphenyl)-N-(4-hexylbenzyl)guanidine.mesylate $^1$H NMR (CD$_3$OD): δ ppm 7.05–7.30 (m, ArH, 8H), 4.86 (s, CH$_2$, 2H), 2.69 (s, CH$_3$SO$_3$H, 3H), 2.55–2.64 (m, 2CH$_2$, 4H), 1.50–1.70 (m, 2CH$_2$, 4H), 1.25–1.40 (m, 6CH$_2$, 12H), 0.80–1.00 (m, CH$_3$, 6H); MS(EI): m/e 493.4 (M$^+$: C$_{28}$H$_{39}$N$_3$); HRMS: 393.3166 (Calcd: 393.3160); TLC: R$_f$=0.52 (SiO$_2$, CHCl$_3$/MeOH=10/1); HPLC: 99.7%; mp: oil.

EXAMPLE 72
N-(4-sec-Butylphenyl)-N-(4-t-butylbenzyl)-N'-pyrrolidinylguanidine.HCl $^1$H NMR (CD$_3$OD): δ ppm 7.50–7.15 (m, ArH, 8H), 4.95 (s, CH$_2$, 2H), 3.25–3.15 (m, CH$_2$, 4H), 2.65–2.50 (m, CH, 1H), 1.80–1.90 (m, CH$_2$, 4H), 1.68–1.55 (m, CH$_2$, 2H), 1.31 (s, t-butyl, 9H), 1.23 (d, CH$_3$, J=7.0 Hz, 3H), 0.79 (t, CH$_3$, J=7.4 Hz, 3H); HRMS(EI): m/e 391.2991 (Calcd. 391.2987 for C$_{26}$H$_{37}$N$_3$); TLC: R$_f$=0.4 (SiO$_2$, CHCl$_3$/MeOH=10/1); HPLC: 96% pure; mp: 98–100° C.

EXAMPLE 73
N-(4-sec-Butylphenyl)-N-(4-t-butylbenzyl)-N'-(4-thiomorpholinyl)guanidine.HCl $^1$H NMR (CD$_3$OD): δ ppm 7.50–7.18 (m, ArH, 8H), 4.97 (s, CH$_2$, 2H), 3.15–3.05 (m, CH$_2$, 4H), 2.70–2.60 (m, CH, 1H), 2.40–2.25 (m, CH$_2$, 4H), 1.68–1.56 (m, CH$_2$, 2H), 1.31 (s, t-butyl, 9H), 1.23 (d, CH$_3$, J=7.0 Hz, 3H), 0.79 (t, CH$_3$, J=7.4 Hz, 3H); HRMS(EI): m/e 423.2722 (Calcd. 423.2708 for C$_{26}$H$_{37}$S$_1$N$_3$); Anal. (C$_{26}$H$_{37}$S$_1$N$_3$.HCl); Calcd (%): C, 67.87, H, 8.32, N, 9.13; Found (%): C, 67.85, H, 8.11, N, 9.36; TLC: R$_f$=0.4 (SiO$_2$, CHCl$_3$/MeOH=10/1); HPLC: 98.6% pure; mp: 70–72° C.

EXAMPLE 74
N-(4-sec-Butylphenyl)-N-(4-tert-butylbenzyl)-N'-piperidinylguanidine.HCl $^1$H NMR (CD$_3$OD): δ ppm 7.50–7.16 (m, ArH, 8H), 4.96 (s, CH$_2$, 2H), 2.62 (m, CH, 1H)m 1.70–1.40 (m, 6CH$_2$, 12H), 1.31 (s, CH$_3$, 9H), 1.22 (d, CH$_3$, J=6.93 Hz, 3H), 0.79 (t, CH$_3$, J=7.39 Hz, 3H); HRMS: 405.3138 (Calcd: 405.3144 for C$_{27}$H$_{39}$N$_3$); HPLC: 99.80%; TLC: R$_f$=0.47 (SiO$_2$, CH$_2$Cl$_2$/MeOH=10/1); mp: 217–218° C.

EXAMPLE 75
N-(4-sec-Butylphenyl)-N-(4-tert-butylbenzyl)-N'-(4-morpholinyl)guanidine.HCl $^1$H NMR (CD$_3$OD): δ ppm 7.21–7.46 (m, ArH, 8H), 4.99 (s, CH$_2$, 2H), 3.41–3.45 (m, 2OCH$_2$, 4H), 3.30–3.31 (m, NCH$_2$, 4H), 2.55–2.70 (m, CH, 1H), 1.59–1.62 (m, CH$_2$, 2H), 1.31 (s, CMe$_3$, 9H), 1.23 (d, CH$_3$, J=7.0 Hz, 3H), 0.79 (t, CH$_3$, J=7.4 Hz, 3H); MS(EI): m/e 408 (M$^+$: C$_{26}$H$_{37}$N$_3$O); Anal. (C, H, N; C$_{26}$H$_{37}$N$_3$O.HCl.0.75 H$_2$O); Calcd. (%): C, 68.24, H, 8.70, N, 9.18; Found (%): C, 67.76, H, 8.56, N, 9.08; TLC: R$_f$=0.43 (SiO$_2$, CHCl$_3$/MeOH=10/1); HPLC: 98.57%; mp: 220–221° C.

EXAMPLE 76
N-(4-sec-Butylphenyl)-N-4-tert-butylbenzyl)-N'-(4-propylpiperidinyl)guanidine.HCl $^1$H NMR (CD$_3$OD): δ ppm 7.16–7.46 (m, ArH, 8H), 4.94 (s, CH$_2$, 2H), 3.70–3.90 (m, ring-H, 2H), 2.80–2.95 (m, ring-H, 3H), 2.55–2.70 (m, CH, 1H), 0.59–2.70 (m, ring-4H; CMe$_3$l 9H; 3CH$_3$, 9H; 3CH$_2$, 6H); MS(EI): m/e 448 (M$^+$: C$_{30}$H$_{45}$N$_3$); Anal. (C, H, N; C$_{30}$H$_{45}$N$_3$.HCl.1.25H$_2$O); Calcd. (%): C, 71.11, H, 9.65, N, 8.29; Found (%): C, 71.13, H, 9.50, N, 8.53; TLC: R$_f$=0.64 (SiO$_2$, CHCl$_3$/MeOH=10/1); HPLC: 93.1%; mp: 109–110° C.

EXAMPLE 77
N-(4-Butoxyphenyl)-N-(4-tert-butylbenzyl)-N'-(4-piperidinyl)guanidine.HCl $^1$H NMR (CD$_3$OD): δ ppm 6.94–7.45 (m, ArH, 8H), 4.91 (s, CH$_2$, 2H), 3.97 (t, OCH$_2$, J=6.36 Hz, 2H), 1.70–1.85 (m, CH$_2$, 2H), 1.25–1.60 (m, ring-H, 10H; CMe$_3$, 9H; CH$_2$, 2H), 0.98 (t, CH$_3$, J=7.4 Hz, 3H); MS(EI): m/e 422.3 (M$^+$: C$_{27}$H$_{39}$N$_3$O); HRMS: 421.3110 (Calcd.: 421.3093); TLC: R$_f$=0.28 (SiO$_2$, CHCl$_3$MeOH=10/1); HPLC: 93.7%; mp: 99–100° C.

EXAMPLE 78
N-(4-sec-Butylphenyl)-N-(4-tert-butylbenzyl)-N'-(4-benzylpiperidinyl)guanidine.mesylate $^1$H NMR (CD$_3$OD): δ ppm 7.03–7.46 (m, ArH, 13H), 4.94 (s, CH$_2$, 2H), 3.70–3.90 (m, ring-H, 3H), 2.77–2.95 (m, ring-H, 3H), 2.70 (s, CH$_3$SO$_3$H, 3H), 2.60–2.70 (m, CH, 1H), 2.40 (d, CH$_2$, J=7.15 Hz, 2H), 1.55–1.75 (m, CH$_2$, 2H), 1.40–1.55 (m, ring-H, 3H), 1.31 (m, CMe$_3$, 9H), 1.24 (d, CH$_3$, J=6.93 Hz, 3H), 0.82 (t, CH$_3$, J=7.4 Hz, 3H); MS(EI): m/e 495.3 (M$^+$: C$_{34}$H$_{45}$N$_3$); HRMS: 495.3604 (Calcd.: 495.3613); TLC: R$_f$=0.55 (SiO$_2$, CHCl$_3$MeOH=10/1); HPLC: 94.7%; mp: 85–86° C.

EXAMPLE 79
N-(4-Benzyloxyphenyl)-N-(4-tert-butylbenzyl)-N'-(4-morpholinyl)guanidine.HCl $^1$H NMR (CD$_3$OD): δ ppm 7.00–7.50 (m, ArH, 13H), 5.10 (s, OCH$_2$, 2H), 4.94 (s, CH$_2$, 2H), 3.41–3.50 (m, 2OCH$_2$, 4H), 3.25–3.35 (m, NCH$_2$, 4H), 1.31 (s, CMe$_3$, 9H); MS(EI): m/e 457.4 (M$^+$: C$_{29}$H$_{35}$N$_3$O$_2$): Anal. (C, H, N; C$_{29}$H$_{35}$N$_3$O$_2$.HCl); Calcd. (%): C, 70.50, H, 7.34, N, 8.50; Found (%): C, 70.29, H, 7.15, N, 8.36; TLC: R$_f$=0.50 (SiO$_2$, CHCl$_3$/MeOH=10/1); HPLC: 95%; mp: 75–77° C.

EXAMPLE 80
N-(4-sec-Butylphenyl)-N-(4-tert-butylbenzyl)-N'-(1,2,3,4-tetrahydroisoquinolinyl)guanidine.HCl $^1$H NMR (CD$_3$OD): δ ppm 6.95–7.50 (m, ArH, 12H), 5.01 (s, benzylic-CH$_2$, 2H), 4.46 (s, benzylic-CH$_2$N, 2H), 3.60 (t, CH$_2$, J=6 Hz, 2H), 2.55–2.70 (m, CH, 1H), 2.48 (t, CH$_2$, J=6.0 Hz, 2H), 1.50–1.65 (m, CH$_2$, 2H), 1.30 (s, CMe$_3$, 9H), 1.20 (d, CH$_3$, J=6.93 Hz, 3H), 0.77 (t, CH$_3$, J=7.4 Hz, 3H); MS(EI): m/e 454.4 (M$^+$: C$_{31}$H$_{39}$N$_3$); HRMS: 453.3165 (Calcd.: 453.3144); TLC: R$_f$=0.51 (SiO$_2$, CHCl$_3$MeOH=10/1); HPLC: 100%; mp: 217–218° C.

EXAMPLE 81
N-(3-Butoxy-4-methoxyphenyl)-N-(4-tert-butylbenzyl)-N'-(4-morpholinyl)guanidine.HCl $^1$H NMR (CD$_3$OD): δ ppm 6.55–7.50 (m, ArH, 7H), 4.93 (s, CH$_2$, 2H), 3.80–3.90 (m, OCH$_2$+OCH$_3$, 5H), 3.45–3.55 (m, 2OCH$_2$, 4H), 3.30–3.40 (m, NCH$_2$, 4H), 1.65–1.80 (m, CH$_2$, 2H), 1.40–1.55 (m, CH$_2$, 2H), 1.31 (s, CMe$_3$l 9H), 0.97 (t, CH$_3$, J=7.4 Hz, 3H); MS(EI): m/e 453.4 (M$^+$: C$_{27}$H$_{39}$N$_3$O$_3$); HRMS: 453.3010 (Calcd.: 453.2991); TLC: R$_f$=0.39 (SiO$_2$, CHCl$_3$/MeOH=10/1); HPLC: 98%; mp: 197–199° C.

EXAMPLE 82
N-(4-sec-Butylphenyl)-N-(4-tert-butylbenzyl)-N'-(3,5-dimethyl-4-morpholinyl)guanidine.HCl $^1$H NMR (CD$_3$OD): δ ppm 7.20–7.50 (m, ArH, 8H), 4.99 (s, CH$_2$, 2H), 3.55–3.70 (m, 2OCH, 2H), 3.15–3.25 (m, NCH$_2$, 2H), 2.50–2.70 (m, CH+NCH$_2$, 3H), 1.55–1.70 (m, CH$_2$, 2H), 1.30 (s, CMe$_3$, 9H), 1.23 (d, CH$_3$, J=6.93 Hz, 3H), 0.99 (m, 2CH$_3$, 6H), 0.79 (m, CH$_3$, 3H); MS(EI): m/e 435.5 (M$^+$: C$_{28}$H$_{41}$N$_3$O); TLC: R$_f$=0.51 (SiO$_2$, CHCl$_3$MeOH=10/1); HPLC: 98.7%; mp: 98–99° C.

EXAMPLE 83
N-(4-tert-Butylphenyl)-N-(4-tert-butylbenzyl)-N'-(4-sec-butylphenyl)-N'-(methyl)guanidine.HCl $^1$H NMR (CDCl$_3$): δ ppm 7.42–6.60 (m, ArH, 12H), 4.92 (s, CH$_2$, 2H), 3.56 (s, CH$_3$, 3H), 2.52 (m, CH, 1H), 1.54 (m, CH$_2$, 2H), 1.33 (s, CH$_3$, 9H), 1.26 (s, CH$_3$, 9H), 1.17 (d, CH$_3$, J=7.14 Hz, 3H), 0.80 (t, CH$_3$, J=7.28 Hz, 3H); MS(EI): m/e 483.5 (M$^+$: C$_{33}$H$_{45}$N$_3$); Anal. (C, H, N: C$_3$H$_{45}$N$_3$.HCl); Calcd. (%): C, 76.19, H, 8.91, N, 8.08; Found (%): C, 76.12, H, 8.87, N, 8.03; TLC: R$_f$=0.53 (SiO$_2$, CH$_2$Cl$_2$/MeOH=10/1); mp: 111–112° C.

EXAMPLE 84
N-(4-sec-Butylphenyl)-N-(4-tert-butylbenzyl)-N'-(4-sec-butylphenyl)-N'-(methyl)guanidine.HCl $^1$H NMR (CD$_3$OD): δ ppm 7.50–6.70 (m, ArH, 12H), 4.88 (s, CH$_2$, 2H), 3.35 (s, CH$_3$, 3H), 2.50 (m, 2CH, 2H), 1.54 (m, 2CH$_2$, 4H), 1.30 (s, CH$_3$, 9H), 1.15 (m, 2CH$_3$, 6H), 0.80 (m, 2CH$_3$, 6H); MS(EI): m/e 483.5 (M$^+$: C$_{33}$H$_{45}$N$_3$); Anal. (C, H, N; C$_{33}$H$_{45}$N$_3$.HCl); Calcd. (%): C, 76.19, H, 8.91, N, 8.08; Found (%): C, 75.94, H, 9.07, N, 7.86; TLC: R$_f$=0.30 (SiO$_2$, CH$_2$Cl$_2$/MeOH=10/1); mp: 106–107° C.

EXAMPLE 85
N-(4-sec-Butylphenyl)-N-(4-tert-butylbenzyl)-N'-(phenyl)guanidine.HCl $^1$H NMR (CD$_3$OD): δ ppm 7.50–7.23 (m, ArH, 13H), 5.03 (s, CH$_2$, 2H), 2.62 (m, CH, 1H), 1.60 (m, CH$_2$, 2H), 1.30 (s, CH$_3$, 9H), 1.15 (d, CH$_3$, J=6.96 Hz, 3H), 0.80 (t, CH$_3$, J=7.37 Hz, 3H); HRMS: 413.2818 (Calcd: 413.2831 for C$_{28}$H$_{35}$N$_3$); HPLC: 96.80%; TLC: R$_f$=0.58 (SiO$_2$, CH$_2$Cl$_2$/MeOH=10/1); mp: 204–205° C.

EXAMPLE 86
N-(4-sec-Butylphenyl)-N-(4-tert-butylbenzyl)-N'-(4-chlorophenyl)guanidine.HCl $^1$H NMR (CD$_3$OD): δ ppm 7.22–7.46 (m, ArH, 12H), 5.02 (s, CH$_2$, 2H), 2.55–2.70 (M, CH, 1H), 1.59–1.62 (m, CH$_2$, 2H), 1.30 (s, CMe$_3$ 9H), 1.20 (d, CH$_3$, J=6.9 Hz, 3H), 0.80 (t, CH$_3$, J=7.4 Hz, 3H); MS(EI): m/e 447.7 (M$^+$: C$_{28}$H$_{34}$N$_3$ClC); HRMS: 447.2412 (Calcd. 447.2441); Anal. (C, H, N; $_{28}$H$_{34}$N$_3$Cl.HCl.0.5H$_2$O); Calcd. (%): C, 68.15, H, 7.35, N, 8.51; Found (%): C, 68.15, H, 7.44, N, 8.50; TLC: R$_f$=0.40 (SiO$_2$, CHCl$_3$/MeOH=10/1); mp: 98–99° C.

EXAMPLE 87
N-(4-Butoxyphenyl)-N-(4-tert-butylbenzyl)-N'-(phenyl)guanidine.HCl $^1$H NMR (CD$_3$OD): δ ppm 6.94–7.47 (m, ArH, 13H), 4.99 (s, CH$_2$, 2H), 3.97 (t, OCH$_2$, J=6.43 Hz, 2H), 2.55–2.70 (m, CH, 1H), 1.65–1.80 (m, CH$_2$, 2H), 1.40–1.55 (m, CH$_2$, 2H), 1.31 (s, CMe$_3$, 9H), 0.96 (t, CH$_3$, J=7.4 Hz, 3H); MS(EI): m/e 430 (M$^+$: C$_{28}$H$_{35}$N$_3$O); Anal. (C, H, N; C$_{28}$H$_{35}$N$_3$O.HCl.0.75H$_2$O); Calcd. (%): C, 70.13, H, 7.88, N, 8.76; Found (%): C, 70.29, H, 7.53, N, 9.12; TLC: R$_f$=0.26 (SiO$_2$, CHCl$_3$/MeOH=10/1); HPLC: 97.1%; mp: 95–96° C.

EXAMPLE 88
N-(4-sec-Butylphenyl)-N-(4-tert-butylbenzyl)-N'-(phenyl)-N'-methylguanidine.HCl $^1$H NMR (CD$_3$OD): δ ppm 6.79–7.44 (m, ArH, 13H), 4.88 (s, CH$_2$, 2H), 3.35 (s, CH$_3$, 3H), 2.45–2.60 (m, CH, 1H), 1.45–1.62 (m, CH$_2$, 2H), 1.30 (s, CMe$_3$, 9H), 1.15 (d, CH$_3$, J=6.9 Hz, 3H), 0.77 (t, CH$_3$, J=7.4 Hz, 3H); MS(EI): m/e 427.1 (M$^+$: C$_{29}$H$_{37}$N$_3$); HRMS: 427.2987 (Calcd.: 427.2954); Anal. (C, H, N; C$_{29}$H$_{37}$N$_3$.HCl); Calcd. (%): C, 75.05, H, 8.25, N, 9.05; Found (%): C, 74.91, H, 8.12, N, 9.11; TLC: R$_f$=0.56 (SiO$_2$, CHCl$_3$/MeOH=10/1); mp: 80–82° C.

EXAMPLE 89
N-(4-sec-Butylphenyl)-N-(4-tert-butylbenzyl)-N'-(3,4-dichlorophenyl)guanidine.HCl $^1$H NMR (CD$_3$OD): δ ppm 7.21–7.57 (m, ArH, 11H), 5.04 (s, CH$_2$, 2H), 2.55–2.70 (m, CH, 1H), 1.50–1.65 (m, CH$_2$, 2H), 1.30 (s, CMe$_3$, 9H), 1.20 (d, CH$_3$, J=6.9 Hz, 3H), 0.79 (t, CH$_3$, J=7.4 Hz, 3H); MS(EI): m/e 482.1 (M$^+$: C$_{28}$H$_{33}$N$_3$Cl$_2$); HRMS: 481.2025 (Calcd.: 481.2052); Anal. (C, H, N; C$_{28}$H$_{33}$N$_3$Cl$_2$.HCl); Calcd. (%): C, 64.80, H, 6.60, N, 8.10; Found (%): C, 64.78, H, 6.58, N, 8.14; TLC: R$_f$=0.71 (SiO$_2$, CHCl$_3$/MeOH=10/1); mp: 168–169° C.

EXAMPLE 90
N-(4-Hexylphenyl)-N-(4-tert-hexylbenzyl)-N'-phenylguanidine.HCl $^1$H NMR (CD$_3$OD): δ ppm 7.15–7.70 (m, ArH, 13H), 5.01 (s, CH$_2$, 2H), 2.55–2.70 (m, 2CH$_2$, 4H), 1.50–1.70 (m, 2CH$_2$, 4H), 1.25–1.40 (m, 6CH$_2$, 12H), 0.80–1.00 (m, CH$_3$, 6H); MS(EI): m/e 469.4 (M$^+$: C$_{32}$H$_4$N$_3$); HRMS: 469.3476 (Calcd.: 469.3457); TLC: R$_f$=0.56 (SiO$_2$, CHCl$_3$/MeOH= 10/1); HPLC: 100%; mp: oil.

EXAMPLE 91
N-(4-sec-Butylphenyl)-N-(4-tert-butylbenzyl)-N'-(4-benzyloxyphenyl)guanidine.mesylate $^1$H NMR (CD$_3$OD): δ ppm 7.05–7.50 (m, ArH, 17H), 5.1 1 (s, OCH$_2$, 2H), 5.00 (s, CH$_2$, 2H), 2.69 (s, CH$_3$SO$_3$H, 3H), 2.55–2.70 (m, CH, 1H), 1.50–1.70 (m, CH$_2$, 2H), 1.30 (s, CMe$_3$, 9H), 1.20 (d, CH$_3$, J=6.9 Hz, 3H), 0.80 (t, CH$_3$, J=7.4 Hz, 3H); MS(EI): m/e 519.5 (M$^+$: C$_{35}$H$_{41}$N$_3$O); Anal. (C, H, N; C$_{35}$H$_{41}$N$_3$O.CH$_3$SO$_3$H); Calcd. (%): C, 70.21, H, 7.37, N, 6.82; Found (%): C, 70.12, H, 7.16, N, 6.69; TLC: R$_f$=0.53 (SiO$_2$, CHCl$_3$/MeOH 10/1); HPLC: 96.9%; mp: 142–143° C.

EXAMPLE 92
N,N'-Bis-(4-tert-butylphenyl)-N,N'-dimethylguanidine.HBr

White solid; mp: 175–177° C.; TLC (CH$_2$Cl$_2$:MeOH; 10:1); R$_f$=0.39; $^1$H NMR (CD$_3$OD): 7.21–7.18 (d, J=8.52 Hz, 4H, ArH), 6.80–6.78 (d, J=8.51 Hz, 4H, ArH), 3.35 (s, 6H, —CH$_3$), 1.26 (s, 18H, —C(CH$_3$)$_3$); Anal. Calcd. for C$_2$H$_{33}$N$_3$.HCl (388.00); C, 71.20, H, 8.83, N, 10.83; Found: C, 70.88, H, 8.61, N, 10.75.

EXAMPLE 93
N-(4-Benzyloxyphenyl)-N'-(4-tert-butylphenyl)guanidine.HCl

White solid; mp: 143–144° C.; TLC (CH$_2$Cl$_2$:MeOH; 15:1); R$_f$=0.35; $^1$H NMR (CD$_3$OD): 7.547–7.089 (m, 13H, ArH), 5.135 (s, CH$_2$, 2H), 1.346 (s, t-butyl, 9H); Anal. Calcd. for C$_{24}$H$_{28}$N$_3$ClO (409.96): C, 70.32, H, 6.88, N, 10.25; Found: C, 70.49, H, 6.94, N, 10.09.

EXAMPLE 94
N,N'-Bis-(3-(1'-methyl-2'-phenyl)ethyl)guanidine.HCl

White solid; mp: 93–95° C.; TLC (CH$_2$Cl$_2$:MeOH; 15:1); R$_f$=0.41; $^1$H NMR (CD$_3$OD): 7.395–7.344 (t, J=8.69 Hz, 2H, ArH), 7.225–7.077 (m, 16H, ArH), 3.092–3.045 (m, CH, 2H), 2.952–2.827 (m, CH$_2$, 4H), 1.273–1.250 (d, J=6.87 Hz, 6H); Anal. Calcd. for C$_{31}$H$_{34}$N$_3$Br.1/2H$_2$O (537.55): C, 69.27, H, 6.51, N, 7.81; Found: C, 69.61H, 6.63, N, 7.87.

EXAMPLE 95
N-Methyl-N4-benzyloxyphenyl-N'-(4-tert-butylphenyl)guanidine.mesylate White solid; mp: 230–232° C.; TLC (AcOEt:MeOH; 10:1): R$_f$=0.45; $^1$H NMR: 7.421–6.961 (m, ArH, 13H), 5.059 (s, OCH$_2$, 2H), 3.413 (s, N—CH$_3$, 3H), 2.770 (s, CH$_3$, 3H), 1.286 (s, t-butyl, 9H); Anal. Calcd. for C$_{25}$H$_{33}$N$_3$O$_3$S.1/2H$_2$O (492.63: C, 63.33, H, 6.90, N, 8.53; Found: C, 63.48, H, 6.40, N, 8.48.

EXAMPLE 96
N,N'-Bis-(4-Hexylphenyl)guanidine.mesylate

White solid; mp: 92–94° C.; TLC (AcOEt:MeOH; 10:1): R$_f$=0.49; $^1$H NMR: 7.265–7.172 (m, ArH, 8H), 2.823 (s, CH$_3$, 3H), 2.627–2.575 (t, CH$_2$, J=7.695 Hz, 4H), 1.583–1.558 (m, CH$_2$, 4H), 1.336–1.261 (m, CH$_2$CH$_2$, 8H), 0.905–0.861 (t, CH$_3$, J=6.59 Hz, 6H); Anal. Calcd. for C$_{26}$HH$_{41}$N$_3$O$_3$S (475.69): C, 65.65, H, 8.69, N, 8.83; Found: C, 65.17, H, 8.63, N, 8.70.

EXAMPLE 97
N-(3-1-(4'-Ethoxy)benzyl)phenethyl)-N'-(4-tert-butylphenyl)guanidine.mesylate (3-(4-(CH$_3$CH$_2$O)C$_8$H$_4$CH$_2$)C$_6$H$_4$)(CH$_3$)CHNHC(=NH)NH(4-(CH$_3$)$_3$C)C$_6$H$_4$ mesylate)

White solid; mp: 83–85° C.; TLC (AcOEt:MeOH; 10:1): R$_f$=0.49; $^1$H NMR: 7.465–6.680 (m, ArH, 12H), 3.957–3.888 (m, CH$_2$, 2H), 2.961 (m, CH, 1H), 2.836 (s, CH$_3$, 2H), 2.825–2.727 (m, CH$_2$, 2H), 1.322 (s, tert-butyl, 9H), 1.361–1.268 (m, CH$_2$, CH$_3$, 5H); HRMS: 429.2749 (429.2780 Calcd. for C$_{28}$H$_{35}$ON$_3$).

EXAMPLE 98
N-(4-Benzyloxyphenyl)-N'-methyl-N'-(4-tert-butylphenyl)guanidine.mesylate White solid; mp: 100–101° C.; TLC (AcOEt:MeOH; 10:1): R$_f$=0.46; $^1$H NMR: 7.457–7.371 (m, ArH, 7H), 7.199–7.170 (d, ArH, J=8.58 Hz, 2H), 7.081–7.052 (d, ArH, J=8.85 Hz, 2H), 6.924–6.894 (d, ArH, J=9.01 Hz, 2H), 5.034 (s, CH$_2$, 2H), 3.456 (s, CH$_3$, 3H), 3.456 (s, CH$_3$, 3H), 1.323 (s, tert-butyl, 9H); HRMS: 387.2292 (387.2311 Calcd. for C$_{25}$H$_{29}$ON$_3$).

EXAMPLE 99
N-(3-(4-tert-Butylbenzyloxy)phenyl)-N'-(4-tert-butylphenyl)guanidine.mesylate White solid; mp: 88–92° C.; TLC (AcOEt:MeOH; 10:1): R$_f$=0.48; $^1$H NMR (CDCl$_3$): 7.479–7.199 (m, ArH, 10H), 6.909–6.878 (d, ArH, J=8.94 Hz, 2H), 5.071 (s, CH$_2$, 2H), 2.856 (s, —CH$_3$, integration is 1.5H instead of 3H), 1.329 (s, t-butyl, 9H), 1.292 (s, t-butyl, 9H); HRMS: 429.2783 (429.2780 Calcd. for C$_{30}$H$_{31}$N$_3$).

EXAMPLE 100
N-(3-(1'-Benzylbutyl)phenyl)-N'-(4-tert-butylphenyl)guanidine.mesylate White solid; mp: 70–73° C.; TLC (AcOEt:MeOH; 10:1): R$_f$=0.78; $^1$H NMR (CDCl$_3$): 7.494–6.759 (m, ArH, 17H), 3.014–2.691 (m, —CH$_2$, —CH, —CH$_3$, 6H), 1.755–1.168 (m, CH$_2$CH$_2$, 4H), 1.331 (s, t-butyl, 9H), 0.896–0.847 (t, CH$_3$, J=7.28 Hz, 3H); HRMS: 413.2840 (413.2831 Calcd. for C$_{28}$H$_{35}$N$_3$).

EXAMPLE 101
N,N'-Bis-(4-butylphenyl)-N-methylguanidine.HCl

White solid; mp: 137–138° C.; TLC (CHCl$_3$:MeOH; 10:1): R$_f$=0.40; $^1$H NMR (CDCl$_3$): 7.234–7.026 (m, ArH, 8H), 3.618 (s, CH$_3$, 3H), 2.628–2.535 (m, CH$_2$, 4H), 1.600–1.493 (m, CH$_2$, 4H), 1.382–1.280 (m, CH$_2$, 4H), 0.963–0.900 (m, CH$_3$, 6H); Anal. Calcd. for C$_{22}$H$_{32}$N$_3$Cl: C, 70.66, H, 8.62, N, 11.24; Found: C, 70.47, H, 8.04, N, 11.31.

EXAMPLE 102
N,N'-Bis-(4-tert-butylphenyl)-N,N'-dimethylguanidine.HCl

White solid; mp: 134° C.; TLC (CHCl$_3$:MeOH; 10:1): R$_f$=0.33; $^1$H NMR (CDCl$_3$): 9.460 (s, 2H), 6.923–6.895 (d, ArH, J=6.37 Hz, 4H), 6.668–6.640 (d, ArH, J=8.45 Hz, 4H), 3.557 (s, —CH$_3$, 3H), 2.529–2.479 (t, CH$_2$, J-7.525 Hz), 1.570–1.470 (m, CH$_2$, 4H), 1.358–1.283 (m, CH$_2$, 4H), 0.972–0.924 (t, CH$_3$, J=7.265 Hz, 6H); Anal. Calcd. for C$_{23}$H$_{34}$N$_3$Cl.1/2H$_2$O: C, 69.52, H, 8.82, N, 10.58; Found: C, 69.38, H, 8.52, N, 10.56.

EXAMPLE 103
N-(3-Naphthylmethyleneoxyphenyl)-N'-(4-tert-butylphenyl)guanidine.mesylate (3-(C$_{10}$H$_7$CH$_2$O)C$_6$H$_4$NHC(=NH)NH(4-(CH$_3$)$_3$C)C$_6$H$_5$ mesylate)

White solid; mp: 138–146° C.; TLC (CHCl$_3$:MeOH; 10:1): R$_f$=0.52; $^1$H NMR (CDCl$_3$): 7.861–7.803 (m, ArH, 4H), 7.516–7.113 (m, ArH, 8H), 6.936–6.881 (m, ArH, 3H), 5.222 (s, CH$_2$, 2H), 2.814 (s, CH$_3$, 3H), 1.291 (s, t-butyl, 9H); Anal. Calcd. for C$_{29}$H$_{33}$N$_3$O$_4$S: C, 67.03, H, 6.40, N, 8.09; Found: C, 67.26, H, 6.64, N, 8.29.

EXAMPLE 104
N-(4-Benzyloxyphenyl)-N'-(4-butylphenyl)guanidine.HCl

White solid; mp: 112° C.; TLC (CHCl$_3$:MeOH; 10:1): R$_f$=0.50; $^1$H NMR (CDCl$_3$): 7.403–7.206 (m, ArH, 11H), 7.009–7.039 (d, J=8.91 Hz, ArH, 2H), 5.068 (s, Ar—CH$_2$, 2H), 2.638–2.587 (t, J=7.42 Hz, CH$_2$, 2H), 1.576–1.560 (m, CH$_2$, 2H), 1.371–1.321 (m, CH$_2$, 2H), 0.938–0.890 (t, CH$_3$, J=7.36 Hz, 3H); Anal. Calcd. for C$_{24}$H$_{28}$ClN$_3$O: C, 70.32, H, 6.88, N, 10.25; Found: C, 70.42, H, 7.00, N, 10.07.

EXAMPLE 105
N,N'-Bis-(4-butylphenyl)-N-butylguanidine.HCl

White solid; mp: 118–119° C.; TLC (CHCl$_3$:MeOH; 10:1): R$_f$=0.43; $^1$H NMR: 7.235, 7.207, 7.033, 7.005 (q, ArH, 4H), 7.127–7.095 (d, J=9.63 Hz, ArH, 4H); Anal. Calcd. for C$_{27}$H$_{39}$N$_3$O$_4$ (469.62): C, 69.05, H, 8.37, N, 8.95; Found: C, 69.25, H, 8.38, N, 9.03.

EXAMPLE 106
N-3-(Benzyloxymethyl)phenyl-N'-(4-tert-butylphenyl)guanidine.mesylate White solid; mp: 66–68° C.; TLC (CHCl$_3$:MeOH; 10:1): R$_f$=0.56; $^1$H NMR (CDCl$_3$): 7.456–7.170 (m, ArH, 13H), 4.580 (s, CH$_2$, 2H), 4.529 (s, CH$_2$, 2H), 2.821 (s, CH$_3$, 3H), 1.303 (s, C(CH$_3$)$_3$, 9H); HRMS: 387.2299 (387.2229 calculated for C$_2$H$_{29}$N$_2$O$_2$).

EXAMPLE 107
N-(3,4-Bis-butyloxyphenyl)-N'-(4-tert-butylphenyl)guanidine.oxalate White solid; mp: 100–101° C.; TLC (CHCl$_3$:MeOH; 10:1): R$_f$=0.58; $^1$H NMR (CD$_3$OD): 7.5251–7.5027 (m, ArH, 2H), 7.2692–7.2402 (m, ArH, 2H), 7.0079–6.8720 (m, ArH, 3H), 4.0306–3.9880 (t, OCH$_2$, 4H), 1.7990–1.7404 (m, CH$_2$, 4H), 1.5580–1.5296 (m, CH$_2$, 4H), 1.3275 (s, C(CH$_3$)$_3$, 9H), 1.0243–1.9558 (t, CH$_3$, 6H); HRMS: 411.2886 (411.2886 calculated for C$_{25}$H$_{37}$N$_3$O$_2$).

EXAMPLE 108
N-(3-Benzyloxy)phenyl-N'-(4-tert-butylphenyl) guanidine.mesylate

White solid; mp: 140° C.; TLC (CHCl$_3$:MeOH; 10:1): R$_f$=0.50; $^1$H NMR (CDCl$_3$): 7.483–7.203 (m, 9H, ArH), 6.920–6.910 (m, 4H, ArH), 5.080 (s, CH$_2$, 2H), 2.849 (s, CH$_3$, 3H), 1.585–1.511 (m, NHs), 1.320 (s, —C(CH$_3$)$_3$, 9H); HRMS: 373.2158 (373.2154 calculated for C$_{24}$H$_{27}$N$_3$O).

EXAMPLE 109
N,N'-Bis-((3-butoxy-4-methoxy)phenyl)guanidine.HBr

White solid; mp: 174° C.; TLC (CHCl$_3$:MeOH; 10:1): R=0.43; $^1$H NMR (CDCl$_3$): 6.924–6.852 (m, 6H, ArH), 4.028–3.984 (t, CH$_2$, J=6.59 Hz, 4H), 3.892 (s, CH$_3$, 6H), 1.872–1.798 (m, CH$_2$, 4H), 1.594–1.472 (m, —CH$_2$, 4H), 1.021–0.972 (t, CH$_3$, J=7.28 Hz, 6H); HRMS: 415.2470 (415.2471 calculated for C$_{23}$H$_{33}$N$_3$O$_4$).

EXAMPLE 110
N-(4-Benzyloxyphenyl)-N-methyl-N'-(4-butylphenyl) guanidine.mesylate White solid; mp: 178.4–178.8° C.; TLC (CHCl$_3$:MeOH; 10:1): R$_f$=0.34; $^1$H NMR (CDCl$_3$): 7.390–6.919 (m, ArH, 13H), 5.029 (s, Ar—CH$_2$, 2H), 3.389 (s, CH$_3$, 3H), 2.717 (s, CH$_3$, 3H), 2.552–2.501 (t, J=7.48 Hz, CH$_2$, 2H), 1.544–1.493 (m, CH$_2$, 2H), 1.328–1.254 (m, CH$_2$, 2H), 0.916–0.867 (t, CH$_3$, J=7.33 Hz, 3H); HRMS: 387.2311 (387.2285 calculated for C$_{25}$H$_{29}$N$_3$O).

EXAMPLE 111
N,N'-Bis-(6-tetralinyl)guanidine.HBr

White solid; mp: too fluffy to measure; TLC (CHCl$_3$:MeOH; 10:1): R$_f$=0.50; $^1$H NMR (CDCl$_3$): 7.273–7.002 (m, ArH, 6H), 2.765 (s, 2CH$_2$, 4H), 1.824–1.780 (p, 2CH$_2$, 4H); Anal. Calcd. for C$_{21}$H$_{26}$N$_3$Br (400.36): C, 63.00, H, 6.55, N, 10.50; Found: C, 62.85, H, 6.62, N, 10.53.

EXAMPLE 112
N-(6-Tetralinyl)-N'-(4-tert-butylphenylguanidine.mesylate

Colorless crystal; mp: 53–55° C.; TLC (CHCl$_3$:MeOH; 10:1): R$_f$=0.45; $^1$H NMR (CDCl$_3$): 7.240–6.967 (m, 7H, ArH), 2.798 (s, CH$_3$, 3H), 2.736 (s, CH$_2$, 4H), 2.628–2.577 (t, J=7.47 Hz, CH$_2$, 2H), 1.790–1.770 (t, 2CH$_2$, 4H), 1.597–1.546 (m, CH$_2$, 2H), 1.374–1.300 (m, CH$_2$, 2H), 0.949–0.901 (t, CH$_3$, J=7.30 Hz, 3H); HRMS: 321.2184 (321.2205 calculated for C$_{21}$H$_{27}$N$_3$).

EXAMPLE 113
N-(5-Acenaphthyl)-N'-(6-benzothiozolyl)guanidine.HCl

Light green solid; mp: ° C.; TLC (CH$_2$Cl$_2$:MeOH; 15:1): R$_f$=0.25; $^1$H NMR (CD$_3$OD): 7.639–7.289 (m, ArH, 9H), 3.443–3.403 (m, CH$_2$CH$_2$, 4H), 2.086–1.756 (m, CH's, 13H); Anal. Calcd for C$_{29}$H$_{32}$N$_3$Cl (458.08): C, 76.04, H, 7.04, N, 9.17; Found: C, 75.97, H, 6.88, N, 9.06.

EXAMPLE 114
N-(5-Acenaphthyl)-N'-(6-N-benzylindolinyl) guanidine.mesylate

White solid; mp: 115–125° C.; TLC (AcOEt:MeOH; 10:1): R$_f$=0.27; $^1$H NMR: 7.709–7.260 (m, ArH, 13H), 3.469–3.377 (s, CH$_2$CH$_2$, 4H), 2.842 (s, CH$_3$, 3H); Anal. Calcd. for C$_{29}$H$_{30}$N$_4$O$_3$S (514.64): C, 67.68, H, 5.88, N, 10.89; Found: C, 67.51, H, 5.58, N. 10.88.

EXAMPLE 115
N-(5-Acenaphthyl)-N'-(4-benzo-2,1,3-thiadizaole) guanidine.HCl $^1$H NMR (CD$_3$OD): δ ppm 7.33–8.05 (m, ArH, 8H), 3.43–3.50 (m, 4H, CH$_2$); MS(EI): m/e 345.1 (M$^+$: C$_{19}$H$_{15}$N$_5$S); Anal. (C, H, N; C$_{19}$H$_{15}$N$_5$S.HCl.1/2 H$_2$O): Calcd. (%): C, 58.45, H, 4.39, N, 17.95; Found (%): C, 58.62, H, 4.29, N, 17.47; TLC: R$_f$=0.13 (SiO$_2$, CHCl$_3$/MeOH)=10:1; mp: 173–174° C.

EXAMPLE 116
N-(5-Acenaphthyl)-N'-[4-(6-methyl-benzothiazole) phenylguanidine].HCl $^1$H NMR (CD$_3$OD): δ ppm 8.15–8.17 (m, ArH, 2H), 7.36–7.91 (m, ArH, 10H), 3.40–3.50 (m, CH$_2$, 4H), 2.50 (s, CH$_3$, 1H); MS(EI): m/e 434.1 (M$^+$: C$_{27}$H$_{22}$N$_4$S); Anal. (C, H. N; C$_2$H$_{22}$N$_4$S.HCl): Calcd. (%): C, 68.85, H, 4.92, N, 11.89; Found (%): C, 68.66, H, 4.91, N, 11.86; TLC: R$_f$=0.23 (SiO$_2$, CHCl$_3$MeOH)=10:1; mp: 244.5–246° C.

EXAMPLE 117
N-(5-Acenaphthyl)-N'-(1-benz[cd]indolinyl)guanidine.HCl $^1$H NMR (CD$_3$OD): δ ppm 7.90–7.40 (m, ArH, 11H), 5.66 (s, NCH$_2$, 2H), 3.49 (m, 2CH$_2$, 4H); MS(EI): m/e 349.2 (M$^+$: C$_{24}$H$_{19}$N$_3$); Anal. (C, H, N; C$_{24}$H$_{19}$N$_3$.HCl): Calcd. (%): C, 74.70, H, 5.22, N, 10.89; Found: C, 74.61, H, 5.08, N, 10.63; TLC: R$_f$=0.51 (SiO$_2$, CH$_2$Cl$_2$/MeOH=10/1); mp: 245–246° C.

EXAMPLE 118
N-(5-Acenaphthyl)-N'-(6-benz[cd]indo-2[1H]-one) guanidine.HCl $^1$H NMR (CD$_3$OD): δ ppm 8.25–7.04 (m, ArH, 1OH), 3.45–3.43 (m, CH$_2$, 4H); MS(EI): m/e 378.3 (M$^+$: C$_{24}$H$_{18}$ON$_4$); Anal. (C, H, N; C$_{24}$H$_{18}$ON$_4$.HCl): Calcd. (%): C, 69.48, H, 4.62, N, 13.50; Found (%): C, 69.36, H, 4.72, N, 13.27; TLC: RI=0.26 (SiO$_2$, CH$_2$Cl$_2$/MeOH=10/1); mp: 327–328° C.

EXAMPLE 119
N,N'-Bis(6-benz[cd]indolinyl-2[1H]-one)guanidine.HBr $^1$H NMR (DMSO): δ ppm 11.00–7.00 (m, ArH, 10H); MS(EI): m/e 393.2 (M$^+$: C$_{23}$H$_{15}$N$_5$O$_2$); Anal. (C, H, N; C$_{24}$H$_{18}$N$_4$O.HCl): Calcd. (%): C, 58.24, H, 3.40, N, 14.77; Found (%): C, 58.25, H, 3.25, N, 14.80; TLC: R$_f$=0.25 (SiO$_2$, CH$_2$Cl$_2$/MeOH=10/1); mp: 390–391° C.

EXAMPLE 120
N-(4-Butoxyphenyl)-N'-(4-chlorophenylethyl) guanidine.HCl (4-(CH$_3$CH$_2$CH$_2$CH$_2$O)CH$_4$NHC(=NH)NH((4-(Cl)C$_6$H$_4$)CH$_2$CH$_2$).HCl)

Purple solid: mp: 163–164° C.; R$_f$=0.026 (9:1 EtOAc:MeOH); $^1$H NMR (300 MHz, CD$_3$OD): δ 7.23–7.38 (m, 4H, ArH), 6.92–7.10 (m, 4H, ArH), 3.95–4.15 (t, 2H, CH$_2$), 3.50–3.58 (t, 2H, CH$_2$), 2.88–2.93 (m, 2H, CH$_2$), 1.72–1.81 (m, 2H, CH$_2$), 1.71–1.81 (m, 2H, CH$_2$), 1.44–1.58 (m, 2H, CH$_2$), 0.95–1.20 (m, 2H, CH$_3$); MS(Cl): m/e 346 (M$^+$ for free base); Anal. Calcd. for Cl$_9$H$_{24}$N$_3$ClO.HCl.0.10H$_2$O: C, 59.40, H, 6.61, N. 10.93; Found: C, 59.15, H, 6.31, N, 10.84.

EXAMPLE 121
N-(4-Benzyloxyphenyl)-N,N'-diphenylguanidine.oxalate

White solid: mp: 145° C.; $^1$H NMR (300 MHz, CD$_3$OD): δ 7.30–7.50 (m, 15H, ArH), 7.20–7.25 (d, J=9 Hz, 2H, ArH), 7.02–7.07 (d, 2H, ArH), 5.10 (s, 2H, ArCH$_2$O—); HPLC: 97.6% pure; MS(EI): m/e 393 (M$^+$ for free base); Anal. Calcd. for C$_{26}$H$_{23}$N$_3$O.0.8C$_2$H$_2$O$_4$: C, 71.21, H, 5.33, N, 9.03; Found: C, 70.87, H, 5.11, N, 9.05.

EXAMPLE 122
N-(4-Benzyloxyphenyl)-N'-benzyl-N'-phenylguanidine.oxalate

White solid: mp: 180° C.; $^1$H NMR (300 MHz, CD$_3$OD): δ 7.30–7.50 (m, 15H, ArH), 7.20–7.25 (d, J=9 Hz, 2H, ArH), 7.05–7.10 (d, J=9 Hz, 2H, ArH), 5.13 (s, 2H, Ph—CH$_2$O—), 5.08 (s, 2H, Ph—CH$_2$N—); HPLC: 99.4% pure; MS(EI): m/e 407 (M+ for free base); Anal. Calcd. for C$_{27}$H$_{25}$N$_3$O.C$_2$H$_2$O$_4$.0.5H$_2$O: C, 68.76, H, 5.57, N, 8.30; Found: C, 68.96, H, 5.36, N, 8.47.

EXAMPLE 123
N-(3-Benzyloxyphenyl)-N'-(4-benzylthiophenyl)guanidine.mesylate ((3-(C$_6$H$_4$CH$_2$O)C$_6$H$_4$)NHC(=NH)NH(4-(C$_6$H$_4$CH$_2$S)C$_6$H$_4$) mesylate)

White solid: mp: 142–143° C.; $^1$H NMR (300 MHz, CD$_3$OD): δ 7.19–7.45 (m, 15H, ArH), 6.88–7.00 (m, 18H, ArH), 5.12 (s, 2H, S-CH$_2$), 4.20 (s, 2H, O—CH$_2$) 2.70 (s, 3H, Mesylate CH$_3$); HPLC: 96.6% pure; MS(EI): m/e 440 (M$^+$ for free base); Anal. Calcd. for C$_{27}$H$_{25}$N$_3$OS.CH$_3$SO$_3$H: C, 62.78, H, 5.46, N, 7.84; Found: C, 62.83, H, 5.49, N, 7.83.

EXAMPLE 124
N,N'-Bis(4(pentylthio)phenyl)guanidine.HBr

White solid: mp: 153° C.; $^1$H NMR (300 MHz, CD$_3$OD): δ 7.41–7.90 (m, 18H, ArH); MS(EI): m/e 427 (M$^+$ for free base); Anal. Calcd. for C$_{25}$H$_{21}$N$_3$S$_2$.HBr.0.5H$_2$O: C, 58.02, H, 4.48, N, 8.12; Found: C, 57.94, H, 4.27, N, 8.09.

EXAMPLE 125
N,N'-Bis(3-(phenylthio)phenyl)guanidine.oxalate

White solid: mp: 108° C.; MS(EI): m/e 415 (M$^+$ for free base); Anal. Calcd. for C$_{25}$H$_{35}$N$_3$O$_4$S$_2$.0.75H$_2$O: C, 57.83, H, 7.09, N, 8.09; Found: C, 57.94, H, 6.71, N, 8.34.

EXAMPLE 126
N-(5-Acenaphthyl)-N'-(2-phenylethyl)guanidine.HCl

Yellow solid: mp: 98–101° C.; R$_f$=0.13 (10:1; CHCl$_3$/MeOH): $^1$H NMR (300 MHz, CD$_3$OD): δ 7.25–7.57 (m, 10H, ArH), 3.56–3.59 (Brs, 2H, CH$_2$), 3.40–3.49 (m, 4H, CH$_2$), 2.90–2.94 (t, 2H, J=14 Hz, CH$_2$); MS(EI): m/e 315 (M+ for free base); Anal. Calcd. for C$_{21}$H$_{21}$N$_3$.HCl: C, 71.68, H, 6,30, N, 11.94; Found: C, 71.44, H, 6.26, N, 11.77.

EXAMPLE 127
N-45-Acenaphthyl)-N'-(3-butoxypropyl)guanidine.HCl

Brown semicrystalline solid: R$_f$=0.19 (10:1; CHCl$_3$MeOH): $^1$H NMR (300 MHz, CD$_3$OD): δ 6.62–7.57 (m, 5H, ArH), 3.31–3.49 (m, 10H, CH$_2$), 1.61–1.65 (m, 2H, CH$_2$), 1.31–1–44 (m, 2H, CH$_2$), 1.25–1.31 (m, 2H, CH$_2$) 1.20–1.25 (m, 3H, CH$_3$); MS(EI): m/e 325 (M$^+$ for free base); Anal. Calcd. for C$_{20}$H$_{27}$N$_3$O.HCl: C, 66.37, H, 7.80, N, 11.61; Found: C, 71.80, H, 7.27, N, 8.71.

EXAMPLE 128
N,N'-Bis(2, 2-diphenylethyl)guanidine.HBr

White solid: mp: 179–180° C., R$_f$=0.20 (10:1; CHCl$_3$/MeOH): $^1$H NMR (300 MHz, CD$_3$OD): δ 7.21–7.36 (m, 20H, ArH), 3.76–3.79 (m, 4H, CH$_2$); MS(EI): m/e 420 (M$^+$ for free base); Anal. Calcd. for C$_{29}$H$_{29}$N$_3$.HBr: C, 69.6, H, 6.04, N, 8.4; Found: C, 69.43, H, 5.96, N, 8.27.

EXAMPLE 129
N-(4-Butoxyphenyl)-N-(4-chlorobenzhydryl)guanidine.HCl

Purple solid: mp: 81–82° C.; R$_f$=0.53 (10:2; CHCl$_3$/MeOH); $^1$H NMR (300 MHz, CD$_3$OD): δ 6.15–7.40 (m, 13H, ArH), 3.94–3.99 (m, 2H, CH$_2$), 1.69–1.81 (m, 2H, CH$_2$), 1.42–1.55 (m, 2H, CH$_2$), 0.95–1.0 (m, 3H, CH$_3$); MS(Cl): m/e 408 (M$^+$ for free base); Anal. Calcd. for C$_{24}$H$_{26}$N$_3$OCl.HCl.1/3H$_2$O: C, 63.85, H, 6.61, N, 4.73; Found: C, 63.80, H, 6.33, N, 9.59.

EXAMPLE 130
(5-Acenaphthyl)-N'-(phenethyl)-N'-benzylguanidine.maleate

White solid: mp: 160° C.; $^1$H NMR (300 MHz, CD$_3$OD): 67.30–7.52 (m, 14H, ArH), 7.13–7.19 (m, 2H, ArH), 6.23 (s, 2H, maleate H), 4.83 (s, 2H, N-benzyl), 3.843.91 (t, 2H, N—CH$_2$), 3.40–3–47 (Brs, 4H, Acenaphthyl CH$_2$), 3.06–3.12 (t, J=7 Hz, 2H, Ph—CH$_2$—); MS(EI): m/e 406 (M$^+$ for free base); Anal. Calcd. for C$_{28}$H$_{27}$N$_3$.C$_4$O$_4$: C, 73.68, H, 5.99, N, 8.06; Found: C, 73.80, H, 6.09, N, 8.10.

EXAMPLE 131
N-4-Benzyloxyphenyl)-N'-(3-benzyloxyphenyl)-N'-(4-chlorobenzyl)guanidine-mesylate White solid: mp: 145–147°; R$_f$=0.30 (10:1; CHCl$_3$/MeOH); $^1$H NMR (300 MHz, CD$_3$OD): δ 6.91–7.45 (m, 22H, ArH), 5.12 (s, 2H, CH$_2$), 5.06 (s, 2H, CH$_2$), 5.01 (s, 2H, CH$_2$), 2.70 (s, 3H, CH$_3$); MS(EI): m/e 548 (M$^+$ for free base); Anal. Calcd. for C$_{34}$H$_{30}$N$_3$O$_2$Cl.CH$_3$SO$_3$H: C, 62.67, H, 5.56, N, 6.27; Found: C, 62.82, H, 5.42, N, 6.73.

EXAMPLE 132
N,N'-Bis(4-benzyloxyphenyl)-N'-methylguanidine.mesylate

White solid: mp: 168–171° C.; R$_f$=0.14 (10:1; CHCl$_3$/MeOH); $^1$H NMR (300 MHz, CD$_3$OD): δ 7.32–7.45 (m, 12H, ArH), 7.06–7.22 (m, 6H, ArH), 5.11–5.14 (d, 4H, J=8 Hz, CH$_2$), 3.42 (s, 3H, CH$_3$), 2.69 (s, 3H, CH$_3$); MS(EI): m/e 437 (M$^+$ for free base); Anal. Calcd. for C$_2$8H$_{27}$N$_3$O$_2$.CH$_3$SO$_3$H.1/4H$_2$O: C, 64.72, H, 5.90, N, 7.81; Found: C, 64.56, H, 5.87, N, 7.80.

EXAMPLE 133
N-(3-Benzyloxyphenyl)-N'-(4-benzyloxyphenyl)-N'-phenylguanidine.HCl White, grey solid: mp: 72–74° C.; R$_f$=0.20; (10:1; CHCl$_3$/MeOH); $^1$H NMR (300 MHz, CD$_3$OD): 6 7.21–7.43 (m, 18H, ArH), 7.00–7.03 (d, 2H, J=9 Hz, ArH), 6.70–6.79 (m, 3H, ArH), 5.08 (s, 4H, CH$_2$); MS(Cl): m/e 500 (M$^+$ for free base); Anal. Calcd. for C$_{33}$H$_{29}$N$_3$O$_2$.HCl: C, 73.94, H, 5.64, N, 7.84; Found: C, 74.09, H, 5.41, N, 7.96.

EXAMPLE 134
N-(4-sec-Butylphenyl)-N'-(4-isopropoxyphenyl)-N'-phenylguanidine.HCl White solid: mp: 190–192° C.; R$_f$=0.59 (10:2; CHCl$_3$/MeOH); $^1$H NMR (300 MHz, CD$_3$OD): δ 6.97–7.51 (m, 13H, ArH), 4.59–4.89 (m, 1H, CH), 2.58–2.68 (m, 1H, CH), 1.53–1.66 (m, 2H, CH$_2$) 1.28–1.32 (m, 6H, CH$_3$), 1.20–1.25 (m, 3H, CH$_3$), 0.79–0.84 (m, 3H, CH$_3$); MS(Cl): m/e 402 (M$^+$ for free base); Anal. Calcd. for C$_{26}$H$_{31}$N$_3$O.HCl.1/2H$_2$O: C, 68.48, H, 7.51, N, 9.21; Found: C, 69.81, H, 7.30, N, 9.89.

EXAMPLE 135
N-(4-Benzyloxyphenyl)-N'-(4-benzyloxyphenyl)-N'-phenylguanidine.mesylate White solid: mp: 168–170° C.; $R_f$=0.59 (9:3; EtOAc/MeOH); $^1$H NMR (300 MHz, CD$_3$OD): δ 7.21–7.46 (m, 19H, ArH), 7.04–7.11 (m, 4H, ArH), 5.10–5.11 (m, 4H, CH$_2$), 2.69 (s, 3H, CH$_3$); MS(EI): m/e 499 (M$^+$ for free base); Anal. Calcd. for C$_{33}$H$_{29}$N$_3$O$_2$.1.5CH$_3$SO$_3$H: C, 63.97, H, 5.24, N, 6.51; Found: C, 63.97, H, 5.09, N, 6.57.

EXAMPLE 136
N,N'-Bis(3-octyloxyphenyl)guanidine.HCl

Light purple solid: mp: 107–108° C.; $R_f$=0.196 (10:1; CHCl$_3$MeOH); $^1$H NMR (300 MHz, CD$_3$OD): δ 7.32–7.38 (t, 2H, J=10 Hz, ArH), 6.88–6.91 (m, 6H, ArH), 4.01–4.89 (m, 4H, CH$_2$), 1.75–1.80 (m, 4H, CH$_2$), 1.40–1.47 (m, 4H, CH$_2$), 1.31–1.40 (m, 16H, CH$_2$), 0.88–0.93 (t, 6H, J=8 Hz, CH$_3$); MS(EI): m/e 467 (M$^+$ for free base); Anal. Calcd. for C$_{29}$H$_{45}$N$_3$O$_2$.HBr.1/2H$_2$O: C, 62.56, H, 8.52, N, 7.55; Found: C, 62.80, H, 8.18, N, 7.63.

EXAMPLE 137
N,N'-Bis(4-butoxyphenyl)guanidine.HBr

Cream solid: mp: 88° C.; $R_f$=0.11 (10:1; CHCl$_3$/MeOH); $^1$H NMR (300 MHz, CD$_3$OD): δ 7.23–7.26 (d, 4H, ArH), 6.99–7.02 (d, 4H, J=9 Hz, ArH), 3.98–4.02 (t, 4H, J=13 Hz, CH$_2$), 1.74–1.79 (m, 4H, CH$_2$), 1.47–1.54 (m, 4H, CH$_2$), 0.96–1.01 (t, 6H, J=13 Hz, CH$_3$); MS(EI): m/e 355 (M$^+$ for free base); Anal. Calcd. for C$_{21}$H$_{29}$N$_3$O$_2$.HBr.1.0H$_2$O: C, 57.80, H, 6.93, N, 9.63; Found: C, 55.17, H, 6.77, N, 10.36.

EXAMPLE 138
N,N'-Bis(4-phenoxyphenyl)guanidine.HBr

White solid: mp: 127–128° C.; $R_f$=0.18 (10:1; CHCl$_3$/MeOH); $^1$H NMR (300 MHz, CD$_3$OD): δ 7.31–7.41 (m, 8H, ArH), 7.02–7–18 (m, 1OH, ArH); MS(EI): m/e 395 (M$^+$ for free base); Anal. Calcd. for C$_{25}$H$_{21}$N$_3$O$_2$.HBr: C, 63.03, H, 4.65, N, 8.82; Found: C, 62.77, H, 4.66, N, 8.84.

EXAMPLE 139
N-(3-Benzyloxyphenyl)-N'-(4-phenoxyphenyl)guanidine.mesylate

White solid: mp: 89–90° C.; $R_f$=0.18 (10:1; CHCl$_3$:MeOH); $^1$H NMR (300 MHz, CD$_3$OD): 67.30–7.45 (m, 10H, ArH), 7.15–7.30 (t, 1H, J=10 Hz, ArH), 6.91–7.07 (m, 7H, ArH), 5.12 (s, 2H, CH$_2$), 2.69 (s, 3H, CH$_3$); MS(EI): m/e 409 (M$^+$ for free base); Anal. Calcd. for C$_2$,H$_{32}$N$_3$O$_2$.CH$_3$SO$_3$H: C, 64.14, H, 5.38, N, 8.31; Found: C, 53.85, H, 5.38, N, 8.30.

EXAMPLE 140
N-(3-Benzyloxyphenyl)-N'-(4-phenylazophenyl)guanidine.mesylate

Yellow orange solid: mp: 206–208° C.; $R_f$=0.12 (10:1; CHCl$_3$:MeOH); $^1$H NMR (300 MHz, CD$_3$OD): δ 8.00–8.03 (m, 2H, ArH), 7.91–7.94 (m, 2H, ArH), 7.33–7.56 (m, 11H, ArH), 6.947.01 (m, 3H, ArH), 5.13 (s, 2H, CH$_2$), 2.69 (s, 3H, CH$_3$); MS(EI): m/e 421 (M$^+$ for free base); Anal. Calcd. for C$_{26}$H$_{23}$N$_5$O.CH$_3$SO$_3$H.0.25H$_2$O: C, 62.11, H, 5.31, N, 13.42; Found: C, 61.86, H, 5.34, N, 13.25.

EXAMPLE 141
N,N'-Bis(3-benzyloxyphenyl)-N'-methylguanidine.HCl

White solid: mp: 41–42° C.; $R_f$=0.44 (10:2; CHCl$_3$:MeOH); $_1$H NMR (300 MHz, CD$_3$OD): δ 7.29–7.45 (m, 12H, ArH), 6.80–7.08 (m, 6H, ArH), 5.10–5.12 (d, 4H, J=8 Hz, CH$_2$), 3.42 (s, 3H, CH$_3$); MS(EI): m/e 437 (M$^+$ for free base); Anal. Calcd. for C$_{28}$H$_{27}$N$_3$O$_2$.HCl.CH$_3$OH: C, 68.83, H, 6.37, N, 8.30; Found: C, 69.13, H, 5.95, N, 8.09.

EXAMPLE 142
N-(4-Benzyloxphenyl)-N'-(4-benzyloxyphenyl)-N'-methylguanidine.mesylate Purple-white solid: mp: 138–140° C.; $R_f$=0.09 (10:1; CHCl$_3$:MeOH); $^1$H NMR (300 MHz, CD$_3$OD): δ 7.31–7.45 (m, 13H, ArH), 7.11–7.14 (m, 2H, ArH), 6.86–7.00 (m, 3H, ArH), 5.10–5.14 (d, 4H, J=10 Hz, CH$_2$), 3.43 (s, 3H, CH$_3$), 2.68 (s, 3H, CH$_3$); MS(EI): m/e 437 (M$^+$ for free base); Anal. Calcd. for C$_{28}$H$_{27}$N$_3$O$_2$.CH$_3$SO$_3$H.0.25H$_2$O: C, 64.72, H, 5.90, N, 7.81; Found: C, 64.73, H, 5.96, N, 7.74.

EXAMPLE 143
N-(4-Butoxyphenyl)-N'-(4-isopropoxyphenyl)-N'-phenylguanidine.HCl (4(CH$_3$CH$_2$CH$_2$CH$_2$O)C$_6$H$_4$)NHC(=NH)N[(4-((CH$_3$)$_2$CHO)C$_6$H$_4$)][C$_6$H$_5$].HCl Purple solid: mp: 161–164° C.; $^1$H NMR (300 MHz, CD$_3$OD): 6 6.93–7.47 (m, 13H, ArH), 4.58–4.62 (m, 1H, CH), 3.94–3.98 (t, 2H, J=13 Hz, CH$_2$), 1.68–1.79 (m, 2H, CH$_2$), 1.42–1.57 (m, 2H, CH$_2$), 0.93–1.00 (t, J=15 Hz, 3H, CH$_3$); MS(EI): m/e 418 (M$^+$ for free base); Anal. Calcd. for C$_{26}$H$_{31}$N$_3$O$_2$.HCl: C, 68.78, H, 7.10, N, 9.26; Found: C, 68.79, H, 7.22, N, 9.36.

EXAMPLE 144
N-N'-Bis(4-(4-hydroxybutyl)phenyl)guanidine.HBr

Light yellow solid: mp: 143–44° C.; $R_f$=0.16 (10:2; CHCl$_3$:MeOH); $^1$H NMR (300 MHz, CD$_3$OD): δ 7.23–7.33 (m, 8H, ArH), 3.55–3.59 (m, 4H, CH$_2$), 2.65–2.69 (m, 4H, CH$_2$), 1.62–1.70 (m, 4H, CH$_2$), 1.56–1.62 (m, 4H, CH$_2$); MS(Cl): m/e 356 (M$^+$ for free base); Anal. Calcd. for C$_{21}$H$_{29}$N$_3$O$_2$.HBr.0.5H$_2$O: C, 56.62, H, 7.01, N, 9.43; Found: C, 56.39, H, 6.67, N, 9.34.

EXAMPLE 145
N-(4-Butoxyphenyl)-N'-(3-methoxyphenyl)-N'-phenylguanidine.HCl

Tan solid: mp: 79–81° C.: $R_f$=0.043 (10:1; CHCl$_3$:MEOH); $^1$H NMR (300 MHz, CD$_3$OD): δ 7.23–7.51 (m, 6H, ArH), 7.23–7.26 (m, 2H, ArH), 6.96–7.02 (m, 5H, ArH), 3.95–4.20 (t, 2H, CH$_2$), 3.80 (s, 3H, CH$_2$), 1.70–1.80 (m, 2H, CH$_2$), 1.45–1.56 (m, 2H, CH$_2$), 0.94–1.10 (m, 3H, CH$_3$); MS(Cl): m/e 390 (M$^+$ for free base); Anal. Calcd. for C$_{24}$H$_{27}$N$_3$O$_2$.HCl.0.5H$_2$O: C, 66.27, H, 6.72, N, 9.60; Found: C, 65.97, H, 6.69, N, 9.76.

EXAMPLE 146
Inhibition of Glutamate Release

Compounds were tested for the inhibition of glutamate release. As shown by the data below, compounds of the invention are effective blockers of glutamate release. The assay involves adaptation of a rapid superfusion system (said system disclosed in S. Goldin, U.S. Pat. No. 4,891,185 (1990); Turner, T. J. et al., *Anal. Biochem.*, 178:8–16 (1989)) to measure depolarization-induced $^3$H-glutamate release from brain nerve terminals. The depolarizing stimulus opens presynaptic voltage-activated ion channels as the key step required to initiate Ca-dependent exocytosis of glutamatergic synaptic vesicles. The method involves preloading rat brain synaptosomes with $^3$H-glutamate via the Na-dependent glutamate uptake system. The preloaded nerve terminals are retained in a superfusion chamber accessed by high-speed, solenoid-driven valves. Microcomputer-operated circuitry controls the timing of valve operation; the valves control the delivery under nitrogen pressure of pulses of depolarizing buffer, Ca, and/or drugs to the synaptosomes. The $^3$H-glutamate-containing effluent is continuously collected in a high speed fraction collector on a subsecond timescale as short as 30 msec (300 msec fractions were employed herein). The high solution flow rate and minimal dead volume of the superfusion chamber, afford rapid solution changes and precise control of the chemical microenvironment of the nerve terminal preparation.

More specifically, the assay method employed was as described in Goldin et al., PCT/US92/01050, with the following modifications. Introduction of a buffer containing high [$K^+$] was the means employed to produce the depolarization. This mode of depolarization is the preferred method of opening presynaptic voltage-activated Ca channels to trigger glutamate release. An additional method of depolarization was also employed, namely introduction of veratridine, and a parallel set of such veratridine-based experiments was performed. Veratridine is known to stimulate neurotransmitter release by opening voltage-activated Na channels, which results in depolarization of the nerve terminal plasma membrane and in turn, secondarily, opens presynaptic Ca channels to directly trigger $^3$H-glutamate release via Ca-dependent exocytosis. The use of veratridine-induced glutamate release was employed to detect compounds of the invention which may block neurotransmitter release by blocking voltage-activated presynaptic Na channels. It has been previously reported that tetrodotoxin, a highly specific blocker of Type I and Type II neuronal Na channels, blocks veratridine-induced $^3$H-glutamate release with no effect on high [$K^+$]-induced $^3$H-glutamate release (Katragadda et al. *Abs. Soc. for Neurosci.* 19:1750 (1993)). In experiments measuring veratridine-induced glutamate release, 50 μM veratridine in "basal" buffer was substituted for the "high-K buffer" employed as described in PCT/US92/01050; the protocol was otherwise identical to that described therein. In superfusion solutions containing compounds to be tested, compounds were made as stock solutions in methanol and diluted so that the final concentration of methanol never exceeded 0.3% (v/v). All solutions including compound free controls contained the same solvent [methanol]. Results are shown in the below tables (1a–1f) identified together as Table I. In that Table and tables of other examples which follow, the designation "FB" refers to the free base form of the specified compound.

TABLE 1

Inhibition of $^3$H-glutamate release in brain nerve terminal preparations

TABLE 1a

Compounds of Formula IA

| Example No. | Name | % Inhibition of $^3$H-Glu Rel @ 3 μM | @ 1 μM | Salt |
|---|---|---|---|---|
| 1 | N-(4-sec-butylphenyl)-N-(4-tert-butylbenzyl)guanidine | 61 | 67* | HCl |
| 2 | N-(5-acenaphthyl)-N-(4-tert-butylbenzyl)guanidine | 61 | 52 | FB |
| 19 | N-(5-acenaphthyl)-N-(4-iso-propylbenzyl)guanidine | 81* | | HCl |
| 23 | N-(4-sec-butylphenyl)-N-(transcinnamyl)guanidine | 33* | | HCl |
| 24 | N-(4-n-butoxyphenyl)-N-(4-tert-butylbenzyl)guanidine | | 62* | HCl |
| 27 | N-(3-trifluoromethoxy-phenyl)-N-(4-tert-butylbenzyl)guanidine | | 24 | HCl |
| 47 | N-(1-naphthyl)-N-(4-tert-butylbenzyl)guanidine | | 40 | HCl |

TABLE 1a-continued

Compounds of Formula IA

| Example No. | Name | % Inhibition of $^3$H-Glu Rel @ 3 μM | @ 1 μM | Salt |
|---|---|---|---|---|
| 48 | N-(3-iodophenyl)-N-4-tert-butylbenzyl)guanidine | | 23* | HCl |
| 49 | N-(4-chloronaphthyl)-N-(4-tert-butylbenzyl)guanidine | | 32* | HCl |
| 52 | N-(1-naphthylmethyl)-N'-(4-tert-butylbenzyl)guanidine | 55* | | HCl |
| 53 | N-(5-acenaphthyl)-N-(3-phenoxybenzyl)guanidine | | 37 | HCl |
| 58 | N-(5-acenaphthyl)-N-(4-iodobenzyl)guanidine | | 43 | HCl·3/2H$_2$O |
| 59 | N-(5-acenaphthyl)-N-(4-trifluoromethoxy-benzyl)guanidine | | 44 | HCl·2H$_2$O |

TABLE 1b

Compounds of Formula II

| Example No. | Name | % Inhibition of $^3$H-Glu Rel @ 3 μM | @ 1 μM | Salt |
|---|---|---|---|---|
| 9 | N,N'-bis(fluoranthyl)guanidine | 17* | | HBr |

TABLE 1c

Compounds of Formula IIIA

| Example No. | Name | % Inhibition of $^3$H-Glu Rel @ 3 μM | @ 1 μM | @ 0.3 μM | Salt |
|---|---|---|---|---|---|
| 3 | N-(5-acenaphthyl)-N'-benzhydrylguanidine | 53 | | | HCl |
| 10 | N-(5-acenaphthyl)-N'-(1-naphthylmethylene)guanidine | 71* | 24* | | mesylate |
| 40 | N-(5-acenaphthyl)-N'-(1-methyl-2-(4-chloro-phenyl)ethyl)guanidine | | 64 | 46 | HCl |
| 41 | N-(5-acenaphthyl)-N'(1,2-diphenylethyl)guanidine | | 52 | | HCl |
| 42 | N-(5-acenaphthyl)-N'-(3-phenyl propyl)guanidine | 60* | | | HCl |
| 43 | N-(5-acenaphthyl)-N'-(2-methyl-2-phenyl-ethyl)guanidine | 60 | 43* | | HCl |
| 44 | N-(5-acenaphthyl)-N'-(2-methyl-2-phenyl-ethyl)guanidine | 71* | 43* | | HCl |
| 60 | N-(5-acenaphthyl)-N'-((4-tert-butylphenyl)-(4-sec-butylphenyl)-methyl)guanidine | 32 | | | HCl |

TABLE 1d

Compounds of Formula IV

| Example No. | Name | % Inhibition of ³H-Glu Rel @ 3 μM | @ 1 μM | @ 0.3 μM | Salt |
|---|---|---|---|---|---|
| 4 | N-N'-bis(4-sec-butylphenyl(guanidine | 85 | 52 | | FB |
| 5 | N,N'-bis(4-sec-butyl-phenyl)-N-methyl guanidine | | 68* | | HCl |
| 6 | N,N'-bis(4-sec-butyl-phenyl)-N,N'-bismethyl guanidine | 92 | 71 | | HCl |
| 8 | N,N'-bis(4-sec-butyl-phenyl)-2-iminopyrimid-azolidine | 50 | | | HBr |
| 13 | N,N'-bis(4-tert-butylphenyl)guanidine | 70 | 62* | | FB |
| 14 | N-(4-tert-butylphenyl)-N'-(2,3,4-trichloro phenyl)guanidine | 63 | | | HCl |
| 15 | N-(4-methoxynaphthyl)-N'-(2,3,4-trichloro-phenyl)guanidine | 88 | | | HCl |
| 30 | N,N'-bis(3-biphenyl)guanidine | | 25 | | |
| 31 | N,N'-di-(3-tert-butylphenyl)guanidine | | 24 | | HBr |
| 34 | N,N'-bis-(3-sec-butyl-phenyl)guanidine | | 63 | | HBr |
| 35 | N,N'-bis(4-tert-butyl-phenyl)-N-methylguanidine | | 61 | | HCl |
| 36 | N,N'-bis(4-tert-butyl-phenyl)-N,N'-methyl-guanidine | | 67 | | FB |
| 37 | N,N'-bis(4-n-butylphenyl) guanidine | | 100 | 57 | mesylate |
| 42 | N-(3-benzyloxyphenyl)-N'-(4-benzyloxyphenyl) guanidine | | 90 | 54 | HCl |
| 45 | N,N'-bis(sec-butylphenyl)-N'-(2-phenoxyethyl)-guanidine | | 57 | | HCl |
| 46 | N,N'-bis(sec-butylphenyl)-N'-(n-pentyl)guanidine | | 100 | 65 | HCl |

TABLE 1e

Compounds of Formula V

| Example No. | Name | % Inhibition of ³H-Glu Rel @ 3 μM | @ 1 μM | Salt |
|---|---|---|---|---|
| 7 | N-5-acenaphthyl)-N'-(1,2,3,4-tetrahydroquino-linyl)guanidine | 16 | 20 | Mesylate |
| 29 | N-(5-acenaphthyl)-N-(indolynyl)guanidine | 22 | | FB |

*Results of veratridine-induced glutamate release assay as specified above.

TABLE 1f

Additional Compounds of the Invention
(Including Compounds of Formulas I–V)

| Ex. No. | Name | % Inhibition of ³H-Glu Rel @ 3 μM | @ 1 μM | @ 0.3 μM | @ 0.1 μM | Salt |
|---|---|---|---|---|---|---|
| 62 | N-(3-sec-butyl-phenyl)-N-(4-tert-butylbenzyl)guani-dine | | 22 | | | HCl |
| 63 | N-(3-tert-butyl-phenyl)-N-(4-tert-butylbenzyl)guani-dine | | 40 | | | HCl |
| 64 | N-(3-pentoxy-phenyl)-N-(4-tert-butylbenzyl)guani-dine | | 41 | | | HCl |
| 65 | N-(5-acenaphthyl)-N-(4-benzyloxy-benzyl)guanidine | | 42 | | | HCl |
| 66 | N-(4-sec-butyl-phenyl)-N-(4-benzyloxy-benzyl)guanidine | | 54 | | | HCl |
| 67 | N-(4-benzyloxy-phenyl)-N-(4-benzyloxy-benzyl)guanidine | | 36 | | | HCl |
| 68 | N-(5-acenaphthyl)-N-(3-benzyl-oxybenzyl)guani-dine | | 76 | | | HCl |
| 72 | N-(4-sec-butyl-phenyl)-N-(4-t-butylbenzyl)-N'-pyrrolidinyl-guanidine | | | 48 | | HCl |
| 73 | N-(4-sec-butyl-phenyl)-N-(4-t-butylbenzyl)-N'-(4-thiomorpholinyl)-guanidine | | 59 | | | HCl |
| 74 | N-(4-sec-butyl-phenyl)-N-(4-tert-butylbenzyl)-N'-piperidinylguanidine | | 100 | 21 | | HCl |
| 75 | N-(4-sec-butyl-phenyl)-N-(4-tert-butylbenzyl)-N'-(4-morpholinyl)-guanidine | | | 42 | | HCl |
| 76 | N-(4-sec-butyl-phenyl)-N-(4-tert-butylbenzyl)-N'-(4-propylpiperi-dinyl)guanidine | | | 45 | | HCl |
| 77 | N-(4-butoxyphenyl)-N-(4-tert-butyl-benzyl)-N'-(4-piperidinyl)guani-dine | | | 44 | | HCl |
| 78 | N-(4-sec-butyl-phenyl)-N-(4-tert-butylbenzyl)-N'-(4-benzyl-piperidinyl)guani-dine | | 22 | | | mesylate |
| 79 | N-(4-benzyloxy-phenyl)-N-(4-tert-butylbenzyl)-N'-(4-morpholinyl)-guanidine | | 77 | | | HCl |
| 80 | N-(4-sec-butyl-phenyl)-N-(4-tert-butylbenzyl)-N'-(1,2,3,4- | | 68 | | | HCl |

TABLE 1f-continued

Additional Compounds of the Invention
(Including Compounds of Formulas I–V)

| Ex. No. | Name | % Inhibition of ³H-Glu Rel @ 3 μM | @ 1 μM | @ 0.3 μM | @ 0.1 μM | Salt |
|---|---|---|---|---|---|---|
|  | tetrahydroisoquinolinyl)guanidine |  |  |  |  |  |
| 82 | N-(4-sec-butyl-phenyl)-N-(4-tert-butylbenzyl-N'-(3,5-dimethyl-4-morpholinyl)guanidine |  |  | 60 |  | HCl |
| 83 | N-(4-tert-butyl-phenyl)-N-(4-tert-butylbenzyl)-N'-(4-sec-butylphenyl)-N'-(methyl)guanidine |  | 63 | 31 |  | HCl |
| 84 | N-(4-sec-butyl-phenyl)-N-(4-tert-butylbenzyl-N'-(4-sec-butylphenyl)-N'-(methyl)-guanidine |  | 37 |  |  | HCl |
| 85 | N-(4-sec-butyl-phenyl)-N-(4-tert-butylbenzyl)-N'-(phenyl)guanidine |  | 100 | 55 |  | HCl |
| 86 | N-(4-sec-butyl-phenyl)-N-(4-tert-butylbenzyl)-N'-(4-chlorophenyl)-guanidine |  |  | 45 | 16 | HCl |
| 87 | N-(4-butoxyphenyl)-N-(4-tert-butyl-benzyl)-N'-(phenyl)guanidine |  |  | 36 |  | HCl |
| 88 | N-(4-sec-butyl-phenyl)-N-(4-tert-butylbenzyl)-N'-(phenyl)-N'-methylguanidine |  |  | 77 |  | HCl |
| 89 | N-(4-sec-butyl-phenyl)-N-(4-tert-butylbenzyl)-N'-(3,4-dichloro-phenyl)guanidine |  |  | 21 |  | HCl |
| 90 | N-(4-hexylphenyl)-N-(4-hexylbenzyl)-N'-phenylguanidine |  |  | 42 |  | HCl |
| 91 | N-(4-sec-butyl-phenyl)-N-(4-tert-butylbenzyl)-N'-(4-benzyloxy-phenyl)guanidine |  |  | 49 |  | mesylate |
| 92 | N,N'-bis-(4-tert-butylphenyl)-N,N'-dimethylguanidine |  | 45 |  |  | HBr |
| 93 | N-(4-benzyloxy-phenyl)-N'-(4-tert-butylphenyl)guanidine |  | 91 | 48 |  | HCl |
| 94 | N,N'-bis-(3-(1'-methyl-2'-phenyl)ethyl)guanidine |  | 66 |  |  | HCl |
| 95 | N-methyl-N-4-benzyloxyphenyl-N'-(4-tert-butyl-phenyl)guanidine |  | 100 | 44 |  | mesylate |
| 96 | N,N'-bis-(4-hexyl-phenyl)guanidine |  |  | 54 | 54 | mesylate |
| 97 | N-(3-(1-(4'-ethoxy)benzyl)-phenethyl)-N'-(4-tert-butylphenyl)-guanidine |  |  | 31 |  | mesylate |
| 98 | N-(4-benzyloxy-phenyl)-N'-methyl-N-(4-tert-butylphenyl)guanidine |  |  | 28 |  | mesylate |
| 99 | N-(3-(4-tert-butyl-benzyloxy)phenyl)-N'-(4-tert-butylphenyl)guanidine |  |  | 20 |  | mesylate |
| 100 | N-(3-(1'-benzyl-butyl)phenyl)-N'-(4-tert-butylphenyl)-guanidine |  |  | 20 |  | mesylate |
| 101 | N,N'-bis-(4-butyl-phenyl)-N-methyl-guanidine |  |  | 35 |  | HCl |
| 102 | N,N'-bis-(4-tert-butylphenyl)-N,N'-dimethylguanidine |  |  | 73 | 18 | HCl |
| 103 | N-(3-naphthyl-methyleneoxy-phenyl)-N'-(4-tert-butylphenyl)-guanidine |  |  | 50 |  | mesylate |
| 104 | N-(4-benzyloxy-phenyl)-N'-(4-butylphenyl)-guanidine |  |  | 76 |  | HCl |
| 105 | N,N'-bis-(4-butyl-phenyl)-N-butyl-guanidine |  |  | 66 | 24 | HCl |
| 106 | N-3-(benzyloxy-methyl)phenyl-N'-(4-tert-butylphenyl)guanidine |  |  | 48 |  | mesylate |
| 107 | N-(3,4-bis-butyloxy-phenyl)-N'-(4-tert-butylphenyl)guanidine |  |  | 34 |  | oxalate |
| 108 | N-(3-benzyloxy)-phenyl-N'-(4-tert-butyl-phenyl)guanidine |  |  | 49 |  | mesylate |
| 109 | N,N'-bis-(3-butoxy-4-methoxy)phenyl-guanidine |  |  | 86 |  | HBr |
| 110 | N-(4-benzyloxy-phenyl), methyl-N'-(4-butyl-phenyl)guanidine |  |  | 77 |  | mesylate |
| 111 | N,N'-bis-(6-tretra-linyl)guanidine |  |  | 61 |  | HBr |
| 117 | N-(5-acenaphthyl)-N'-(1-benz[cd]indo-linyl)guanidine |  | 39 |  |  | HCl |
| 138 | N-(bis(4-phenoxy-phenyl)guanidine |  |  | 57 |  | HBr |
| — | N,N'-bis(benzyl-oxyphenyl)guanidine |  |  | 46 |  | mesylate |
| — | N-(4-benzyloxy-phenyl)-N'-(4-benzylthiophenyl)-guanidine |  |  | 81 |  | mesylate |
| 140 | N-(3-benzyloxy- |  |  | 44 |  | mesylate |

TABLE 1f-continued

Additional Compounds of the Invention
(Including Compounds of Formulas I–V)

| Ex. No. | Name | % Inhibition of $^3$H-Glu Rel @ 3 μM | @ 1 μM | @ 0.3 μM | @ 0.1 μM | Salt |
|---|---|---|---|---|---|---|
|  | phenyl)-N'-(4-(azophenyl)-phenyl)guanidine |  |  |  |  |  |
| — | N,N'-bis(3-benzyl-oxyphenyl)-N'-methylguanidine |  | 67 |  |  | HCl |
| — | N-(3-benzyloxy-phenyl)-N'-(4-benzyloxy-phenyl)-N'-methyl-guanidine |  | 55 |  |  | mesylate |
| — | N,N'-bis(4-benzyl-oxyphenyl)-N'-methylguanidine |  | 22 |  |  | mesylate |

EXAMPLE 147

Inhibition of $^{45}$Ca uptake through Presynaptic Ca Channels

Compounds of the invention were tested to determine their ability to inhibit voltage-activated calcium channels in nerve terminals of mammalian brain. Said voltage-activated calcium channels directly control neurotransmitter release (see Nachsen, D. A. et al., *J. Gen Physiol.*, 79:1065–1087 (1982)). The uptake of $^{45}$Ca into brain synaptosomes was performed by an adaptation of the method of Nachsen and Blaustein (*J. Physiol.*, 361:251–258 (1985)), as previously described [Goldin et al., PCT/US92101050]. The principle of the method involves opening ion permeation through synaptosomal calcium channels by high K$^+$-induced depolarization of the synaptosomal preparation. The rapid component of $^{45}$Ca uptake measured by this procedure is mediated by presynaptic calcium channels.

Briefly, synaptosomes are prepared by the method of Hajos (*Brain Res.*, 93:485–489 (1975)). Freshly prepared synaptosomes (8 μl) were suspended in low potassium "LK" buffer (containing 3 mM KCl). Test compounds in 8 μl LK were added to synaptosomes to final concentrations ranging from 0.3 μM to 100 μM, and the mixture was preincubated for 5 minutes at room temperature. $^{45}$Ca uptake was then initiated by adding isotope in either LK or in buffer ("HK") containing high [potassium] (150 mM KCl). After 5 seconds, the $^{45}$Ca uptake was stopped by adding 0.9 ml quench buffer (LK +10 mM EGTA). This solution was then filtered under vacuum and the filters washed with 15 ml of quench buffer.

Washed filters were subjected to scintillation spectrophotometry to determine the extent of $^{45}$Ca uptake. Net depolarization-induced $^{45}$Ca uptake was determined for each concentration of each compound tested, as the difference between $^{45}$Ca uptake in HK and LK buffers. Results were plotted as % inhibition of depolarization-induced $^{45}$Ca uptake vs. [compound] for each compound tested. Representative IC$_{50}$ for inhibition of depolarization-induced $^{45}$Ca uptake are presented below in the tables (2a–2d) below which together are identified as Table 2.

TABLE 2

Inhibition of $^{45}$Ca uptake through presynaptic Ca channels

TABLE 2a

Compounds of Formula IA

| Example No. | Name | IC$_{50}$, block of $_{45}$Ca uptake, μM | Salt |
|---|---|---|---|
| 1 | N-(4-sec-butylphenyl)-N-(4-tert-butylbenzyl)guanidine | 6.1 | HCl |
| 2 | N-(5-acenaphthyl)-N-(4-tert-butylbenzyl)guanidine | 8.1 | FB |

TABLE 2b

Compounds of Formula IIIA

| Example No. | Name | IC$_{50}$, block of $^{45}$Ca uptake, μM | Salt |
|---|---|---|---|
| 9 | N-(5-acenaphthyl)-N'-(1-naphthyl-methylene)guanidine | 7.8 | Mesylate |

TABLE 2c

Compounds of Formula IV

| Example No. | Name | IC$_{50}$, block of $^{45}$Ca uptake, μM | Salt |
|---|---|---|---|
| 4 | N,N'-bis(4-sec-butylphenyl)guanidine | 11.2 | HCl |
| 6 | N,N'-bis(4-sec-butylphenyl)-N,N'-bismethyl guanidine | 5.9 | HCl |
| 13 | N,N'-bis(4-tert-butylphenyl)guanidine | 1.5 | FB |
| 15 | N-(4-methoxynaphthyl)-N'-(2,3,4-trichlorophenyl)guanidine | 1.7 | HCl |

EXAMPLE 148

Inhibition of $^{45}$Ca uptake through L-type (dihydropyridine-sensitive) Calcium Channels Compounds of the invention representative of each of the major classes of agents claimed herein were tested to determine their ability to inhibit voltage-activated, dihydropyridine-sensitive L-type calcium channels in clonal GH4C1 pituitary cells. Said voltage-activated L-type calcium channels are found in cardiac muscle, vascular smooth muscle, and the cardiac Purkije cell conduction system. They are the sites of action of the major classes of Ca antagonists employed to treat hypertension, angina, cardiac arrhythmias, and related disorders. L-type Ca channels are also the sites of action of certain neuroprotective dihydropyridine Ca antagonists such as nimodipine.

The uptake of $^{45}$Ca into GH4C1 cells was performed by an adaptation of the method of Tan, K. et al. (*J. Biol. Chem.*, 259:418–426 (1984)). The principle of the method involves activating ion permeation through synaptosomal calcium channels by high K$^+$-induced depolarization of the synaptosomal preparation. The uptake of $^{45}$Ca measured by this procedure is mediated by presynaptic L-type calcium channels, and is sensitive to dihydropyridine, phenylalkylamine, and benzothiazipine Ca antagonists at therapeutically relevant concentrations [Tashjian et al., ibid.]. The adaptation of the aforementioned method involves growing GH4C1 cells in 96-well culture plates, and is designed to provide a rapid and quantitative determination of the potency of various compounds in inhibiting $^{45}$Ca uptake through L-type Ca channels.

Details of method:

GH4 cells, stored in liquid nitrogen, are suspended in 15 ml growth medium (Ham's F-10 medium plus 15% heat-inactivated horse serum and 2.5% heat-inactivated fetal bovine serum). The cells are centrifuged, resuspended, and then added to T-75 flasks containing 12–15 mls Growth Medium, and incubated at 37° C. for approximately 1 week. The cells are then removed from the T75 flask after dissociation from the walls of the flask by treatment for 5 minutes at 37° C. with 1 mg/ml Viocase. The Viocase is decanted, and the cells are resuspended in -200 ml of Growth Medium. The cells are then aliquoted (200 μl/well) into each well of several 96 well plates. The cells are then grown under the aforementioned conditions for 3–4 weeks, with replacement of Growth Medium occurring twice per week. Cells are fed growth medium 24 hours before they are employed for $^{45}$Ca uptake determinations.

At the time of the assay, media is aspirated from each 96-well plate using a manifold designed to allow 50 μL of liquid to remain in each well. Each plate is washed and aspirated twice with a low K$^+$ buffer solution "LKHBBS" (in mM 5 KCl, 145 NaCl, 10 Hepes, 1 MgCl$_2$, 0.5 MgCl$_2$, 10 glucose, pH 7.4), 200 μl/well. Each plate is incubated for 10 minutes at 37° C., and aspirated as above. To each well of each plate, 50 μl of HBBS containing the drug to be tested in twice the final concentration is added. The plates are incubated for 10 minutes at room temperature. To each well of each plate, 50 μl of either of two solutions are added:

(a) LKHBBS containing 1 μCi of carrier-free $^{45}$Ca, or (b) HKHBBS (a high K$^+$ buffer containing 150 mM KCl and no NaCl, but otherwise identical to LKHBBS).

Each plate is then incubated for 5 minutes at room temperature, aspirated as above, and quenched with 200 μl/well of Quench Buffer (Ca-free LKHBBS containing 10 mM Tris-EGTA). Each plate is aspirated and rinsed with Quench Buffer a second time, then carefully aspirated to dryness. To each well of each plate 100 μl of High Safe II scintillation fluid is added. The plates are sealed, shaken, and subjected to scintillation spectrophotometry on a Microbeta 96-well Scintillation Counter (Wallac, Gaithersburg, Md., USA).

Net depolarization-induced $^{45}$Ca uptake was determined for each concentration of each compound tested, as the difference between $^{45}$Ca uptake in HKBBS and LK buffers. Results were plotted as % inhibition of depolarization-induced $^{45}$Ca uptake vs. [compound] for each compound tested. Representative IC50 for inhibition of depolarization-induced $^{45}$Ca uptake are presented below in the tables (3a–3c) below which together are identified as Table 3. The known compounds of verapamil and diltiazem were also tested pursuant to the same protocol as specified above and the following activity against L-type Ca channels was observed: verapamil: IC$_{50}$ (block of $^{45}$Ca uptake, μM) 8.0+/−4 (n=3); diltiazem: IC$_{50}$ (block of $^{45}$Ca uptake, μM) 19.7+/−6 (n=3).

TABLE 3

Inhibition of $^{45}$Ca uptake through L-type Ca channels

TABLE 3a

Compounds of Formula IA

| Example No. | Name | IC$_{50}$, block of $^{45}$Ca uptake, μM | Salt |
|---|---|---|---|
| 1 | N-(4-sec-butylphenyl)-N-(4-tert-butylbenzyl)guanidine | 1.7 | FB |
| 2 | N-(5-acenaphthyl)-N-(4-tert-butylbenzyl)guanidine | 2.1 | FB |
| 19 | N-(5-acenaphthyl)-N-(4-isopropylbenzyl)guanidine | 2.1 | HCl |

TABLE 3b

Compounds of Formula IIIA

| Example No. | Name | IC$_{50}$, block of $^{45}$Ca uptake, μM | Salt |
|---|---|---|---|
| 3 | N-(5-acenaphthyl)-N'-(benzhydryl)guanidine | 2.7 | HCl |

TABLE 3c

Compounds of Formula IV

| Example No. | Name | IC$_{50}$, block of $^{45}$Ca uptake, μM | Salt |
|---|---|---|---|
| 4 | N,N'-bis(4-sec-butylphenyl)-guanidine | 2.1 | FB |
| 6 | N,N'-bis(4-sec-butylphenyl)-N,N'-bismethyl guanidine | 4.3 | HCl |
| 13 | N,N'-bis(4-tert-butylphenyl)-guanidine | 4.1 | FB |
| 15 | N-(4-methoxynaphthyl)-N'-(2,3,5-trichlorophenyl)guanidine | 1.7 | HCl |

EXAMPLE 149

Inhibition of $^{14}$C-guanidine uptake through Type II Neuronal Voltage-activated Sodium Channels Antagonists of the neuron-specific type 11 subclass of voltage-gated Na channels are neuroprotective (Stys, P. K. et al., J. Neurosci., 12:430–439 (1992)). The ability of compounds of the invention to block voltage-activated Type II Na channels was determined in a functional assay employing a Chinese Hamster Ovary ("CHO") cell line expressing cloned Type II Na channels derived from rat brain (West, J. W. et al., Neuron 8:59–70 (1992)). The assay is based on the observation that veratridine, an alkaloid neurotoxin, causes persistent activation of sodium channels, and tetrodotoxin, a heterocyclic agent derived from puffer fish, is a potent and highly specific blocker of several major subclasses of voltage-sensitive sodium channels, including the said Type II subclass. It further takes advantage of the finding that guanidinium cation will permeate through tetrodotoxin-sensitive Na channels when said channels are opened, either by membrane depolarization (Hille, B., Ionic Channels of Excitable Membranes 2nd Edition, Sinauer Associates, Sunderland, Mass., pp. 349–353 (1992)) or by exposure to veratridine (Reith, M. E. A., Eur. J. Pharmacol., 188:33–41 (1990)). Accordingly, the assay entails measuring veratridine-stimulated, tetrodotoxin-sensitive influx of [$^{14}$C]-guanidinium ion through cloned Type II Na channels expressed in CHO cells. The protocol of the assay is as follows.

Assay protocol:

The aforementioned CHO cell line is grown by standard cell culture techniques in RPMI 1640 medium (Media Tech), supplemented with 5% fetal calf serum (Hyclone), 200 μg/ml G418 (Sigma) and 5.75 mg/ml proline (Sigma). Cells are routinely allowed to grow for 3–4 days in vitro.

Cultures are rinsed 3 times with 200 μl of "preincubation buffer" (5.4 mM KCl, 0.8mM MgSO4, 50 mM Hepes, 130 mM choline chloride, 0.1 mg/ml BSA, 1 mM guanidine HCl, 5.5 mM D-glucose, pH 7.4) and incubated with 200 μl preincubation buffer at 37° C. for 10 minutes. A 96-channel manifold connecter is used to vacuum-aspirate the buffer from the wells between rinses.

Different concentrations of the tested compounds are prepared by dilution into "uptake buffer" (preincubation buffer plus ~2.5 mCi/ml [$^{14}$C]-guanidinium HCl, ~40 mCi/mmol) containing veratridine (100 μM). Aliquots (50 μl) of these working stocks is added to the 96-well plates and incubated at room temperature for 1 hour. The veratridine-induced [$^{14}$C]-guanidinium uptake was linear with time and a good signal (4–8 fold basal uptake) was obtained following a 1 hour incubation. The following controls are also conducted in each 96-well plate: basal uptake (obtained in the absence of CNS compound and veratridine), uptake evoked by veratridine alone, and veratridine evoked uptake in the presence of 10 μM tetrodotoxin (the latter is a measure of non-specific uptake independent of Na channel activation).

The flux assay is terminated at the end of the incubation period by rinsing the 96-well plates 3 times with 200 μl/well of ice cold "wash buffer" (163 mM choline chloride, 0.8 mM Mg SO$_4$, 1.8 mM Ca Cl$_2$, 5 mM Hepes, 1 mg/ml BSA). The remaining 50 μl of wash buffer in the wells (following rinsing) is removed by vacuum aspiration with an 8-channel Drummond aspirator. 100 μl of High Safe II scintillation fluid is added to each well. The plates are sealed before shaking for 15 minutes The plates are then allowed to sit for 45 minutes before counting in a 96-well scintillation counter.

Net veratridine-induced [$^{14}$C]-guanidinium uptake was determined for each concentration of each compound tested, as the difference between [$^{14}$C]-guanidinium uptake in the presence and absence of tetrodotoxin. Results were plotted as % inhibition of veratridine-induced [$^{14}$C]-guanidinium uptake vs. [compound] for each compound tested. Representative IC$_{50}$'s for inhibition of veratridine-induced [$^{14}$C]-guanidinium uptake are presented below in the following tables (4a–4d) which together identified as Table 4.

TABLE 4

Inhibition of [$^{14}$C]-guanidinium uptake through type II sodium channels

TABLE 4a

Compounds of Formula IA

| Example No. | Name | IC$_{50}$, block of $^{14}$C guanidinium uptake, μM | Salt |
|---|---|---|---|
| 1 | N-(4-sec-butylphenyl)-N-(4-tert-butylphenyl)-guanidine | 0.8 | HCl |
| 2 | N-(5-acenaphthyl)-N-(4-tert-butylphenyl)guanidine | 1 | FB |
| 16 | N-(4-sec-butylphenyl)-N-(benzyl)guanidine | 0.5 | FB |
| 18 | N-(5-acenaphthyl)-N-(4-isopropylbenzyl)guanidine | 2.1 | HCl |
| 20 | N-(4-cyclohexyl)-N-(4-tert-butylbenzyl)guanidine | 0.9 | HCl |
| 21 | N-(fluorenyl)-N-(4-tert-butylbenzyl)guanidine | 1.9 | HCl |
| 22 | N-(4-sec-butylphenyl)-N-(transcinnamyl)guanidine | 0.5 | HCl |
| 24 | N-(3-biphenyl)-N-(4-tert-butylbenzyl)guanidine | 1.8 | HCl |
| 26 | N-(3-trifluoromethoxy-phenyl)-N-(4-tert-butyl-benzyl)guanidine | 0.7 | HCl |
| 27 | N-(4-methoxynaphthyl)-N'-(4-tert-butylbenzyl)guanidine | 1.2 | HCl |
| 48 | N-(3-iodophenyl)-N-(4-tert-butylbenzyl)guanidine | 0.4 | HCl |
| 49 | N-(4-chloronaphthyl)-N-(4-tert-butylbenzyl)guanidine | 2.2 | HCl |

TABLE 4b

Compounds of Formula II

| Example No. | Name | IC$_{50}$, block of $^{14}$C guanidinium uptake, μM | Salt |
|---|---|---|---|
| 11 | N,N'-bis(fluorenyl)guanidine | 0.9 | HBr |

TABLE 4c

Compounds of Formula IIIA

| Example No. | Name | IC$_{50}$, block of $^{14}$C guanidinium uptake, μM | Salt |
|---|---|---|---|
| 9 | N-(5-acenaphthyl)-N'-(1-naphthyl-methylene)guanidine | 0.7 | HCl |
| 42 | N-(5-acenaphthyl)-N'-(2-methyl-3-phenylpropyl)guanidine | 0.7 | HCl |

TABLE 4d

Compounds of Formula IV

| Example No. | Name | IC$_{50}$, block of $^{14}$C guanidinium uptake, μM | Salt |
|---|---|---|---|
| 4 | N,N'-bis(4-sec-butylphenyl)guanidine | 0.8 | HCl |
| 6 | N,N'-bis(4-sec-butylphenyl)-N,N'-bismethyl guanidine | 0.6 | HCl |
| 8 | N,N'-bis(4-sec-butylphenyl-2-iminopyrimidazolidine | 0.2 | HBr |
| 12 | N,N'-bis(4-tert-butylphenyl)guanidine | 1.5 | FB |
| 13 | N-(4-tert-butylphenyl)-N'-(2,3,4-trichlorophenyl)guanidine | 0.9 | HCl |
| 14 | N-(4-methoxynaphthyl)-N'-(2,3,4-trichlorophenyl)guanidine | 1.8 | HCl |

EXAMPLE 150
In vivo Anticonvulsant activity in the DBA/2 mouse model

The in vivo potency of compounds of the present invention is exemplified by data summarized in the Table V below and obtained pursuant to the following protocol.

Compounds were tested for their effectiveness in preventing seizures in DBA/2 mice which have a unique sensitivity to auditory stimulation. Exposure to loud high-frequency sounds can trigger seizure activity in these animals. This sensitivity develops from postnatal day 12 and peaks around day 21 and slowly diminishes as the animals mature. The unusual response to auditory stimulation in this strain of mouse is believed to be due to a combination of early myelination (causing an unusually low excitatory threshold) and delayed development of inhibitory mechanisms. Glutamate, the predominant excitatory neurotransmitter, has been implicated in this response. Blockade of glutamate receptors of the NMDA and AMPA subtypes, prevents audiogenic seizures in these mice. Compounds that block the release of glutamate should similarly act to prevent seizure activity, and may be therapeutic in other neurologic disorders such as stroke, which also involves glutamate-mediated damage.

Mice were injected intraperitoneally with the compound specified in Table V below or with vehicle control, 30 minutes prior to being placed in a bell jar and turning on the auditory stimulus (12 KHz sine wave at 110–120 db). Administered doses are specified in Table V as milligram of compound per kilogram bodyweight of mouse. The auditory stimulus was left on for 60 seconds and mice reactions were timed and recorded.

Percentage inhibition was determined with reference to vehicle controls. Results are shown in the Table 5 below.

TABLE 5

| Example No. | Compound Name | Dose (mg/kg) | Audiogenic Response % Inhib. | Salt |
|---|---|---|---|---|
| 8 | N,N'-bis-(4-sec-butyl-2-iminopyrimidazolidine | 2<br>4 | 41<br>75 | HBr |
| 29 | N-(5-acenaphthyl)-N'-(indolinyl)guanidine | 20<br>40 | 42<br>81 | mesylate |
| 1 | N-(4-sec-butylphenyl)-N-(4-tert-butylbenzyl)guanidine | 40<br>10<br>20 | 91<br>54<br>80.5 | HCl |
| 37 | N,N'-bis(4-n-butylphenyl)-guanidine | 25<br>40 | 82<br>92 | mesylate |
| 72 | N-(4-sec-butylphenyl)-N-(4-t-butylbenzyl)-N'-pyrrolidinylguanidine | 40<br>20 | 81<br>52 | HCl |
| — | N,N'-bis(4-n-butoxyphenyl)guanidine | 20<br>40 | 60<br>82 | |
| 73 | N-(4-sec-butylphenyl)-N-(4-t-butylbenzyl)-N'-(4-thiomorpholinyl)guanidine | 20<br>40 | 23<br>89 | HCl |
| — | N-(4-benzyloxyphenyl)-N'-(4-phenoxyphenyl)guanidine | 20<br>40 | 16<br>93 | |
| 104 | N-(4-benzyloxyphenyl)-N'-(4-butylphenyl)guanidine | 20<br>40 | 40<br>90 | HCl |
| 106 | N-3-benzyloxymethyl)phenyl-N'-(4-tert-butyl-phenyl)guanidine | 40 | 93 | mesylate |
| 108 | N-(3-benzyloxy)phenyl-N'-(4-tert-butylphenyl)guanidine | 40 | 80 | mesylate |
| 79 | N-(4-benzyloxyphenyl)-N-(4-tert-butylbenzyl)-N'-(4-morpholinyl)guanidine | 20<br>40 | 41<br>68 | HCl |
| 110 | N-(4-benzyloxyphenyl)-N-methyl-N'-(4-butylphenyl)-guanidine | 20<br>40 | 42.3<br>92.5 | mesylate |

The invention has been described in detail with reference to preferred embodiments thereof. However, it will be appreciated that those skilled in the art, upon consideration of this disclosure, may make modifications and improvements within the spirit and scope of the invention.

What is claimed is:

1. A method for treating a disorder of the nervous system in which the pathophysiology of the disorder involves excessive or inappropriate release of a neurotransmitter from neuronal cells comprising administering to a mammal exhibiting symptoms of said disorder or susceptible to said disorder an effective amount of a compound of the following Formula III:

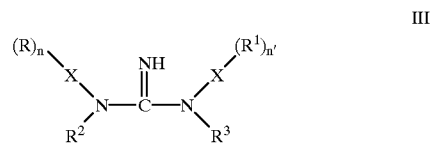

wherein

R and $R^1$ are each independently substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted aryloxy having from 6 to about 20 carbon atoms, substituted or unsubstituted aralkoxy having from 6 to about 20 carbon atoms, substituted or unsubstituted carbocyclic aryl having at least 5 ring atoms, substituted or unsubstituted aralkyl having at least 5 ring atoms, or a substituted or unsubstituted heteroaromatic or heteroalicyclic group having 1 to 3 rings, 3 to 8 ring members in each ring and 1 to 3 heteroatoms, with at least one of R and $R^1$ being substituted or unsubstituted aryloxy, substituted or unsubstituted aralkoxy, substituted or unsubstituted alkylsulfinyl or substituted or unsubstituted alkylsulfonyl;

$R^2$ and $R^3$ each independently being hydrogen, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted aryloxy having from 6 to about 20 carbon atoms; substituted or unsubstituted aralkoxy having from 6 to about 20 carbon atoms; substituted or unsubstituted aminoalkyl having 1 to about 20 carbon atoms; substituted or unsubstituted alkylthio having 1 to about 20 carbon atoms; substituted or unsubstituted alkylsulfinyl having 1 to about 20 carbon atoms; substituted or unsubstituted alkylsulfonyl having 1 to about 20 carbon atoms; substituted or unsubstituted carbocyclic aryl having at least 5 ring atoms, substituted or unsubstituted aralkyl having at least 5 ring atoms, or a substituted or unsubstituted heteroaromatic or heteroalicyclic group having 1 to 3 rings, 3 to 8 ring members in each ring and 1 to 3 heteroatoms;

n and n' independently are each equal to 1, 2, or 3;

X and X' are each independently a chemical bond, substituted or unsubstituted alkylene having 1 to about 8 carbon atoms, with at least one of X and X' being other than a chemical bond; and pharmaceutically acceptable salts thereof.

2. A method for treating a neurodegenerative disease comprising administering to a mammal exhibiting symptoms of the disease or susceptible to the disease an effective amount of a compound of the following Formula III:

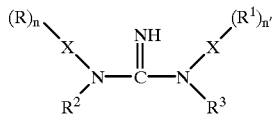

III wherein
- R and $R^1$ are each independently substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted aryloxy having from 6 to about 20 carbon atoms, substituted or unsubstituted aralkoxy having from 6 to about 20 carbon atoms, substituted or unsubstituted carbocyclic aryl having at least 5 ring atoms, substituted or unsubstituted aralkyl having at least 5 ring atoms, or a substituted or unsubstituted heteroaromatic or heteroalicyclic group having 1 to 3 rings, 3 to 8 ring members in each ring and 1 to 3 heteroatoms,
- with at least one of R and $R^1$ being substituted or unsubstituted aryloxy, substituted or unsubstituted aralkoxy, substituted or unsubstituted alkylsulfinyl or substituted or unsubstituted alkylsulfonyl;
- $R^2$ and $R^3$ each independently being hydrogen, substituted or unsubstituted alkyl having from 1 to about 20 carbon atoms, substituted or unsubstituted alkenyl having from 2 to about 20 carbon atoms, substituted or unsubstituted alkynyl having from 2 to about 20 carbon atoms, substituted or unsubstituted alkoxy having from 1 to about 20 carbon atoms, substituted or unsubstituted aryloxy having from 6 to about 20 carbon atoms; substituted or unsubstituted aralkoxy having from 6 to about 20 carbon atoms; substituted or unsubstituted aminoalkyl having 1 to about 20 carbon atoms; substituted or unsubstituted alkylthio having 1 to about 20 carbon atoms; substituted or unsubstituted alkylsulfinyl having 1 to about 20 carbon atoms; substituted or unsubstituted alkylsulfonyl having 1 to about 20 carbon atoms; substituted or unsubstituted carbocyclic aryl having at least 5 ring atoms, substituted or unsubstituted aralkyl having at least 5 ring atoms, or a substituted or unsubstituted heteroaromatic or heteroalicyclic group having 1 to 3 rings, 3 to 8 ring members in each ring and 1 to 3 heteroatoms;
- n and n' independently are each equal to 1, 2, or 3;
- X and X' are each independently a chemical bond, substituted or unsubstituted alkylene having 1 to about 8 carbon atoms, with at least one of X and X' being other than a chemical bond; and pharmaceutically acceptable salts thereof.

3. The method of claim 2 wherein the disease is Parkinson's disease, Huntington's disease, Amyotrophic Lateral Sclerosis, Alzheimer's disease, Down's Syndrome, Korsakoff's disease, olivopontocerebellar atrophy, HIV-induced demnetia and blindness, multi-infaract dementia or epilepsy.

4. The method of any one of claims 1–3 wherein $R^2$ is hydrogen, substituted or unsubstituted alkyl, substituted or unsubstituted alkenyl, substituted or unsubstituted alkynyl, substituted or unsubstituted alkoxy, substituted or unsubstituted aminoalkyl, substituted or unsubstituted alkylthio, substituted or unsubstituted alkylsulfinyl, or substituted or unsustituted alkylsulfonyl.

5. A method of any one of claims 1–3 wherein the compound is
- N-(5-acenaphthyl)-N'-(1-methyl-2-phenoxyethyl)guanidine;
- N-(5-acenaphthyl)-N'-(1-methyl-2-phenoxyethyl)-N-methylguanidine;
- N-(5-acenaphthyl)-N'-(1-methyl-2-phenoxyethyl)-N'-methylguanidine; or
- N-(5-acenaphthyl)-N'-(1-methyl-2-phenoxyethyl)-N,N'-dimethylguanidine; or a pharmaceutically acceptable salt thereof.

6. A method of any one of claims 1–3 wherein the compound is
- N,N'-(sec-butylphenyl)-N'-(2-phenoxyethyl)guanidine; or
- N,N'-(secbutylphenyl)-N'-(2-phenoxyethyl)-N-methylguanidine;

or a pharmaceutically acceptable salt thereof.

7. A method of claim 1 wherein X or X' is alkylene having 1 to about 4 carbon atoms.

8. A method of claim 2 wherein X or X' is alkylene having 1 to about 4 carbon atoms.

9. A method of claim 3 wherein X or X' is alkylene having 1 to about 4 carbon atoms.

10. A method of claim 1 wherein X is alkylene having 1 to about 4 carbon atoms and X' is a chemical bond.

11. A method of claim 2 wherein X is alkylene having 1 to about 4 carbon atoms and X' is a chemical bond.

12. A method of claim 3 wherein X is alkylene having 1 to about 4 carbon atoms and X' is a chemical bond.

* * * * *